(12) United States Patent
Dimitrov et al.

(10) Patent No.: US 9,676,846 B2
(45) Date of Patent: Jun. 13, 2017

(54) HUMAN MONOCLONAL ANTIBODIES THAT BIND INSULIN-LIKE GROWTH FACTOR (IGF) I AND II

(71) Applicant: THE UNITED STATES OF AMERICA, as represented by the Secretary, Department of Health and Human Services, Washington, DC (US)

(72) Inventors: Dimiter S. Dimitrov, Frederick, MD (US); Zhongyu Zhu, Frederick, MD (US); Qi Zhao, Frederick, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/832,803

(22) Filed: Aug. 21, 2015

(65) Prior Publication Data
US 2016/0024199 A1 Jan. 28, 2016

Related U.S. Application Data

(63) Continuation of application No. 14/111,507, filed as application No. PCT/US2012/033128 on Apr. 11, 2012, now Pat. No. 9,150,644.

(60) Provisional application No. 61/474,664, filed on Apr. 12, 2011, provisional application No. 61/548,164, filed on Oct. 17, 2011.

(51) Int. Cl.
*A61K 39/395* (2006.01)
*C12N 5/00* (2006.01)
*C12N 15/00* (2006.01)
*C12P 21/08* (2006.01)
*C07K 16/22* (2006.01)
*G01N 33/74* (2006.01)
*G01N 33/574* (2006.01)
*A61K 39/00* (2006.01)

(52) U.S. Cl.
CPC ....... *C07K 16/22* (2013.01); *G01N 33/57484* (2013.01); *G01N 33/74* (2013.01); *A61K 2039/505* (2013.01); *C07K 2317/21* (2013.01); *C07K 2317/31* (2013.01); *C07K 2317/76* (2013.01); *C07K 2317/92* (2013.01); *G01N 2333/475* (2013.01); *G01N 2800/7028* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,817,837 A | 6/1974 | Rubenstein et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dryer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,939,350 A | 2/1976 | Kronick et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,275,149 A | 6/1981 | Litman et al. |
| 4,277,437 A | 7/1981 | Maggio |
| 4,366,241 A | 12/1982 | Tom et al. |
| 4,376,110 A | 3/1983 | David et al. |
| 4,391,904 A | 7/1983 | Litman et al. |
| 4,399,216 A | 8/1983 | Axel et al. |
| 4,486,530 A | 12/1984 | David et al. |
| 4,681,581 A | 7/1987 | Coates |
| 4,683,195 A | 7/1987 | Mullis et al. |
| 4,683,202 A | 7/1987 | Mullis |
| 4,735,210 A | 4/1988 | Goldenberg |
| 4,740,461 A | 4/1988 | Kaufman |

(Continued)

FOREIGN PATENT DOCUMENTS

| | | |
|---|---|---|
| EP | 0 256 055 B1 | 8/1991 |
| EP | 0 338 841 B1 | 3/1995 |

(Continued)

OTHER PUBLICATIONS

Belagaje et al., "Total synthesis of a tyrosine suppressor transfer RNA gene. XIV. Chemical synthesis of oligonucleotide segments corresponding to the terminal regions," *J Biol Chem.* 254(13):5765-80 (Jul. 10, 1979).

Bendig, "Humanization of rodent monoclonal antibodies by CDR grafting," *Methods: A companion to Methods in Enzymology* 8:83-93 (1995).

Bird et al., "Single-chain antigen-binding proteins," *Science* 242(4877):423-426 (Oct. 21, 1988) and Erratum in: *Science* 244(4903):409 (Apr. 28, 1989).

(Continued)

*Primary Examiner* — Marianne P Allen
(74) *Attorney, Agent, or Firm* — Klarquist Sparkman, LLP

(57) ABSTRACT

Disclosed herein are human monoclonal antibodies that specifically bind both IGF-I and IGF-II with picomolar affinity and potently inhibit the IGF-IR signal transduction function. These antibodies are active in both an IgG and a scFv format. Bispecific forms of these antibodies are also disclosed. Nucleic acids encoding these antibodies, vectors including these nucleic acids, and host cells transformed with these vectors are also disclosed herein. Also disclosed are pharmaceutical compositions including these antibodies. Methods are provided for treating a subject with cancer and for inhibiting phosphorylation of the insulin-like growth factor-I receptor. Methods are also provided for diagnosing cancer.

28 Claims, 18 Drawing Sheets

(56) References Cited

U.S. PATENT DOCUMENTS

| | | | |
|---|---|---|---|
| 4,816,567 A | 3/1989 | Cabilly et al. |
| 4,912,040 A | 3/1990 | Kaufman et al. |
| 4,959,455 A | 9/1990 | Clark et al. |
| 5,101,827 A | 4/1992 | Goldenberg |
| 5,102,990 A | 4/1992 | Rhodes |
| 5,194,594 A | 3/1993 | Khawli et al. |
| 5,401,629 A | 3/1995 | Harpold et al. |
| 5,436,128 A | 7/1995 | Harpold et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Lonberg et al. |
| 5,625,825 A | 4/1997 | Rostoker et al. |
| RE35,500 E | 5/1997 | Rhodes |
| 5,633,425 A | 5/1997 | Lonberg et al. |
| 5,643,763 A | 7/1997 | Dunn et al. |
| 5,648,471 A | 7/1997 | Buttram et al. |
| 5,661,016 A | 8/1997 | Lonberg et al. |
| 5,693,761 A | 12/1997 | Queen et al. |
| 5,693,792 A | 12/1997 | Torii et al. |
| 5,697,902 A | 12/1997 | Goldenberg |
| 5,703,057 A | 12/1997 | Johnston et al. |
| 5,714,350 A | 2/1998 | Co et al. |
| 5,721,367 A | 2/1998 | Kay et al. |
| 5,733,743 A | 3/1998 | Johnson et al. |
| 5,741,957 A | 4/1998 | Deboer et al. |
| 5,750,172 A | 5/1998 | Meade et al. |
| 5,756,687 A | 5/1998 | Denman et al. |
| 5,770,429 A | 6/1998 | Lonberg et al. |
| 5,777,085 A | 7/1998 | Co et al. |
| 5,789,215 A | 8/1998 | Berns et al. |
| 5,789,650 A | 8/1998 | Lonberg et al. |
| 5,814,318 A | 9/1998 | Lonberg et al. |
| 5,827,690 A | 10/1998 | Meade et al. |
| 5,914,241 A | 6/1999 | Valkirs |
| 5,939,598 A | 8/1999 | Kucherlapati et al. |
| 5,965,375 A | 10/1999 | Valkirs |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,673,986 B1 | 1/2004 | Kucherlapati et al. |
| 7,064,244 B2 | 6/2006 | Kucherlapati et al. |
| 8,071,323 B2 | 12/2011 | Dimitrov et al. |

FOREIGN PATENT DOCUMENTS

| | | |
|---|---|---|
| EP | 0 216 846 B2 | 4/1995 |
| EP | 0 463 151 B1 | 6/1996 |
| EP | 0 546 073 B1 | 9/1997 |
| EP | 0 323 997 B1 | 7/1998 |
| EP | 0 505 075 A1 | 2/2005 |
| WO | WO 91/17271 A1 | 11/1991 |
| WO | WO 92/01047 A1 | 1/1992 |
| WO | WO 92/03918 A1 | 3/1992 |
| WO | WO 92/22645 A1 | 12/1992 |
| WO | WO 92/22647 A1 | 12/1992 |
| WO | WO 92/22670 A1 | 12/1992 |
| WO | WO 93/06213 A1 | 4/1993 |
| WO | WO 93/12227 A1 | 6/1993 |
| WO | WO 94/00569 A1 | 1/1994 |
| WO | WO 94/02602 A1 | 2/1994 |
| WO | WO 94/25585 A1 | 11/1994 |
| WO | WO 94/29444 A1 | 12/1994 |
| WO | WO 96/14436 A1 | 5/1996 |
| WO | WO 96/34096 A1 | 10/1996 |
| WO | WO 97/08320 A1 | 3/1997 |
| WO | WO 97/13852 A1 | 4/1997 |
| WO | WO 97/38137 A1 | 10/1997 |
| WO | WO 98/24884 A1 | 6/1998 |
| WO | WO 98/24893 A2 | 6/1998 |
| WO | WO 00/37504 A2 | 6/2000 |
| WO | WO 01/14424 A2 | 3/2001 |
| WO | WO 03/093317 A1 | 11/2003 |
| WO | WO 03/100008 A2 | 12/2003 |
| WO | WO 2004/092219 | 10/2004 |
| WO | WO 2005/058967 | 6/2005 |
| WO | WO 2007/022172 A1 | 2/2007 |
| WO | WO 2007/070432 A2 | 6/2007 |
| WO | WO 2007/118214 A2 | 10/2007 |
| WO | WO 2009/137758 A2 | 11/2009 |
| WO | WO 2010/066868 A2 | 6/2010 |

OTHER PUBLICATIONS

Blake and Litzi-Davis, "Evaluation of peptide libraries: an iterative strategy to analyze the reactivity of peptide mixtures with antibodies," *Bioconjug Chem* 3(6):510-513 (Nov.-Dec. 1992).

Bowie et al., "A method to identify protein sequences that fold into a known three-dimensional structure," *Science* 253(5016):164-170 (Jul. 12, 1991).

Burchardt et al., "Are elevated levels of IGF-1 caused by coronary arteriesoclerosis?: Molecular and clinical analysis," Protein Journal 29(8):538-544 (Nov. 2010).

Burtrum et al., "A fully human monoclonal antibody to the insulin-like growth factor I receptor blocks ligand-dependent signaling and inhibits human tumor growth in vivo," *Cancer Res* 63(24):8912-8921 (Dec. 15, 2003).

Casset et al., "A peptide mimetic of an anti-CD4 monoclonal antibody by rational design," *Biochemical and Biophysical Research Communications* 307:198-205 (2003).

Cevc et al., "Ultraflexible vesicles, Transfersomes, have an extremely low pore penetration resistance and transport therapeutic amounts of insulin across the intact mammalian skin," *Biochim Biophys Acta.* 1368(2):201-215 (Jan. 19, 1998).

Chao et al., "Isolating and engineering human antibodies using yeast surface display," Nature Protocols 1(2):755-768 (Jan. 1, 2006).

Chaudhary et al., "A rapid method of cloning functional variable-region antibody genes in *Escherichia coli* as single-chain immunotoxins," *Proc Natl Acad Sci USA* 87(3):1066-70 (Feb. 1990).

Chen et al., "Intracellular antibodies as a new class of therapeutic molecules for gene therapy," *Hum Gene Ther* 5(5):595-602 (May 1994).

Chiswell and MaCafferty, "Phage antibodies: will new 'coliclonal' antibodies replace monoclonal antibodies?," *Trends Biotechnol* 10(3):80-84 (Mar. 1992).

Chothia and Lusk, "AM. Canonical structures for the hypervariable regions of immunoglobulins," *J Mol Biol* 196(4):901-917 (Aug. 20, 1987).

Chothia et al., "Conformations of immunoglobulin hypervariable regions," *Nature* 342(6253):877-883 (Dec. 21-28, 1989).

Colao et al., "Relationships between serum IGF1 levels, blood pressure, and glucose tolerance: an observational, exploratory study in 404 subjects," *European Journal of Endocrinology* 159(4):389-97 (Oct. 2008).

Colman, "Effects of amino acid sequence changes on antibody-antigen interactions," *P.M. Research in Immunology* 145:33-66 (1944).

Cwirla et al., "Peptides on phage: a vast library of peptides for identifying ligands," *Proc Natl Acad Sci USA* 87(16):6378-6382 (Aug. 1990).

Dranoff et al., "Vaccination with irradiated tumor cells engineered to secrete murine granulocyte-macrophage colony-stimulating factor stimulates potent, specific and long-lasting anti-tumor immunity," *Proc Natl Acad Sci U S A* 90(8):3539-3543 (Apr. 15, 1993).

Evans et al., "Design of nonpeptidal ligands for a peptide receptor: cholecystokinin antagonists," *J Med Chem* 30(7):1229-1239 (Jul. 1987).

Fanger et al., "Production and use of anti-FcR bispecific antibodies," *Immunomethods* 4(1):72-81 (Feb. 1994).

Fauchere, "Elements for the Rational Design of Peptide Drugs," *J. Adv. Drug Res.*, 15:29 (1986).

(56) References Cited

OTHER PUBLICATIONS

Felici et al., "Selection of antibody ligands from a large library of oligopeptides expressed on a multivalent exposition vector," *J Mol Biol* 222(2):301-310 (Nov. 20, 1991).
Fry et al., "Specific, irreversible inactivation of the epidermal growth factor receptor and erbB2, by a new class of tyrosine kinase inhibitor," *Proc Natl Acad Sci U S U* 95(20):12022-12027 (Sep. 29, 1998).
Furet et al., "Modelling study of protein kinase inhibitors; binding mode of staurosporine and origin of the selectivity of CGP 52411," *J Comput Aided Mol Des* 9(6):465-472 (Dec. 1995).
Gao et al., "A method for the generation of combinatorial antibody libraries using pIX phage display," *Proc Natl Acad Sci U S A* 99(20):12612-12616 (Oct. 1, 2002).
Gilman, "G proteins: Transducers of receptor-generated signals," *Ann. Rev. Biochem* 56:625-649 (1987).
Ginalski et al., "Modelling of active forms of protein kinases: p38—a case study," *Acta Biochim Pol.* 44(3):557-564 (1997).
Gorman et al., "The Rous sarcoma virus long terminal repeat is a strong promoter when introduced into a variety of eukaryotic cells by DNA-mediated transfection," *Proc Natl Acad Sci USA* 79(22):6777-6781 (Nov. 1982).
Goya et al., "Growth inhibition of human prostate cancer cells in human adult bone implanted into nonobese diabetic/severe combined immunodeficient mice by a ligand-specific antibody to human insulin-like growth factors," *Cancer Res.* 64(17):6252-6258 (Sep. 1, 2004).
Green and Jakobovits, "Regulation of B cell development by variable gene complexity in mice reconstituted with human immunoglobulin yeast artificial chromosomes," *J Exp Med.* 188(3):483-495 (Aug. 3, 1998).
Green et al., "Antigen-specific human monoclonal antibodies from mice engineered with human Ig heavy and light chain YACs," *Nat Genet* 7(1):13-21 (May 1994).
Grosschedl and Baltimore, "Cell-type specificity of immunoglobulin gene expression is regulated by at least three DNA sequence elements," *Cell* 41(3):885-897 (Jul. 4, 1985).
Hailey et al., "Neutralizing anti-insulin-like growth factor receptor 1 antibodies inhibit receptor function and induce receptor degradation in tumor cells," *Mol Cancer Ther.* 1(14):1349 (Dec. 2002).
Hanes and Pluckthun, "In vitro selection and evolution of functional proteins by using ribosome display," *Proc Natl Acad Sci U S A* 94(10):4937-4942 (May 13, 1997).
Hanes et al., "New advances in microsphere-based single-dose vaccines," *Adv Drug Deliv Rev* 28(1):97-119 (Oct. 13, 1997).
Harding et al., "Turnover of Ia-peptide complexes is facilitated in viable antigen-presenting cells: biosynthetic turnover of Ia vs. peptide exchange," *Proc Natl Acad Sci U S A* 86(11):4230-4234 (Jun. 1989).
Hodgson, "Making monoclonals in microbes," *Biotechnology (NY)* 9(5):421-425 (May 1991).
Hofmann et al., "A model of Cdc25 phosphatase catalytic domain and Cdk-interaction surface based on the presence of a rhodanese homology domain," *J Mol Biol* 282(1):195-208 (Sep. 11, 1998).
Holliger et al., "Diabodies: small bivalent and bispecific antibody fragments," *Proc Natl Acad Sci U S A* 90(14):6444-6448 (Jul. 15, 1993).
Hoogenboom and Chames, "Natural and Designer Binding Sites Made by Phage Display Technology," *Immunology Today* 21(8):371-378 (Aug. 2000).
Hoogenboom et al., "Building antibodies from their genes," *Immunol. Reviews* 130:43-68 (1992).
Houghten et al., "The use of synthetic peptides combinatorial libraries for the identification of bioactive peptides," *Biotechniques* 13(3):4 12-21 (Sep. 1992).
Hsu et al., "Cloning of cDNAs for human aldehyde dehydrogenases 1 and 2," *Proc Natl Acad Sci U S A* 82(11):3771-3775 (Jun. 1985).
Hurwitz et al., "Combination immunotherapy of primary prostate cancer in a transgenic mouse model using CTLA-4 blockade," *Cancer Res.* 60(9):2444-2448 (May 1, 2000).
Huston et al., "Protein engineering of antibody binding sites: recovery of specific activity in an anti-digoxin single-chain Fv analogue produced in *Escherichia coli*," *Proc Natl Acad Sci U S A* 85(16):5879-5883 (Aug. 1988).
Hynes, "Integrins: versatility, modulation, and signaling in cell adhesion," *Cell* 69(1):11-25 (Apr. 3, 1992).
Ill et al., "Design and construction of a hybrid immunoglobulin domain with properties of both heavy and light chain variable regions," *Protein Eng* 10(8):949-957 (Aug. 1997).
International Search Report and written Opinion from parent PCT Application No. PCT/US2012/033128, 12 pages (mailed Jul. 3, 2012).
Joukov et al., "Identification of csk tyrosine phosphorylation sites and a tyrosine residue important for kinase domain structure," *Biochem J* 322(Pt 3):927-935 (Mar. 15, 1997).
Junghans et al., "Cancer Chemotherapy and Biotherapy, $2^{nd}$ ed., Chafier and Longo, Eds.," *Lippincott Raven* pp. 655-686 (1996).
Kam et al., "Cloning, sequencing, and chromosomal localization of human term placental alkaline phosphatase cDNA," *Proc Natl Acad Sci U S A* 82(24):8715-8719 (Dec. 1985).
Khorana, "Total synthesis of a gene," *Science* 203(4381):614-625 (Feb. 16, 1979).
Kostelny et al., "Formation of a bispecific antibody by the use of leucine zippers," *J Immunol* 148(5):1547-1553 (Mar. 1, 1992).
Kuwabara et al., "Efficient epitope mapping by bacteriophage lambda surface display," *Nat Biotechnol* 15(1):74-78 (Jan. 1997).
Langer, "New methods of drug delivery," *Science* 249(4976):1527-1533 (Sep. 28, 1990).
Lathe, "Synthetic oligonucleotide probes deduced from amino acid sequence data. Theoretical and practical considerations," *J Mol Biol* 183(1):1-12 (May 5, 1985).
LeRoith and Helman, "The new kid on the block(ade) of the IDG-1 receptor," *Cancer Cell* 5(3):201-202 (Jan. 2004) *Review. Erratum in: Cancer Cell* 5(4):403 (Apr. 2004).
Liu et al., "Chimeric mouse-human IgG1 antibody that can mediate lysis of cancer cells," *Proc Natl Acad Sci U S A* 84(10):3439-3443 (May 1987).
Liu et al., "Production of a mouse-human chimeric monoclonal antibody to CD20 with potent Fc-dependent biologic activity," *J Immunol* 139(10):3521-3526 (Nov. 15, 1987).
Lu et al., "Simultaneous blockade of both the epidermal growth factor receptor and the insulin-like growth factor receptor signaling pathways in cancer cells with a fully human recombinant bispecific antibody," *J Biol Chem* 279(4):2856-2865 (Jan. 23, 2004).
MacCallum et al., "Antibody-antigen interactions: Contact analysis and binding site topography," *J. Mol. Biol.* 262:732-745 (1996).
Major et al., "Insulin-like growth factors and risk of kidney cancer in men," *British Journal of Cancer* 103(1):132-135 (Jun. 29, 2010).
Maloney et al., "An anti-insulin-like growth factor I receptor antibody that is a potent inhibitor of cancer cell proliferation," *Cancer Res* 63(16):5073-5083-53 (2003).
Mandal et al., "ABGEN: a knowledge-based automated approach for antibody structure modeling," *Nat Biotechnol* 14(3):323-328 (Mar. 1996).
Mao et al., "Phage-display library selection of high-affinity human single-chain antibodies to tumor-associated carbohydrate antigens sialyl Lewisx and Lewisx," *Proc Natl Acad Sci USA* 96(12):6953-6958 (Jun. 8, 1999).
Marasco, "Intrabodies: turning the humoral immune system outside in for intracellular immunization," *Gene Ther* 4(1):11-15 (Jan. 1997).
Marks et al., "Human antibody fragments specific for human blood group antigens from a phage display library," *Biotechnology (NY)* 11(10):1145-1149 (Oct. 1993).
Martin et al., "The affinity-selection of a minibody polypeptide inhibitor of human interleukin-6," *EMBO J.* 13(22):5303-5309 (Nov. 15, 1994).
Maynard and Georgiou, "Antibody Engineering," *Annual Review of Biomedical Engineering* 2:339-379 (2000).
Mendez et al., "Functional transplant of megabase human immunoglobulin loci recapitulates human antibody response in mice," *Nat Genet* 15(2):146-156 (Feb. 1997) *Erratum in: Nat Genet* 16(4):410 (Aug. 1997).

(56) References Cited

OTHER PUBLICATIONS

Miyamoto et al., "Blockade of paracrine supply of insulin-like growth factors using neutralizing antibodies suppresses the liver metastasis of human colorectal cancers," *Clin Cancer Res*, 11(9):3494-3502 (May 1, 2005).

Monfardini et al., "Rational design, analysis, and potential utility of GM-CSF antagonists," *Proc Assoc Am Physicians* 108(6):420-431 (Nov. 1996).

Nyyssönen et al., "Efficient production of antibody fragments by the filamentous fungus *Trichoderma reesei*," *Biotechnology (NY)* 11(5):591-595 (May 1993).

Okayama and Berg, "A cDNA cloning vector that permits expression of cDNA inserts in mammalian cells," *Mol Cell Biol* 3(2):289-290 (Feb. 1983).

Osborn, "Leukocyte adhesion to endothelium in inflammation," *Cell* 62(1):3-6 (Jul. 13, 1990).

Parmley and Smith, "Antibody-selectable filamentous fd phage vectors: affinity purification of target genes," *Gene* 73(2):305-318 (Dec. 20, 1988).

Paul et al., "Transdermal immunization with large proteins by means of ultradeformable drug carriers," *Eur J Immunol* 25(12)3521-3524 (Dec. 1995).

Paul, "Fundamental immunology," Ch. 7 W., ed. $2^{nd}$ ed. *Raven Press N.Y.* (1989).

Pennica et al., "Cloning and expression of human tissue-type plasminogen activator cDNA in *E. coli*," *Nature* 201(5897):214-221 (Jan. 20, 1983).

Peters et al., "Neutrophil migration is defective during recombinant human granulocyte-macrophage colony-stimulating factor infusion after autologous bone marrow transplantation in humans," *Blood* 72(4):1310-1315 (Oct. 1988).

Pinilla et al., "Rapid identification of high affinity peptide ligands using positional scanning synthetic peptide combinatorial libraries," *Biotechniques* 13(6):901-905 (Dec. 1992).

Queen et al., "A humanized antibody that binds to the interleukin 2 receptor," *Proc Natl Acad Sci USA* 86(24):10029-10033 (Dec. 1989).

Restifo et al., "Cancer: Principles and Practice of Oncology," *Lippincot—Raven* 61:3023-3043 (1997).

Rohrmann et al., "Concentrations of IGF-I and IGFBP-3 and brain tumor risk in the European Prospective Investigation into Cancer and Nutrition," *Cancer Epidemiol. Biomarkers Prev.* 20(10):2174-2182 (Oct. 2011).

Rudikoff et al., "Single amino acid substitution altering antigen-binding specificity," *Proc. Natl. Acad. Sci,*. 79(:1979-1983 (Mar. 1982).

Russell et al., "Retroviral vectors displaying functional antibody fragments," *Nucleic Acids Res*. 21(5):1081-1085 (Mar. 11, 1993).

Scott and Smith, "Searching for peptide ligands with an epitope library," *Science* 249(4967):386-390 (Jul. 27, 1990).

Scott, "Discovering peptide ligands using epitope libraries," *Trends Biochem Sci.* 17(7):241-245 (Jul. 1992).

Singh et al., "Structure-based design of a potent, selective, and irreversible inhibitor of the catalytic domain of the erbB receptor subfamily of protein tyrosine kinases," *J Med Chem.* 40(7):1130-1135 (Mar. 28, 1997).

Siraganian et al., "Histamine secretion from mast cells and basophils," *TIPS* 4:432-437 (1983).

Songsivilai and Lachmann, "Bispecific antibody: a tool for diagnosis and treatment of disease," *Clin Exp Immunol* 79(3):315-321 (Mar. 1990).

Suzuki et al., "Complete amino acid sequence of human vitronectin deduced from cDNA. Similarity of cell attachment sites in vitronectin and fibronectin," *EMBO J.* 4:2519-2524 (1985).

Thornton et al., "Protein structure. Prediction of progress at last," *Nature* 354(6349):105-106 (Nov. 14, 1991).

Traunecker et al., "Bispecific single chain molecules (Janusin) target cytotoxic lymphocytes on HIV infected cells," *EMBO J.* 10(12):3655-3659 (Dec. 1991).

Traunecker et al., "Janusin: new molecular design for bispecific reagents," *Int J Cancer Suppl* 5:51-52 (1992).

van Elsas et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," *J Exp Med* 190(3):355-366 (Aug. 2, 1999).

Veber and Freidinger, "The design of metabolically-stable peptide analogs," *TINS* 8:392-396 (1985).

Vitetta et al., "Immunotoxins: magic bullets or misguided missiles," *Immunol Today* 14(6):252-259 (Jun. 1993).

Walter et al., "Cloning of the human estrogen receptor cDNA," *Proc Natl Acad Sci USA* 82(23):7889-7893 (Dec. 1985).

Ward et al., "Binding activities of a repertoire of single immuno-globulin variable domains secreted from *Escherichia coli*," *Nature* 341(6242):544-546 (Oct. 12, 1989).

Windhagen et al., "Modulation of cytokine patterns of human auto reactive T cell clones by a single amino acid substitution of their peptide ligand," *Immunity* 2(4):373-380 (Apr. 1995).

Winter and Harris, "Humanized antibodies," *Immunol Today* 14(6):243-246 (Jun. 1993).

Wright et al., "Genetically engineered antibodies: progress and prospects," *Crit Rev Immunol* 12(3-4):125-168 (1992).

Wu and Bahl, "Synthetic oligodeoxynucleotides for analyses of DNA structure and function," *Prog Nucleic Acid Res Mol Biol* 21:101-141 (1978).

Yu and Rohan, "Role of the insulin-like growth factor family in cancer development and progression," *J Natl Cancer Inst* 92(18):1472-1489 (Sep. 20, 2000).

Zhang, et al, "Identification and characterization of a new cross-reactive human immunodeficiency virus type 1-neutralizing human monoclonal antibody," *J Virol* 78(17):9233-9242 (Sep. 2004).

Zhao et al., "Human monoclonal antibody fragments binding to insulin-like growth factors I and II with picomolar affinity," *Molecular Cancer Therapeutics* 10(9):1535-7163 (Sep. 1, 2011).

FIG. 9

Heavy chain:

```
         10         20         30         40         50         60         70         80
          |          |          |          |          |          |          |          |
QVQLQQPGAEVKKPGSSVKVSCKAS ISWVRQAPGQGLEWMGG NYAQKFQGRVTITADESTSTAY   m708.2 VH
.....L...M............       ...T..VK.           ..........K.....   m708.5 VH 90        100        110        120
          |          |          |          |
MELSSLRSEDTAVYYC WGQGTLVTVSS                                         m708.2 VH
........G......N...........                                         m708.5 VH
```

Light chain:

```
         10         20         30         40         50         60         70         80
          |          |          |          |          |          |          |          |
DIQMTQSPSSLSASVGDRVTIACRAS LNWYQQKPGKAPKLLIY SLQSGVSSRFSGSGSGTEFTLTISSLQP m708.2 VL
..............V..........       ...                 ...........A.........   m708.5 VL 90        100
          |          |
EDFATYFC FGQGTRLEIKR                                                 m708.2 VL
........      .....Q                                                 m708.5 VL
```

Dark: CDR1
Light: CDR2
Middle: CDR3
All CDRs are underlined.

```
                10         20         30         40         50         60         70         80
                 |          |          |          |          |          |          |          |
QVQLQQLGAEVKMPGSSVKVSCKASGGTFSSYAISWVRQAPGQGLEWMGGIIPTLGIVKYAQKFQGRVTITADKSTSTAY m708.5
........P..............I.R..........M..............S...F................... m708.6
........P.........................................S..............E.K..V... m708.7

90        100        110        120
         |          |          |          |
MELSSLGSEDTAVYYCAGGPRGYSYNFDNWGQGTLVTVSS
m708.5
....N..R...................E.S..M......
m708.6
........R..................E.S.........
m708.7
```

VL

```
                10         20         30         40         50         60         70         80
                 |          |          |          |          |          |          |          |
DIQMTQSPSSLSASVGDRVTIVCRASQTISRYVNWYQQKPGKAPKLLIYAASSLQSGVSSRFSGSGSGTEFALTISSLQP m708.5
......I................A.............L..........N..I...................T..... m708.6
.......................A.............L.................................T..... m708.7

90        100
         |          |
EDFATYFCQQTYSPPIIFGQGTRLEIKQ
m708.5
...........................R
m708.6
...........................R
m708.7
```

All CDRs are underlined.

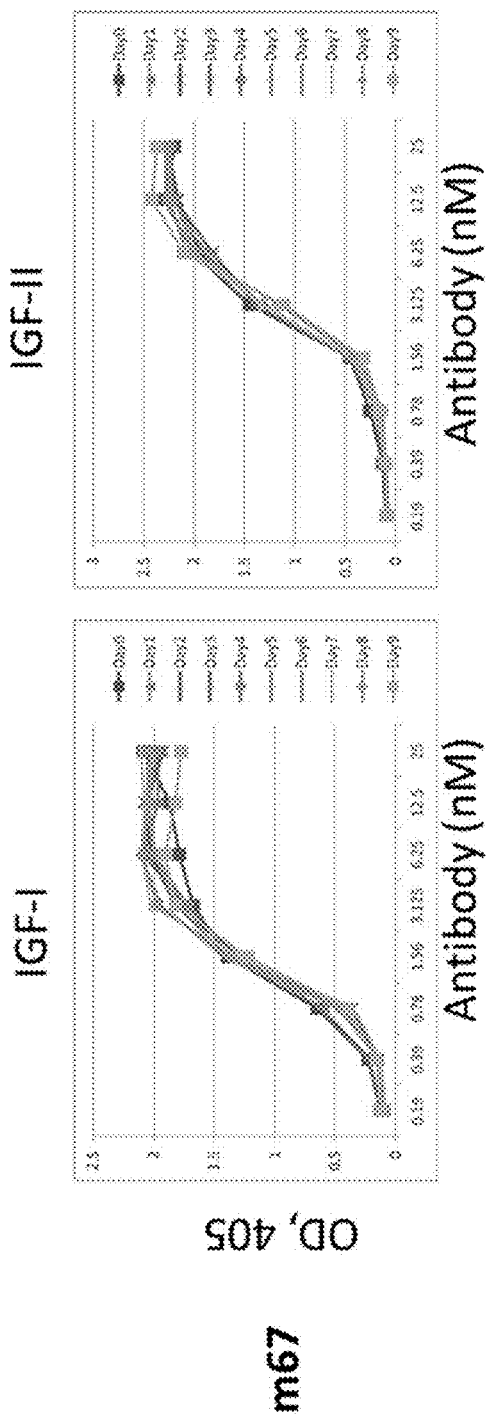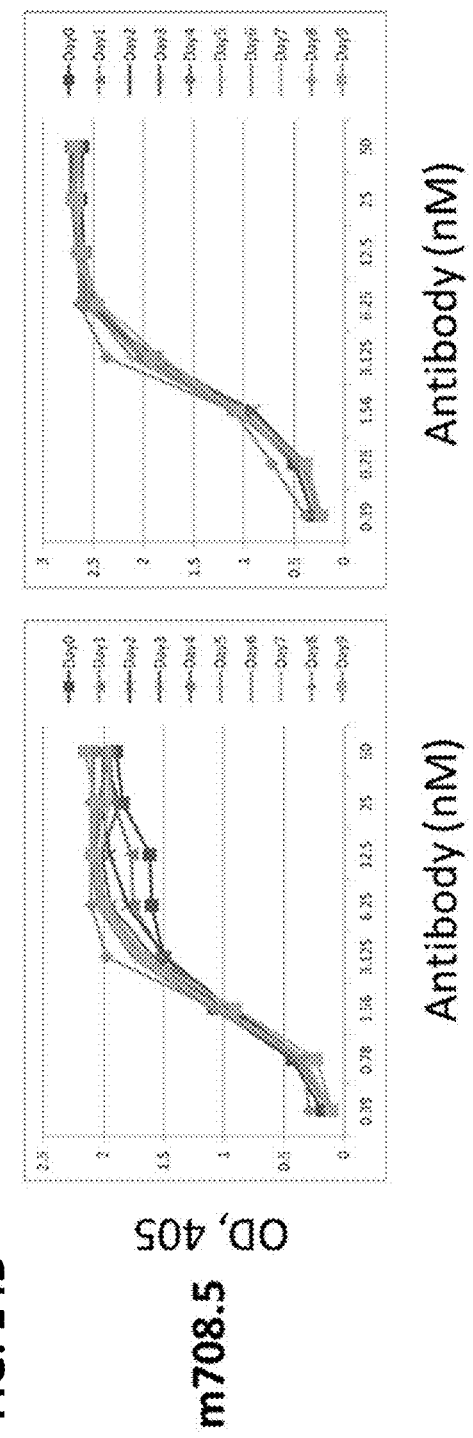
FIG. 14A m67
FIG. 14B m708.5

FIG. 15A  IGF-I
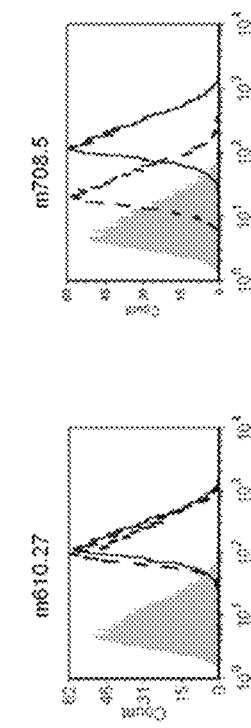
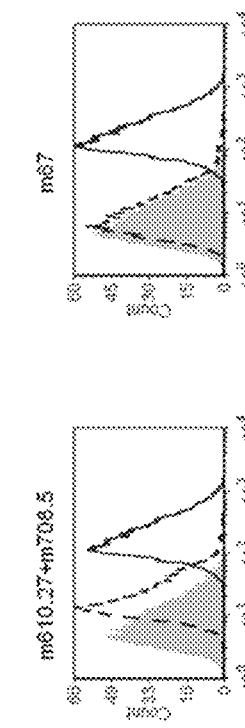
FIG. 15B  IGF-II
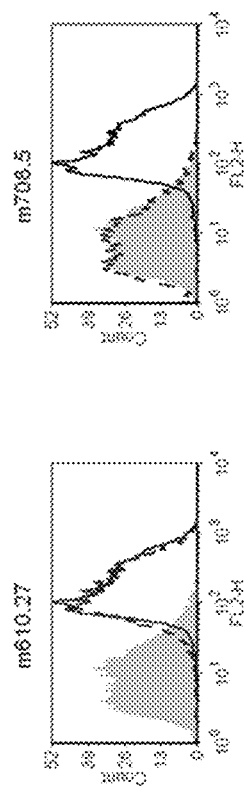
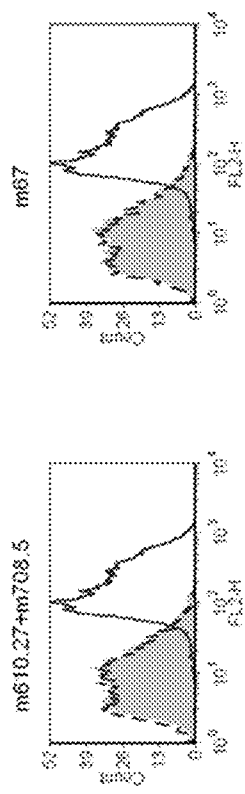

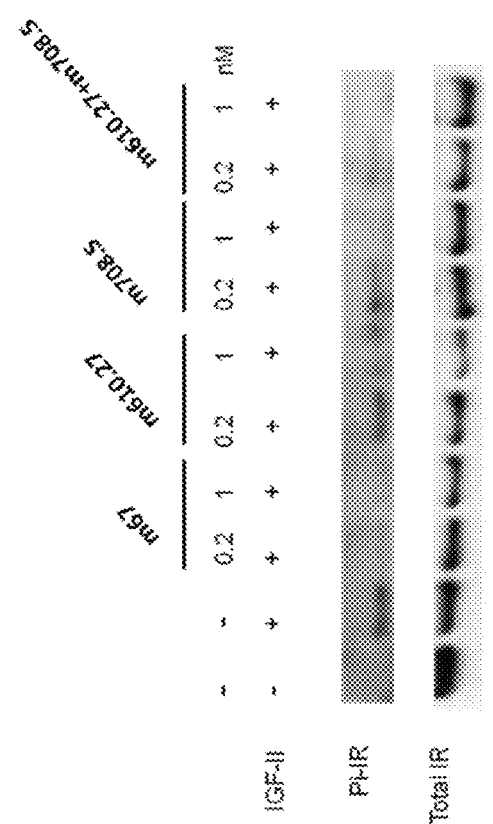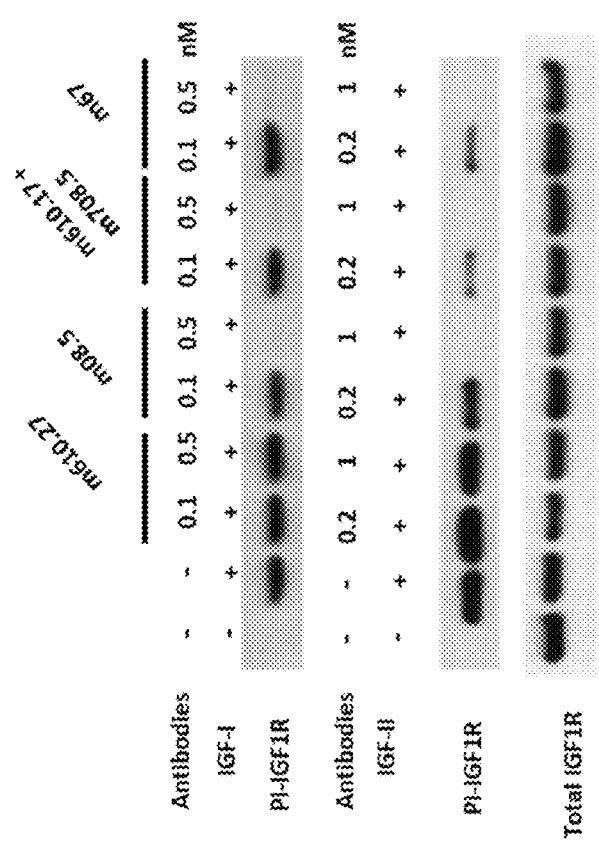
FIG. 18B
FIG. 18A

SEQUENCE LISTING

```
<160> NUMBER OF SEQ ID NOS: 26

<210> SEQ ID NO 1
<211> LENGTH: 22
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Pro Lys Thr
         20                  25                  30
```

<210> SEQ ID NO 3
<211> LENGTH: 165
<212> TYPE: PRT
<213> ORGANISM: Homo sapiens

<400> SEQUENCE: 3

```
Met Thr Ala Pro Ala Ile Lys Ile His Ile Met Ser Ser His Leu
1               5                   10                  15

Phe Tyr Leu Ala Leu Cys Leu Leu Thr Phe Thr Ser Ser Thr Thr Ala
            20                  25                  30

Gly Pro Glu Thr Leu Cys Gly Ala Glu Leu Val Asp Ala Leu Gln Phe
        35                  40                  45

Val Cys Gly Pro Arg Gly Phe Tyr Phe Asn Lys Pro Thr Gly Tyr Gly
    50                  55                  60

Ser Ser Ile Arg Arg Ala Pro Gln Thr Gly Ile Val Asp Glu Cys Cys
65                  70                  75                  80

Phe Arg Ser Cys Asp Leu Arg Arg Leu Glu Met Tyr Cys Ala Pro Leu
                85                  90                  95

Lys Pro Thr Lys Ala Ala Arg Ser Ile Arg Ala Gln Arg His Thr Asp
            100                 105                 110

Met Pro Lys Thr Gln Lys Ser Pro Ser Leu Ser Thr Asn Lys Lys Thr
        115                 120                 125

Lys Leu Gln Arg Arg Arg Lys Gly Glu Pro Lys Thr His Pro Glu Gly
130                 135                 140

Glu Gln Glu Glu Val Thr Glu Ala Thr Arg Lys Ile Arg Gly Pro Arg
145                 150                 155                 160

Glu Lys Arg Leu Gly
                165
```

<210> SEQ ID NO 4
<211> LENGTH: 70
<212> TYPE: PRT
<213> ORGANISM: Homo sapiens

<400> SEQUENCE: 4

```
Phe Thr Ser Ser Thr Thr Ala Gly Pro Glu Thr Leu Cys Gly Ala Glu
1               5                   10                  15

Leu Val Asp Ala Leu Gln Phe Val Cys Gly Pro Arg Gly Phe Tyr Phe
            20                  25                  30

Asn Lys Pro Thr Gly Tyr Gly Ser Ser Ile Arg Arg Ala Pro Gln Thr
        35                  40                  45

Gly Ile Val Asp Glu Cys Cys Phe Arg Ser Cys Asp Leu Arg Arg Leu
    50                  55                  60

Glu Met Tyr Cys Ala Pro
65                  70
```

<210> SEQ ID NO 5
<211> LENGTH: 180
<212> TYPE: PRT
<213> ORGANISM: Homo sapiens

<400> SEQUENCE: 5

```
Met Gly Ile Pro Met Gly Lys Ser Met Leu Val Leu Leu Thr Phe Leu
1               5                   10                  15
```

```
Ala Phe Ala Ser Cys Cys Ile Ala Ala Tyr Arg Pro Ser Glu Thr Leu
             20                  25                  30

Cys Gly Gly Glu Leu Val Asp Thr Leu Gln Phe Val Cys Gly Asp Arg
         35                  40                  45

Gly Phe Tyr Phe Ser Arg Pro Ala Ser Arg Val Ser Arg Arg Ser Arg
 50                  55                  60

Gly Ile Val Glu Glu Cys Cys Phe Arg Ser Cys Asp Leu Ala Leu Leu
 65                  70                  75                  80

Glu Thr Tyr Cys Ala Thr Pro Ala Lys Ser Glu Arg Asp Val Ser Thr
                 85                  90                  95

Pro Pro Thr Val Leu Pro Asp Asn Phe Pro Arg Tyr Pro Val Gly Lys
             100                 105                 110

Phe Phe Gln Tyr Asp Thr Trp Lys Gln Ser Thr Gln Arg Leu Arg Arg
         115                 120                 125

Gly Leu Pro Ala Leu Leu Arg Ala Arg Arg Gly His Val Leu Ala Lys
 130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                 165                 170                 175

Ser Asn Arg Lys
            180

<210> SEQ ID NO 6
<211> LENGTH: 67
<212> TYPE: PRT
<213> ORGANISM: Homo sapiens

<400> SEQUENCE: 6

Ala Tyr Arg Pro Ser Glu Thr Leu Cys Gly Gly Glu Leu Val Asp Thr
 1               5                  10                  15

Leu Gln Phe Val Cys Gly Asp Arg Gly Phe Tyr Phe Ser Arg Pro Ala
             20                  25                  30

Ser Arg Val Ser Arg Arg Ser Arg Gly Ile Val Glu Glu Cys Cys Phe
         35                  40                  45

Arg Ser Cys Asp Leu Ala Leu Leu Glu Thr Tyr Cys Ala Thr Pro Ala
 50                  55                  60

Lys Ser Glu
 65

<210> SEQ ID NO 7
<211> LENGTH: 120
<212> TYPE: PRT
<213> ORGANISM: homo sapiens
<220> FEATURE:
<221> NAME/KEY: MISC_FEATURE
<222> LOCATION: (7)..(7)
<223> OTHER INFORMATION: Xaa = L or P
<220> FEATURE:
<221> NAME/KEY: MISC_FEATURE
<222> LOCATION: (20)..(20)
<223> OTHER INFORMATION: Xaa = V or I
<220> FEATURE:
<221> NAME/KEY: MISC_FEATURE
<222> LOCATION: (23)..(23)
<223> OTHER INFORMATION: Xaa = K or R
<220> FEATURE:
<221> NAME/KEY: MISC_FEATURE
<222> LOCATION: (37)..(37)
<223> OTHER INFORMATION: Xaa = V or M
<220> FEATURE:
<221> NAME/KEY: MISC_FEATURE
```

<222> LOCATION: (56)..(56)
<223> OTHER INFORMATION: Xaa = G or S
<220> FEATURE:
<221> NAME/KEY: MISC_FEATURE
<222> LOCATION: (61)..(61)
<223> OTHER INFORMATION: Xaa = A or S
<220> FEATURE:
<221> NAME/KEY: MISC_FEATURE
<222> LOCATION: (62)..(62)
<223> OTHER INFORMATION: Xaa = Q or P
<220> FEATURE:
<221> NAME/KEY: MISC_FEATURE
<222> LOCATION: (74)..(74)
<223> OTHER INFORMATION: Xaa = K or E
<220> FEATURE:
<221> NAME/KEY: MISC_FEATURE
<222> LOCATION: (76)..(76)
<223> OTHER INFORMATION: Xaa = T or K
<220> FEATURE:
<221> NAME/KEY: MISC_FEATURE
<222> LOCATION: (77)..(77)
<223> OTHER INFORMATION: Xaa = S or G
<220> FEATURE:
<221> NAME/KEY: MISC_FEATURE
<222> LOCATION: (79)..(79)
<223> OTHER INFORMATION: Xaa = A or V
<220> FEATURE:
<221> NAME/KEY: MISC_FEATURE
<222> LOCATION: (85)..(85)
<223> OTHER INFORMATION: Xaa = S or N
<220> FEATURE:
<221> NAME/KEY: MISC_FEATURE
<222> LOCATION: (87)..(87)
<223> OTHER INFORMATION: Xaa = G or R
<220> FEATURE:
<221> NAME/KEY: MISC_FEATURE
<222> LOCATION: (109)..(109)
<223> OTHER INFORMATION: Xaa = N or E
<220> FEATURE:
<221> NAME/KEY: MISC_FEATURE
<222> LOCATION: (111)..(111)
<223> OTHER INFORMATION: Xaa = G or S
<220> FEATURE:
<221> NAME/KEY: MISC_FEATURE
<222> LOCATION: (115)..(115)
<223> OTHER INFORMATION: Xaa = L or M

<400> SEQUENCE: 7

Gln Val Gln Leu Gln Gln Xaa Gly Ala Glu Val Lys Met Pro Gly Ser
 1               5                  10                  15

Ser Val Lys Xaa Ser Cys Xaa Ala Ser Gly Gly Thr Phe Ser Ser Tyr
            20                  25                  30

Ala Ile Ser Trp Xaa Arg Gln Ala Pro Gly Gln Gly Leu Glu Trp Met
        35                  40                  45

Gly Gly Ile Ile Pro Thr Leu Xaa Ile Val Lys Tyr Xaa Xaa Lys Phe
50                  55                  60

Gln Gly Arg Val Thr Ile Thr Ala Asp Xaa Ser Xaa Xaa Thr Xaa Tyr
65                  70                  75                  80

Met Glu Leu Ser Xaa Leu Xaa Ser Glu Asp Thr Ala Val Tyr Tyr Cys
                85                  90                  95

Ala Gly Gly Pro Arg Gly Tyr Ser Tyr Asn Phe Asp Xaa Trp Xaa Gln
            100                 105                 110

Gly Thr Xaa Val Thr Val Ser Ser
        115                 120

<210> SEQ ID NO 8
<211> LENGTH: 108
<212> TYPE: PRT
<213> ORGANISM: homo sapiens
<220> FEATURE:

```
<221> NAME/KEY: MISC_FEATURE
<222> LOCATION: (4)..(4)
<223> OTHER INFORMATION: Xaa = M or I
<220> FEATURE:
<221> NAME/KEY: MISC_FEATURE
<222> LOCATION: (22)..(22)
<223> OTHER INFORMATION: Xaa = V or A
<220> FEATURE:
<221> NAME/KEY: MISC_FEATURE
<222> LOCATION: (33)..(33)
<223> OTHER INFORMATION: Xaa = V or L
<220> FEATURE:
<221> NAME/KEY: MISC_FEATURE
<222> LOCATION: (53)..(53)
<223> OTHER INFORMATION: Xaa = S or N
<220> FEATURE:
<221> NAME/KEY: MISC_FEATURE
<222> LOCATION: (58)..(58)
<223> OTHER INFORMATION: Xaa = V or I
<220> FEATURE:
<221> NAME/KEY: MISC_FEATURE
<222> LOCATION: (72)..(72)
<223> OTHER INFORMATION: Xaa = A or T
<220> FEATURE:
<221> NAME/KEY: MISC_FEATURE
<222> LOCATION: (108)..(108)
<223> OTHER INFORMATION: Xaa = Q or R

<400> SEQUENCE: 8

Asp Ile Gln Xaa Thr Gln Ser Pro Ser Ser Leu Ser Ala Ser Val Gly
1               5                   10                  15

Asp Arg Val Thr Ile Xaa Cys Arg Ala Ser Gln Thr Ile Ser Arg Tyr
            20                  25                  30

Xaa Asn Trp Tyr Gln Gln Lys Pro Gly Lys Ala Pro Lys Leu Leu Ile
        35                  40                  45

Tyr Ala Ala Ser Xaa Leu Gln Ser Gly Xaa Ser Ser Arg Phe Ser Gly
50                  55                  60

Ser Gly Ser Gly Thr Glu Phe Xaa Leu Thr Ile Ser Ser Leu Gln Pro
65                  70                  75                  80

Glu Asp Phe Ala Thr Tyr Phe Cys Gln Gln Thr Tyr Ser Pro Pro Ile
                85                  90                  95

Thr Phe Gly Gln Gly Thr Arg Leu Glu Ile Lys Xaa
            100                 105

<210> SEQ ID NO 9
<211> LENGTH: 120
<212> TYPE: PRT
<213> ORGANISM: homo sapiens

<400> SEQUENCE: 9

Gln Val Gln Leu Gln Gln Pro Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
50                  55                  60

Gln Gly Arg Val Thr Ile Thr Ala Asp Glu Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Arg Gly Tyr Ser Tyr Asn Phe Asp Tyr Trp Gly Gln
            100                 105                 110
```

Gly Thr Leu Val Thr Val Ser Ser
        115                 120

<210> SEQ ID NO 10
<211> LENGTH: 108
<212> TYPE: PRT
<213> ORGANISM: homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Thr Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Ser Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Thr Tyr Ser Pro Pro Ile
                85                  90                  95

Thr Phe Gly Gln Gly Thr Arg Leu Glu Ile Lys Arg
            100                 105

<210> SEQ ID NO 11
<211> LENGTH: 360
<212> TYPE: DNA
<213> ORGANISM: homo sapiens

<400> SEQUENCE: 11
caggtacagc tgcagcaact aggggctgaa gtgaagatgc ctgggtcctc ggtgaaggtc      60
tcctgcaagg cttctggagg caccttcagt agttatgcta tcagctgggt gcgacaggcc    120
cctggacaag ggcttgagtg gatgggaggg atcatcccta cccttggtat agtaaagtac    180
gcgcagaagt tccagggcag agtcacgatt accgcggaca atccacgag cacagcctac     240 atggagctga gcagcctggg atctgaggac acggccgtgt attactgtgc gggaggccct    300 agggatca gctataactt tgacaactgg ggtcagggca ccctggtcac cgtctcctca      360

<210> SEQ ID NO 12
<211> LENGTH: 324
<212> TYPE: DNA
<213> ORGANISM: homo sapiens

<400> SEQUENCE: 12
gacatccaaa tgacccagtc tccatcctcc ctgtctgcat ctgtaggaga cagagtcacc      60
atcgtttgcc gggcaagtca gaccattagt aggtatgtaa attggtatca gcagaaacca    120
gggaaagccc ctaagctcct gatctatgct gcatccagtt tgcaaagtgg ggtctcatca    180
aggttcagtg gtagtggatc agggacagag ttcgctctca ccatcagcag tctgcagcct    240
gaagattttg caacttattt ctgtcaacag acttacagtc ccccgatcac cttcggccaa    300
gggacacgac tggagattaa acaa                                            324

<210> SEQ ID NO 13
<211> LENGTH: 360
<212> TYPE: DNA
<213> ORGANISM: homo sapiens

<400> SEQUENCE: 13

```
caggtacagc tgcagcagcc aggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatccta tccttggtat agcaaactac      180
gcacagaagt tccagggcag agtcacgatt accgcggacg aatccacgag cacagcctac    240
atggagctga gcagcctgag atctgaggac acggccgtgt attactgtgc gagaggccct    300 agggggataca gctataactt tgactactgg ggccagggca ccctggtcac cgtctcctca    360
```

<210> SEQ ID NO 14
<211> LENGTH: 324
<212> TYPE: DNA
<213> ORGANISM: homo sapiens

<400> SEQUENCE: 14

```
gacatccaga tgacccagtc tccatcctcc ctgtctgcat ctgtaggaga cagagtcacc      60
atcgcttgcc gggcaagtca gaccattagt aggtatttaa attggtatca gcagaaacca    120
gggaaagccc ctaagctcct gatctatgct gcatccagtt tgcaaagtgg ggtctcatca    180
aggttcagtg gcagtggatc tgggacagag ttcactctca ccatcagcag tctgcagcct    240
gaagattttg caacttattt ctgtcaacag acttacagtc ccccgatcac cttcggccaa    300
gggacacgac tggagattaa acga                                           324
```

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 15

```
gatatatcca tggcccaggc ggcc                                             24
```

<210> SEQ ID NO 16
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 16

```
accactagtt gggccggcct g                                                21
```

<210> SEQ ID NO 17
<211> LENGTH: 54
<212> TYPE: DNA
<213> ORGANISM: Artificial sequence
<220> FEATURE:
<223> OTHER INFORMATION: Oligonucleotide primer

<400> SEQUENCE: 17

```
cttcgctgtt tttcaatatt ttctgttatt gcttcagttt tggcccaggc ggcc             54
```

<210> SEQ ID NO 18
<211> LENGTH: 56
<212> TYPE: DNA
<213> ORGANISM: Artificial sequence
<220> FEATURE:
<223> OTHER INFORMATION: Oligonucleotide primer

<400> SEQUENCE: 18

```
gagccgccac cctcagaacc gccaccctca gagccaccac tagttgggcc ggcctg          56
```

<210> SEQ ID NO 19
<211> LENGTH: 360
<212> TYPE: DNA
<213> ORGANISM: Homo sapiens

<400> SEQUENCE: 19

```
caggtacagt tgcaacaacc aggggctgaa gtgaagatgc ctgggtcctc ggtgaaggtc      60
tcctgcaagg cttctggagg caccttcagc agctatgcta tcagctggat gcgacaggcc    120
cctggacaag gcttgagtg gatgggtggg atcatcccta cccttagtat agtaaagtac     180
gcaccgaagt tccagggcag agtcacgatt accgcagaca atccacggg cacagcctac     240
atggagctga gcaacctgag atctgaggac acggccgtgt attactgtgc gggaggccct    300
aggggataca gctataactt tgacgaatgg agtcagggca ccatggtcac cgtctcctca    360
```

<210> SEQ ID NO 20
<211> LENGTH: 324
<212> TYPE: DNA
<213> ORGANISM: Homo sapiens

<400> SEQUENCE: 20

```
gacatccaga tgacccagtc tccatcctcc ctgtctgcat ctgtaggaga cagagtcacc      60
atcgcttgcc gggcaagtca gaccattagt aggtatttaa attggtatca gcagaaacca    120
gggaaagccc ctaagctcct gatctatgct gcaaccagtt tgcaaagtgg ggtctcatca    180
aggttcagtg gcagtggatc tgagacagag ttcactctca ccatcagcag tctgcagcct    240
gaagattttg caacttattt ctgtcaacag acttacagtc ccccgatcac cttcggccaa    300
gggacacgat tggagattaa acga                                            324
```

<210> SEQ ID NO 21
<211> LENGTH: 360
<212> TYPE: DNA
<213> ORGANISM: Homo sapiens

<400> SEQUENCE: 21

```
caggtacagt tgcagcaacc aggggctgaa gtgaagatgc ctgggtcctc ggtgaagatc      60
tcctgtaggg cttctggagg caccttcagc agctatgcta tcagctgggt gcgtcaggcc    120
cctggacaag gcttgagtg gatgggaggg atcatcccta cccttggtat agtaaagtac     180
tcacagaagt tccagggcag agtcacgatt accgcggacg aatccaagag cacagtctac    240
atggaactga gcagcctgag atctgaggac acggccgtgt attattgtgc gggaggccct    300
aggggataca gctataactt tgacgaatgg agtcagggca ccctggtcac cgtctcctca    360
```

<210> SEQ ID NO 22
<211> LENGTH: 324
<212> TYPE: DNA
<213> ORGANISM: Homo sapiens

<400> SEQUENCE: 22

```
gacatccaga tgacccagtc tccatcctcc ctgtctgcat ctgtaggaga cagagtcacc      60
atcgcttgcc gggcaagtca gaccattagt aggtatttaa attggtatca gcagaaacca    120
gggaaagccc ctaagctcct gatctatgct gcatccaatt tgcaaagtgg gatatcatca    180
aggttcagtg gcagtggatc tgggacagag ttcactctca ccatcagcag tctgcagcct    240
```

```
gaagattttg caacttattt ctgtcaacag acttatagtc ccccgatcac cttcggtcaa    300
gggacacgac tggagattaa acga                                           324
```

<210> SEQ ID NO 23
<211> LENGTH: 120
<212> TYPE: PRT
<213> ORGANISM: homo sapiens

<400> SEQUENCE: 23

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Arg Leu Arg Ser Asp Asp Thr Ala Val Tyr Tyr Cys
                85                  90                  95

Ala Arg Asp Val Gln Trp Leu Ala Tyr Gly Met Asp Val Trp Gly Gln
            100                 105                 110

Gly Thr Thr Val Thr Val Ser Ser
        115                 120
```

<210> SEQ ID NO 24
<211> LENGTH: 107
<212> TYPE: PRT
<213> ORGANISM: homo sapiens

<400> SEQUENCE: 24

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Arg Ala Pro Asp Leu Leu Ile
        35                  40                  45

Asn Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Leu Pro Phe
                85                  90                  95

Thr Phe Gly Gly Gly Thr Lys Val Glu Ile Lys
            100                 105
```

<210> SEQ ID NO 25
<211> LENGTH: 1350
<212> TYPE: DNA
<213> ORGANISM: Homo sapiens

<400> SEQUENCE: 25

```
caagtgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag ggcttgagtg gatgggaata atcaacccta gtggtggtag cacaagctac   180
```

```
gcacagaagt tccagggcag agtcaccatg accagggaca cgtccacgag cacagtctac      240
atggagctga gcaggctgag atctgacgac acggccgtgt attactgtgc gagagatgtg      300
cagtggctgg catacggtat ggacgtctgg ggccaaggga ccacggtcac cgtgagctca      360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagaa agttgagccc      660
aaatcttgtg acaaaactca cacatgccca ccgtgcccag cacctgaact cctggggggga     720 ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacaac      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtacaccc tgcccccatc ccgggatgag     1080
ctgaccaaga accaggtcag cctgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctac agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa                                      1350

<210> SEQ ID NO 26
<211> LENGTH: 641
<212> TYPE: DNA
<213> ORGANISM: Homo sapiens

<400> SEQUENCE: 26
gacatccaga tgacccagtc tccatcctcc ctgtctgcat ctgtaggaga cagagtcacc       60
atcacttgcc gggcaagtca gagcattagt agctatttaa attggtatca gcagaagcca      120
gggagagccc ctgacctcct gatcaatgct gcatccagtt tgcaaagtgg ggtcccatca      180
aggttcagtg gcagtggatc tgggaccgac ttcactctca ccatcagcag tctccaacct      240
gaagattttg caacttactt ctgtcaacag agttacagtc ttccgttcac tttcggcgga      300
gggaccaagg tggagatcaa aggaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag cacccctgacg     540 ctgagcaaag cagactacga aaacacaaa gtctacgcct gcgaagtcac ccatcagggc      600
ctgagctcgc ccgtcacaaa gagcttcaac aggggagagt g                         641
```

HUMAN MONOCLONAL ANTIBODIES THAT BIND INSULIN-LIKE GROWTH FACTOR (IGF) I AND II

CROSS REFERENCE TO RELATED APPLICATION

This is a continuation of U.S. patent application Ser. No. 14/111,507, filed Oct. 11, 2013, which is the U.S. national stage of PCT Application No. PCT/US2012/033128, filed Apr. 11, 2012, which was published in English under PCT Article 21(2), which claims the benefit of U.S. Provisional Application No. 61/474,664, filed Apr. 12, 2011, and the benefit of U.S. Provisional Application No. 61/548,164, filed Oct. 17, 2011. The prior applications are all incorporated by reference.

FIELD

This application relates to the field of antibodies, specifically to human antibodies that specifically bind insulin-like growth factor (IGF)-I and IGF-II, and their use.

BACKGROUND

The insulin-like growth factor-I receptor (IGF-IR) and its ligands (IGF-I and IGF-II) have been implicated in a variety of physiologic processes and in pathologic conditions such as cancer (see, for example, Pollack et al., Nat Rev Cancer, 2008. 8(12): p. 915-28). Although the role of the IGF system in cancer has been recognized many years ago, it is not until recently that the system's components have been targeted and shown to affect cell transformation, proliferation, survival, motility, and migration in tissue cultures and in mouse models of cancer (see, for example, Wang et al., Curr Cancer Drug Targets, 2002. 2(3): p. 191-207). The IGF-mediated signaling is initiated by binding of either IGF-I or IGF-II to their receptor (IGF-IR). Then phosphorylated IGF-IR recruits adaptor proteins, such as insulin receptor substrate (IRS) 1, IRS2 and Src-Homology Collagen (SHC) (Feng et al., Curr Opin Drug Discov Devel, 2008. 11(2): p. 178-85) Mechanistic studies have shown that ligand mediates the stimulation of IGF-IR, inducing receptor clustering and autophosphorylation followed by transphosphorylation of the β subunits (Hernandez-Sanchez et al., J Biol Chem, 1995. 270(49): p. 29176-81). The phosphorylation of IRS1 regulates the activity of phosphoinositide 3-kinase and protein kinase B (also known as Akt) and triggers transcription factors which control the expression of many genes that are important for cell proliferation and growth (Foulstone et al., J Pathol, 2005. 205(2): p. 145-53). Numerous studies demonstrated that IGF-IR is expressed in a broad panel of tumors, suggesting that inhibition of IGF-IR signaling may have both proapoptotic and antiproliferative consequences (Zha et al., Mol Cancer Ther., 2009. 8(8): p. 2110-21). Thus, it has been proposed that modulation of the activity of the IGF system could add to the arsenal of anticancer therapeutic approaches (Feng et al., Mol. Cancer. Ther., 2006. 5(1): p. 114-20). A number of epidemiologic studies have shown consistently that high circulating levels of a potent mitogen, insulin-like growth factor (IGF)-I, are associated with increased risk for several common cancers, including those of the breast, prostate, lung, and colorectum. The level of IGF-binding protein (IGFBP)-3, a major IGF-I-binding protein in serum that, in most situations, suppresses the mitogenic action of IGF-I, is inversely associated with the risk of these cancers.

There is increasing epidemiological evidence to link elevated plasma IGF-I level with prostate, breast, and colon cancer risk. Breast cancer tissues from patients exhibit higher IGFR1 expression than adjacent normal tissue, suggesting a link between IGFR1 and breast epithelial cell transformation. It has been reported that the transformation capacity of tumor cells is attenuated when IGFR1 is inhibited using an antisense strategy, neutralizing antibody (anti-IR3 or anti-IGF-I) or dominant negative truncation of the receptor (see Hailey, J. et al, Molecular Cancer Therapeutics 1: 1349-1353, 2002; Maloney E. K., et al, Cancer Res. 63: 5073-5083, 2003; Burtrum D., et al, Cancer Res., 63: 8912-8921, 2003; u et al., J. Biol. Chem. 279: 2856-2865, 2004; Miyamoto et al., Clin. Cancer Res. 11: 3494-3502, 2005; Goya et al., Cancer Research 64: 6252-6258, 2004). However, a need exists in the art for improved multi-target therapies to treat neoplastic disease and metastatic cancers.

SUMMARY

Disclosed herein are human monoclonal antibodies that specifically bind both IGF-I and IGF-II with picomolar affinity and potently inhibit the IGF-IR signal transduction function. These antibodies are active in both an IgG and a scFv format. In some embodiments, the monoclonal human antibodies specifically bind insulin-like growth factor II (IGF-II) with an equilibrium dissociation constant ($K_d$) of 200 pM or less and specifically bind IGF-I with an equilibrium dissociation constant ($K_d$) of 200 pM or less, and inhibits phosphorylation of the insulin-like growth factor receptor. In one specific non-limiting example, the human monoclonal antibody binds IGF-I with an equilibrium constant ($K_d$) of 200 pM and IGF-II with an equilibrium constant ($K_d$) of 60 pM. In additional embodiments, the monoclonal human antibody inhibits the motility of breast cancer cells in vitro. Bispecific forms of these antibodies are also disclosed.

In further embodiments, the heavy chain variable region of the antibody includes the amino acid sequence set forth as amino acids 26-33 of SEQ ID NO: 7, amino acids 51-58 of SEQ ID NO: 7, and/or amino acids 97-109 of SEQ ID NO: 7. In yet other embodiments, the light chain variable region of the antibody includes the amino acid sequence set forth as amino acids 27-32 of SEQ ID NO: 8, amino acids 50-52 of SEQ ID NO: 8 and/or amino acids 89-97 of SEQ ID NO: 8. The antibodies can include the framework regions included in one or more of SEQ ID NOs: 7-10.

Nucleic acids encoding these antibodies, vectors including these nucleic acids, and host cells transformed with these vectors are also disclosed herein. Also disclosed are pharmaceutical compositions comprising these antibodies, nucleic acids and vectors.

In some embodiments, methods are provided for treating a subject with cancer. These methods include administering to the subject a therapeutically effective amount of the monoclonal antibodies, nucleic acids and/or vectors, thereby treating the subject.

Methods are also disclosed for diagnosing cancer in a subject. These methods include contacting a sample from the subject with an isolated monoclonal antibody that specifically binds both IGF-I and IGF-II with picomolar affinity, and detecting binding of the isolated monoclonal antibody to the sample. An increase in the binding of the antibody to the sample as compared to a control indicates that the subject has cancer.

In additional embodiments, methods are provided for inhibiting phosphorylation of the insulin-like growth factor-I receptor. These methods include contacting a cell with an effective amount of the isolated monoclonal antibody that specifically binds both IGF-I and IGF-II with picomolar affinity, thereby inhibiting the phosphorylation of the insulin-like growth factor receptor.

The foregoing and other features and advantages will become more apparent from the following detailed description of several embodiments, which proceeds with reference to the accompanying figures.

BRIEF DESCRIPTION OF THE FIGURES

FIG. 9 is an alignment showing a comparison of the m708.5 heavy chain (SEQ ID NO: 7) with m708.2 heavy chain (SEQ ID NO: 9) and a comparison of the m708.5 light chain (SEQ ID NO: 8) with the m708.2 light chain (SEQ ID NO: 10). The positions (amino acid numbers) are shown above the sequences. CDRs are highlighted; framework regions are not highlighted. For m708.5, H-CDR1 is amino acids 26-33 of SEQ ID NO: 7, H-CDR2 is amino acids 51-58 of SEQ ID NO: 7, and H-CDR3 is amino acids 97-109 of SEQ ID NO: 7, L-CDR1 is amino acids 27-32 of SEQ ID NO: 8, L-CDR2 is amino acids 50-52 of SEQ ID NO: 8, and L-CDR3 is amino acids 89-97 of SEQ ID NO: 8. Thus, amino acids 1-25, amino acids 34-50, amino acids 59-96 and amino acids 110-120 of SEQ ID NO: 7 and SEQ ID NO: 9 are heavy chain framework regions Amino acids 1-26, amino acids 33-49, amino acids 53-88 and amino acids 98-108 of SEQ ID NO: 8 and SEQ ID NO: 10 are light chain framework regions.

FIG. 10 is an alignment showing a comparison of the m708.5 heavy chain with the m708.6 heavy chain and the m708.7 heavy chain and a comparison of the m708.5 light chain with the m708.6 light chain. The heavy chain amino acid sequences are all encompassed by the consensus sequence amino acid set forth as SEQ ID NO: 7. The light chain amino acid sequences are all encompassed by the consensus amino acid sequence set forth as SEQ ID NO: 8.

(FIG. 12A) IGF-II was directly coated on the ELISA plate. Bound scFv m610 was detected by HRP-conjugated anti-Flag antibody in the presence of antibody competitors (IgG1 m708.5 or IgG1 m102.4. (FIG. 12B) IgG1 m610.27 was coated on the ELISA plate and IGF-II was captured by coated IgG1 m610.27. Bound scFv m708.5 or VH m630.3 was detected by HRP-conjugated anti-Flag tag antibody.

(FIG. 13A) IgG1 m708.5 or the mixture of IgG1 m610 and IgG1 m708.5 plus IGF-II was analyzed by Superdex G75 column. (FIG. 13B) m67, the mixture of m67 and IGF-II, or the mixture of m67/IGF-II plus IGF-I was analyzed by Superdex G200 column.

FIGS. 14A and 14B are graphs showing stabilization of m67 and m708.5 in Human Sera. Bispecific antibody (BsAb) m67 (FIG. 14A) and IgG1 m708.5 (FIG. 14B) were incubated with equal volume of human sera at 37° C. for 9 days and then tested to bind to IGF-I and IGF-II by ELISA.

FIGS. 15A and 15B are graphs showing binding Inhibition of IGF-I (FIG. 15A) and IGF-II (FIG. 15B) on MCF7 Cells. MCF-7 cells were incubated with 5 nM biotinylated IGF-I or 1 nM biotinylated IGF-II in the absence or presence of antibodies. Bound biotinylated IGF-I or IGF-II was detected by streptavidin-PE. Blank cells incubated with streptavidin-PE conjugate only are in grey. Cells incubated with IGF-I or IGF-II only are shown by a solid line. Those for IGF-I or IGF-II with antibodies are shown with a dashed line.

FIGS. 18A and 18B are a set of digital images showing inhibition of IGF1R and IR phosphorylation. MCF-7 cells were starved in serum free medium for 5 hours first, followed by addition of treatment medium with 1 nM IGF-I or 5 nM IGF-II with the indicated concentrations of antibodies. Thirty minutes later cells were chilled and lysed. (FIG. 18A) IGF1R was immunoprecipitated and the phosphorylated IGF1R was detected with a phosphor-tyrosine specific antibody. The total amount of IGF1R were detected by the same polyclonal antibody used for the immunoprecipitation. (FIG. 18B) IR was immunoprecipitated and detected as following above methods.

SEQUENCE LISTING

Figure 1:
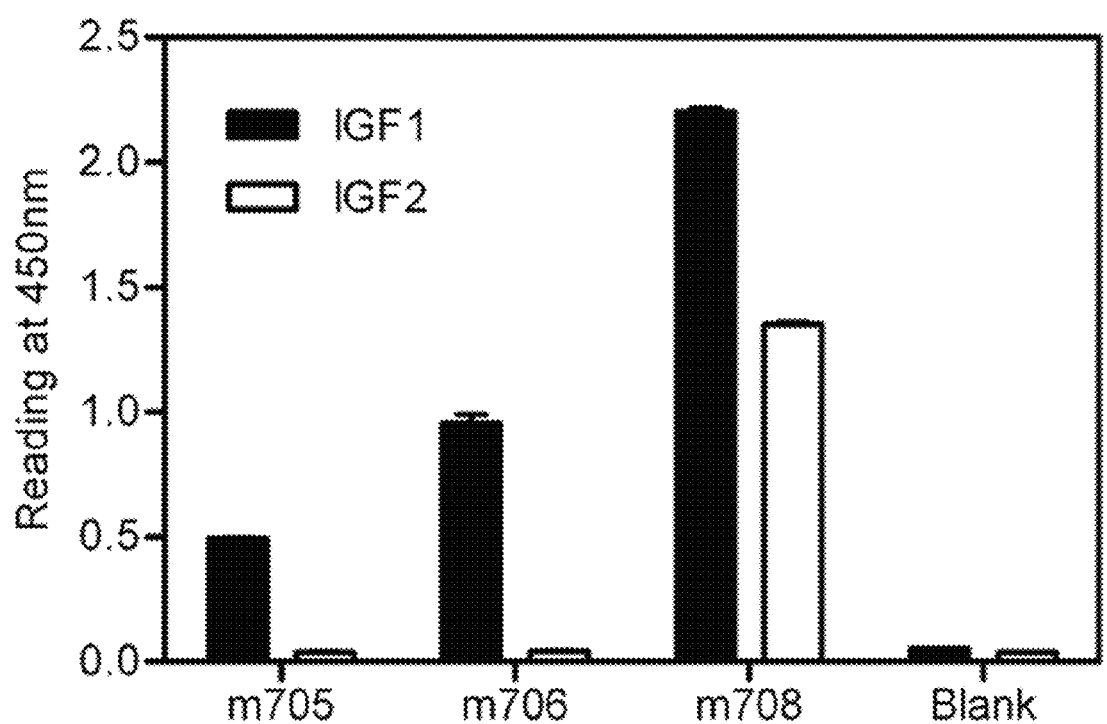
FIG. 1 is a bar graph illustrating binding of Fab m705, 6, 8 to IGF-I,-II as measured by ELISA. Fabs were added to wells coated with IGF-I (black) and IGF-II (white). Bound Fabs were detected with a mouse anti-Flag tag antibody and measured as optical densities at 450 nm.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [4239-86603-04_Sequence_Listing.txt, Aug. 21, 2015, 20.8 KB], which is incorporated by reference herein.

SEQ ID NO: 1 is an exemplary amino acid sequence of a human insulin chain A.

SEQ ID NO: 2 is an exemplary amino acid sequence of a human insulin chain B.

SEQ ID NO: 3 is an exemplary amino acid sequence of an IGF-I precursor.

SEQ ID NO: 4 is an exemplary amino acid sequence of a mature IGF-I.

SEQ ID NO: 5 is an exemplary amino acid sequence of an IGF-II precursor.

SEQ ID NO: 6 is an exemplary amino acid sequence of a mature IGF-II.

SEQ ID NO: 7 is the amino acid sequence of a consensus sequence, which encompasses human monoclonal antibody clone m708.5, m708.6 and m708.7 heavy chain.

SEQ ID NO: 8 is the amino acid sequence of a consensus sequence, which encompasses human monoclonal antibody clone m708.5, m708.6 and m708.7 light chain.

SEQ ID NO: 9 is the amino acid sequence of human monoclonal antibody clone m708.2 heavy chain.

SEQ ID NO: 10 is the amino acid sequence of human monoclonal antibody clone m708.2 light chain.

SEQ ID NO: 11 is a nucleic acid sequence encoding human monoclonal antibody clone m708.5 heavy chain.

SEQ ID NO: 12 is a nucleic acid sequence encoding human monoclonal antibody clone m708.5 light chain.

SEQ ID NO: 13 is a nucleic acid sequence encoding human monoclonal antibody clone m708.2 heavy chain.

SEQ ID NO: 14 is a nucleic acid sequence encoding human monoclonal antibody clone m708.2 light chain.

SEQ ID NOs: 15-18 are the nucleic acid sequences of primers.

SEQ ID NO: 19 is the nucleic acid sequence encoding human monoclonal antibody clone m708.6 heavy chain.

SEQ ID NO: 20 is the nucleic acid sequence encoding human monoclonal antibody clone m708.6 light chain.

SEQ ID NO: 21 is the nucleic acid sequence encoding human monoclonal antibody clone m708.7 heavy chain.

SEQ ID NO: 22 is the nucleic acid sequence encoding human monoclonal antibody clone m708.7 light chain.

SEQ ID NO: 23 is the amino acid sequence of the m610.27 heavy chain.

SEQ ID NO: 24 is the amino acid sequence of the m610.27 light chain.

SEQ ID NO: 25 is a nucleic acid sequence encoding the m610.27 heavy chain.

SEQ ID NO: 26 is a nucleic acid sequence encoding the m610.27 light chain.

DETAILED DESCRIPTION

Disclosed herein are human monoclonal antibodies that specifically bind both IGF-I and IGF-II and inhibit the IGF-IR signal transduction function. Thus, these antibodies inhibit phosphorylation of the insulin-like growth factor receptor.

These monoclonal human antibodies can inhibit the motility of breast cancer cells in vitro. Additional compositions and methods are described below.

I. Abbreviations

BSA: bovine serum albumin
CDR: complementarity determining region
dsFv: disulfide stabilized fragment of a variable region
DMEM: Dulbecco's modified eagle medium
ELISA: enzyme-linked immunosorbent assay
EM: effector molecule
ERK: extra-cellular signal response kinase
FACS: fluorescence activated cell sorting
FBS: fetal bovine serum
FITC: fluoroscein istothiocyanate HEPES: 4-(2-hydroxyethyl)-1-piperazineethanesulfonic acid
IGF-I: insulin-like growth factor I
IGF-IR: insulin-like growth factor I receptor
IGF-II: insulin-like growth factor II
IGFBP: insulin-like growth factor binding proteins
IGFBP-rP: IGFBP-related proteins
IPTG: isopropyl-beta-D-thiogalactopyranoside
HCDR: heavy chain complementarity determining region
HAMA: human anti-murine antibody
HAT: hypoxanthine aminopterin thymidine
IL-6: interleukin-6
Ig: immunoglobulin
IR: insulin receptor
IRR: insulin receptor-related receptor
kDa: kilodaltons
LCDR: light chain complementarity determining region
MAb: monoclonal antibody
MAPK: mitogen-activated protein kinase
MMP: matrix-metalloproteinase
PBS: phosphate buffered saline
scFv: single chain fragment of a variable region
SDR: specificity determining residues
SDS-PAGE: sodium dodecyl (lauryl) sulfate-polyacrylamide gel electrophoreses
RIA: radioimmunoassay
$V_H$: variable region of a heavy chain
$V_L$: variable region of a light chain II. Terms Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administration: The introduction of a composition into a subject by a chosen route. For example, if the chosen route is intravenous, the composition is administered by introducing the composition into a vein of the subject.

Amplification: Of a nucleic acid molecule (such as, a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope of an antigen, such as insulin-like growth factor (IGF)-I, IGF-II, or a fragment thereof. In vivo, antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody, such that the antibody specifically binds the antigen.

This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

References to "$V_H$" or "VH" refer to the variable region of an immunoglobulin heavy chain, including that of an Fv, scFv, dsFv or Fab.

References to "$V_L$" or "VL" refer to the variable region of an immunoglobulin light chain, including that of an Fv, scFv, dsFv or Fab.

A "monoclonal antibody" is an antibody with a defined variable domain, such as a monoclonal antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds IGF-II.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Binding affinity: Affinity of an antibody for an antigen, such as IGF-I and IGF-II. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least a picomolar binding affinity. In other examples, a high binding affinity is 10 pm, 50 pM, 60 PM, 100 pM, 200 pM or 300 pM for IGF-I and/or IGF-II. Generally, a $K_D$ for an antibody with high binding affinity is $1 \times 10^{-10}$ M or less. In other embodiments, a high binding affinity is a $K_D$ of about $1.5 \times 10^{-10}$, about $2.0 \times 10^{-10}$, about $2.5 \times 10^{-10}$, about $3.0 \times 10^{-10}$, about $3.5 \times 10^{-10}$, about $4.0 \times 10^{-10}$, about $4.5 \times 10^{-10}$, or about $5.0 \times 10^{-10}$ M or less. In further embodiments, a high binding affinity is a $K_D$ of about $1.5 \times 10^{-11}$, about $2.0 \times 10^{-11}$, about $2.5 \times 10^{-11}$, about $3.0 \times 10^{-11}$, about $3.5 \times 10^{-11}$, about $4.0 \times 10^{-11}$, about $4.5 \times 10^{-11}$, or about $5.0 \times 10^{-11}$ M or less. In additional embodiments, a high binding affinity is a $K_D$ of about $1.5 \times 10^{-12}$, about $2.0 \times 10^{-12}$, about $2.5 \times 10^{-12}$, about $3.0 \times 10^{-12}$, about $3.5 \times 10^{-12}$, about $4.0 \times 10^{-12}$, about $4.5 \times 10^{-12}$, or about $5.0 \times 10^{-12}$ M or less.

Bi-specific antibody: A recombinant molecule composed of two different antigen binding moieties and consequently binds to two different antigenic epitopes. Bi-specific antibodies include chemically or genetically linked molecules of two antigen-binding moieties. The antigen binding moieties can be linked using a linker. The antigen binding moieties can be monoclonal antibodies, antigen-binding fragments (e.g., Fab, scFv), eAds, or combinations thereof. A bispecific antibody can include one or more constant domains, but does not necessarily include a constant domain.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a lymphoma, leukemia, or another tumor. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds IGF-II or a fragment thereof used in combination with a radioactive or chemical compound.

Conservative variants: "Conservative" amino acid substitutions are those substitutions that do not substantially affect or decrease the affinity of an antibody to IGF-I or IGF-II. For example, a human antibody that specifically binds IGF-I and IGF-II can include at most about 1, at most about 2, at most about 5, and most about 10, or at most about 15 conservative substitutions and specifically bind the original IGF-I and IGF-II polypeptide with a similar affinity. The term conservative variation also includes the use of a substituted amino acid in place of an unsubstituted parent amino acid, provided that antibody specifically binds IGF-I and IGF-II. Non-conservative substitutions are those that reduce an activity or binding to IGF-I and/or IGF-II.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity Determining Region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 58 (L-CDR2), 89 and 97 (L-CDR3); the CDRs of the heavy chain are bounded by the residues at positions 31 and 35b (H-CDR1), 50 and 65

(H-CDR2), 95 and 102 (H-CDR3), using the numbering convention delineated by Kabat et al., (1991) *Sequences of Proteins of Immunological Interest*, 5$^{th}$ Edition, U.S. Department of Health and Human Services, Public Health Service, National Institutes of Health, Bethesda, Md. (NIH Publication No. 91-3242).

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds IGF-I and IGF-II will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: A polynucleotide encoding an IGF-I and/or an IGF-II polypeptide or an antibody that binds IGF-I and IGF-II that includes a sequence that is degenerate as a result of the genetic code. There are 20 natural amino acids, most of which are specified by more than one codon. Therefore, all degenerate nucleotide sequences are included as long as the amino acid sequence of the IGF-I and/or IGF-II polypeptide or antibody that binds IGF-I and IGF-II encoded by the nucleotide sequence is unchanged.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-IGF-II antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art. See, for example, U.S. Pat. No. 4,957,735; and Connor et al., *Pharm. Ther.* 28:341-365, 1985. Diagnostic agents or moieties include radioisotopes and other detectable labels. Detectable labels useful for such purposes are also well known in the art, and include radioactive isotopes such as $^{32}$P, $^{125}$I, and $^{131}$I, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide.

Expressed: Translation of a nucleic acid into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, pap, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Framework Region: Amino acid sequences interposed between CDRs. Includes variable light and variable heavy framework regions. The framework regions serve to hold the CDRs in an appropriate orientation for antigen binding.

HAMA (Human anti-murine antibody) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunoconjugate: A covalent linkage of an effector molecule to an antibody. The effector molecule can be a detectable label or an immunotoxin. Specific, non-limiting examples of toxins include, but are not limited to, abrin, ricin, Pseudomonas exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule (EM). In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunogenic peptide: A peptide which comprises an allele-specific motif or other sequence, such as an N-terminal repeat, such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one specific non-limiting example, an immunogenic polypeptide includes a region of IGF-I or IGF-II, or a fragment thereof, wherein the polypeptide that is expressed on the cell surface of a host cell that expresses the full-length IGF-II polypeptide.

Immunogenic composition: A composition comprising an IGF-I and/or IGF-II polypeptide that induces a measurable CTL response against cells expressing IGF-I and/or an IGF-II polypeptide, or induces a measurable B cell response (such as production of antibodies) against an IGF-I and/or an IGF-II polypeptide. It further refers to isolated nucleic acids encoding an IGF-I and/or an IGF-II polypeptide that can be used to express the polypeptide(s) (and thus be used to elicit an immune response against this polypeptide). For in vitro use, an immunogenic composition may consist of the isolated protein or peptide epitope. For in vivo use, the immunogenic composition will typically comprise the protein or immunogenic peptide in pharmaceutically acceptable carriers, and/or other agents. Any particular peptide, such as an IGF-I or an IGF-II polypeptide, or nucleic acid encoding the polypeptide, can be readily tested for its ability to induce a CTL or B cell response by art-recognized assays Immunogenic compositions can include adjuvants, which are well known to one of skill in the art.

Immunologically reactive conditions: Includes reference to conditions which allow an antibody raised against a particular epitope to bind to that epitope to a detectably greater degree than, and/or to the substantial exclusion of, binding to substantially all other epitopes Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Immunotherapy: A method of evoking an immune response against cancer cells based on their production of target antigens Immunotherapy based on cell-mediated immune responses involves generating a cell-mediated response to cells that produce particular antigenic determinants, while immunotherapy based on humoral immune responses involves generating specific antibodies to cells that produce particular antigenic determinants.

Inhibiting or treating a disease: Inhibiting the full development of a disease or condition, for example, in a subject who is at risk for a disease such as a tumor (for example, a cancer such as a leukemia or a carcinoma). "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluoroscein istothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Ligand: Any molecule which specifically binds an IGF-I and/or an IGF-II protein and includes, inter alia, antibodies that specifically bind an IGF-I and/or IGF-II protein. In alternative embodiments, the ligand is a protein or a small molecule (one with a molecular weight less than 6 kiloDaltons).

Linker peptide: A peptide within an antibody binding fragment (such as an Fv fragment) which serves to indirectly bond the variable heavy chain to the variable light chain. "Linker" can also refer to a peptide serving to link a targeting moiety, such as a scFv, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule ("EM"). The linkage can be either by chemical or recombinant means. "Chemical means" refers to a reaction between the antibody moiety and the effector molecule such that there is a covalent bond formed between the two molecules to form one molecule.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Major Histocompatibility Complex or MHC: Generic designation meant to encompass the histocompatibility antigen systems described in different species, including the human leukocyte antigens ("HLA"). The term "motif" refers to the pattern of residues in a peptide of defined length, usually about 8 to about 11 amino acids, which is recognized by a particular MHC allele. The peptide motifs are typically different for each MHC allele and differ in the pattern of the highly conserved residues and negative binding residues.

Neoplasia and Tumor: The process of abnormal and uncontrolled growth of cells. Neoplasia is one example of a proliferative disorder. The product of neoplasia is a neoplasm (a tumor), which is an abnormal growth of tissue that results from excessive cell division. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples a tumor is a sarcoma, leukemia, prostate cancer, lung cancer, breast cancer, lung cancer, colon cancer, stomach cancer, uterine cancer, cervical cancer, esophageal cancer, liver cancer, pancreatic cancer, kidney cancer, thyroid cancer, brain cancer, or an ovarian cancer Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, CABIOS 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Oligonucleotide: A linear polynucleotide sequence of up to about 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Peptide: A chain of amino acids of between 3 and 30 amino acids in length. In one embodiment, a peptide is from about 10 to about 25 amino acids in length. In yet another embodiment, a peptide is from about 11 to about 20 amino acids in length. In yet another embodiment, a peptide is about 12 amino acids in length.

An "IGF-II peptide" is a series of contiguous amino acid residues from an IGF-II protein. An "IGF-I peptide" is a series of contiguous amino acid residues from an IGF-I protein. In one example, with respect to immunogenic compositions comprising an IGF-I or an IGF-II peptide, the term further refers to variations of these peptides in which there are conservative substitutions of amino acids, so long as the variations do not alter by more than about 20% (such as no more than about 1%, about 5%, or about 10%) the ability of the peptide to produce a B cell response, or, when bound to a Major Histocompatibility Complex Class I molecule, to activate cytotoxic T lymphocytes against cells expressing wild-type IGF-II protein. Induction of CTLs using synthetic peptides and CTL cytotoxicity assays are taught in, for example, U.S. Pat. No. 5,662,907.

Peptide modifications: IGF-I and IGF-II polypeptides include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, may be in the form of a pharmaceutically-acceptable acid addition salt, such as HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a IGF-II polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press, Buffalo Grove, Ill., pp. 165-174 and Principles of Pharmacology Munson (ed.) 1995, Ch. 102, for descriptions of techniques used in CADD. Also included are mimetics prepared using such techniques.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single- and double-stranded forms of DNA. A IGF-II polynucleotide is a nucleic acid encoding a IGF-II polypeptide.

Polypeptide: Any chain of amino acids, regardless of length or post-translational modification (such as glycosylation or phosphorylation). In one embodiment, the polypeptide is IGF-II polypeptide. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Probes and primers: A probe comprises an isolated nucleic acid attached to a detectable label or reporter molecule. Primers are short nucleic acids, and can be DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (such as the metallothionein promoter) or from mammalian viruses (such as the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation.

The IGF-I and IGF-II polypeptides disclosed herein, or antibodies that specifically bind IGF-I and IGF-II, can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Recombinant toxins: Chimeric proteins in which a cell targeting moiety is fused to a toxin (Pastan et al., *Science*, 254:1173-1177, 1991). If the cell targeting moiety is the Fv portion of an antibody, the molecule is termed a recombinant immunotoxin (Chaudhary et al., *Nature*, 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, cancers in which IGF-II is expressed.

Selectively hybridize: Hybridization under moderately or highly stringent conditions that exclude non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (such as GC versus AT content), and nucleic acid type (such as RNA versus DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (see Molecular Cloning: A Laboratory Manual, 2nd ed., Vol. 1-3, ed. Sambrook et al., Cold Spring Harbor Laboratory Press, Cold Spring Harbor, N. Y., 1989). Washing can be carried out using only one of these conditions, for example, high stringency conditions, or each of the conditions can be used, for example, for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a IGF-II polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, Gene 73:237, 1988; Higgins and Sharp, CABIOS 5:151, 1989; Corpet et al., *Nucleic Acids Research* 16:10881, 1988; and Pearson and Lipman, Proc. Natl. Acad. Sci. U.S.A. 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a IGF-II polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus an IGF-II specific binding agent is an agent that binds substantially to a IGF-II polypeptide. In one embodiment, the specific binding agent is a human monoclonal antibody that specifically binds both IGF-I and IGF-II polypeptides. Thus an IGF-I and IGF-II specific binding agent is an agent that binds substantially to both IGF-I and IGF-II polypeptides, but not to other unrelated polypeptides. In one embodiment, the specific binding agent is a human monoclonal antibody that specifically binds IGF-I and IGF-II polypeptides.

The term "specifically binds" refers, with respect to an antigen such as IGF-I and/or IGF-II, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the IGF-I/IGF-II polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

Subject: Living multi-cellular vertebrate organisms, a category that includes both human and veterinary subjects, including human and non-human mammals.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, CD8 T cells are cytotoxic T lymphocytes. In another embodiment, a CD8 cell is a suppressor T cell.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate a tumor or reduce metastases. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Antibodies that Specifically Bind IGF-I and IGF-II

Disclosed herein are monoclonal antibodies that specifically bind both IGF-I and IGF-II with a high affinity, such as picomolar affinity. These antibodies potently inhibit the IGF-1R signal transduction function. These antibodies are active in both an IgG and a scFv format, and can be included in bispecific antibodies.

The two ligands of the insulin like growth factor (IGF) system, IGF-I and IGF-II, are single-chain polypeptides sharing 62% homology with proinsulin. Exemplary amino sequences of human insulin chain A, insulin chain B, IGF-I precursor, mature IGF-I, IGF-II precursor (also known as "long IGF-II"), and mature IGF-II are set forth in SEQ ID NOs:1, 2, 3, 4, 5, and 6, respectively. The degree of homology between human and mouse IGF-I is 97%, while the degree of homology between human and mouse IGF-II is 91%. Amino acid sequences of mammalian IGF-I and IGF-II, such as the mouse and human proteins, are available on the internet through GENBANK®, see for example GENBANK® Accession No. CAA00082 (human IGF-II, Jan. 28, 1993), AAB21519 (human IGF-II, May 17, 2002), NP_034644 (mouse IGF-II, updated Aug. 6, 2006) NP_034642 (mouse IGF-I, updated Aug. 6, 2006), which are incorporated herein by reference. The amino acid sequence of the insulin receptor is available through GENBANK®, see Accession Nos. P6213 (Jan. 1, 1998) and NP000199 (Apr. 19, 2006).

Binding of IGFs to IGF-IR activates its intracellular tyrosine kinase domain, which results in autophosphorylation of the receptor. This in turn results in activation of various pathways that serve to increase cell proliferation, cell motility, and protection from apoptosis. IGF-IR has been linked to increased growth, survival, and oncogenic transformation of cancer cells (Kaleko et al., *Mol Cell Biol* 10:464-473, 1990; Baserga et al., *Biochim Biophys Acta* 1332:F105-F126, 1997; Blakesley et al., *J Endocrinol* 152: 339-344, 1997; Khandwala et al., *Endocr Rev* 21:215-244, 2000), and overexpression of IGF-IR has been observed in a variety of tumor types (Bergmann et al., *Cancer Res* 55:2007-2011, 1995; Werner et al., *Adv Cancer Res* 68:183-223, 1996; Happerfield et al., *J Pathol* 183:412-417, 1997; Xie et al., *Cancer Res* 59:3588-3591, 1999; Khandwala et al., *Endocr Rev* 21:215-244, 2000; Hellawell et al., *Cancer Res* 62:2942-2950, 2002; Weber et al., *Cancer* 95:2086-2095, 2002). The ligands of IGF-IR, IGF-I and IGF-II, are known to functions as mitogens in a variety of cancer cell lines (Cullen et al., *Cancer Res* 50:48-53, 1990; Ankrapp et al., *Cancer Res* 53:3399-3404, 1993; Kappel et al., *Cancer Res* 54:2803-2807 1994; Guo et al., *J Am Coll Surg* 181: 145-154, 1995; Steller et al., *Cancer Res* 56:1761-1765, 1996; Hermanto et al., *Cell Growth Differ* 11:655-664, 2000). Many tumors overexpress the IGF-II ligand (Werner et al., *Adv Cancer Res* 68:183-223, 1996), exhibiting IGF-II expression levels several fold higher than those of IGF-I.

Disclosed herein are human monoclonal antibodies that specifically bind human IGF-I and human IGF-II with very high affinity. In some embodiments, the antibody inhibits phosphorylation of the insulin-like growth factor receptor. In additional embodiments, the antibody inhibits the phosphorylation of the insulin receptor. In additional examples, the antibody inhibits phosphorylation of the insulin-like growth factor receptor. In a further embodiment, administration of an effective amount of the antibody to a subject decreases the autophosphorylation on tyrosine residues of the human IGF-IR as compared to a control. The phosphorylation of the human IFG-1R can be measured by any method known to one of skill in the art.

In one embodiment, the antibodies bind IGF-I and IGF-II with an equilibrium constant ($K_d$) of 200 pM or less. In other embodiments, the antibodies bind IGF-I and IGF-II with an equilibrium association constant ($K_d$) of 100 pM or less. In further embodiments, the antibodies bind IGF-I and IGF-II with an equilibrium constant ($K_d$) of 60 pM or less. In further embodiments, the antibodies bind IGF-I with an equilibrium constant ($K_d$) of 200 pM or less and IGF-II with an equilibrium constant ($K_d$) of 60 pM or less. In specific examples, the disclosed antibodies bind IGF-I and IGF-II with a high binding affinity, such as at least about 10 pm, at least about 50 pM, at least about 60 pM, at least about 100 pM, at least about 200 pM or about least about 500 pM for IGF-I and/or IGF-II. Affinity can be measured by surface plasmin resonance.

In some embodiments, the antibodies have a $K_D$ for IGF-I and IGF-II of $1 \times 10^{-10}$ M or less. In other embodiments, the antibodies have a $K_D$ for IGF-I and IGF-II of about $1.5 \times 10^{-10}$, about $2.0 \times 10^{-10}$, about $2.5 \times 10^{-10}$, about $3.0 \times 10^{-10}$, about $3.5 \times 10^{-10}$, about $4.0 \times 10^{-10}$, about $4.5 \times 10^{-10}$, or about $5.0 \times 10^{-10}$ M or less. In further embodiments, the antibodies have a $K_D$ for IGF-I and IGF-II of about $1.5 \times 10^{-11}$, about $2.0 \times 10^{-11}$, about $2.5 \times 10^{-11}$, about $3.0 \times 10^{-11}$, about $3.5 \times 10^{-11}$, about $4.0 \times 10^{-11}$, about $4.5 \times 10^{-11}$, or about $5.0 \times 10^{-11}$ M or less. In additional embodiments, a, the antibodies have a $K_D$ for IGF-I and IGF-II of about $1.5 \times 10^{-12}$, about $2.0 \times 10^{-12}$, about $2.5 \times 10^{-12}$, about $3.0 \times 10^{-12}$, about $3.5 \times 10^{-12}$, about $4.0 \times 10^{-12}$, about $4.5 \times 10^{-12}$, or about $5.0 \times 10^{-12}$ M or less. In several embodiments, the human monoclonal antibodies bind human IGF-I with a binding affinity of $1 \times 10^{-10}$ M$^{-1}$, at least about $2 \times 10^{-10}$ M$^{-1}$, at least about $3 \times 10^{-10}$ M$^{-1}$, at least about $1 \times 10^{-10}$ M$^{-1}$, at least about $2.0 \times 10^{-10}$ M$^{-1}$, at least about $3 \times 10^{-10}$ M$^{-1}$ at least about $6 \times 10^{-10}$ M$^{-1}$, or at least about $8 \times 10^{-10}$ M$^{-1}$. In additional embodiments, the human monoclonal antibodies bind human IGF-II with a binding affinity of $1 \times 10^{-10}$ M$^{-1}$, at least about $2 \times 10^{-10}$ M$^{-1}$, at least about $3 \times 10^{-10}$ M$^{-1}$, at least about $1 \times 10^{-10}$ M$^{-1}$, at least about $2.0 \times 10^{-10}$ M$^{-1}$, at least about $3 \times 10^{-10}$ M$^{-1}$ at least about $6 \times 10^{-10}$ M$^{-1}$, or at least about $8 \times 10^{-10}$ M$^{-1}$.

In additional examples, the human monoclonal antibody binds the epitope of IGF-II bound by m708.5, which is disclosed herein. Thus, in one example, the human monoclonal antibody binds the epitope of IGF-I and IGF-II bound m708.5.

A major limitation in the clinical use of mouse monoclonal antibodies is the development of a human anti-murine antibody (HAMA) response in the patients receiving the treatments. The HAMA response can involve allergic reactions and an increased rate of clearance of the administered antibody from the serum. Various types of modified monoclonal antibodies have been developed to minimize the HAMA response while trying to maintain the antigen binding affinity of the parent monoclonal antibody. One type of modified monoclonal antibody is a human-mouse chimera in which a murine antigen-binding variable region is coupled to a human constant domain (Morrison and Schlom, *Important Advances in Oncology*, Rosenberg, S. A. (Ed.), 1989). A second type of modified monoclonal antibody is the complementarity determining region (CDR)-grafted, or humanized, monoclonal antibody (Winter and Harris, *Immunol. Today* 14:243-246, 1993). In some embodiments, the antibodies disclosed herein are fully human; both the framework region and the CDRs are from human antibodies. Thus, a HAMA is not induced when these human antibodies are administered to human subjects.

In several embodiments, the human monoclonal antibody includes at least one of the light chain CDRs and/or at least one of the heavy chain CDRs from the variable heavy and light chain sequences shown below:

```
Consensus V_H
                                            (SEQ ID NO: 7)
QVQLQQX1GAEVKMPGSSVKX2SCX3ASGGTFSSYAISWX4RQAPGQGL
EWMGGIIPTLX5IVKYX6X7KFQGRVTITADX8SX9X10TX11YMELSX12
LX13SEDTAVYYCAGGPRGYSYNFDX14WX15QGTX16VTVSS
``` wherein $X_1$ is L or P; $X_2$ is V or I; $X_3$ is K or R; $X_4$ is V or M; $X_5$ is G or S; $X_6$ is A or S; $X_7$ is Q or P; $X_8$ is K or E; $X_9$ is T or K; $X_{10}$ is S or G; $X_{11}$ is A or V; $X_{12}$ is S or N; $X_{13}$ is G or R; $X_{14}$ is N or E; $X_{15}$ is G or S; and $X_{16}$ is L or M and wherein H-CDR1 is amino acids 26-33 of SEQ ID NO: 7, H-CDR2 is amino acids 51-58 of SEQ ID NO: 7, and H-CDR3 is amino acids 97-109 of SEQ ID NO: 7. The locations of the CDRs are underlined in the sequence shown above.

```
Consensus VL
                                            (SEQ ID NO: 8)
DIQX17TQSPSSLSASVGDRVTIX18CRASQTISRYX19NWYQQKPGKAP
KLLIYAASX20LQSGX21SSRFSGSGSGTEFX22LTISSLQPEDFATYFC
QQTYSPPITFGQGTRLEIKX23
``` wherein $X_{17}$ is M or I; $X_{18}$ is V or A; $X_{19}$ is V or L; $X_{20}$ is S or N; $X_{21}$ is V or I; $X_{22}$ is A or T; and $X_{23}$ is Q or R and wherein L-CDR1 is amino acids 27-32 of SEQ ID NO: 8, L-CDR2 is amino acids 50-52 of SEQ ID NO: 8, and L-CDR3 is amino acids 89-97 of SEQ ID NO: 8. The locations of the CDRs are underlined in the sequence shown above.

In one embodiment, the variable region of the heavy chain of the human monoclonal antibody includes amino acids 97-109 of SEQ ID NO: 7 (HCDR3). The heavy chain of the isolated human monoclonal antibody can include one or more of amino acids 26-33 of SEQ ID NO: 7 (HCDR1) and/or amino acids 51-58 of SEQ ID NO: 7 (HCDR2) and/or amino acids 97-109 of SEQ ID NO: 7 (HCDR3), or all of these sequences. Thus, the heavy chain can include amino acids 26-33 of SEQ ID NO: 7 (HCDR1) and amino acids 51-58 of SEQ ID NO: 7 (HCDR2) and amino acids 97-109 of SEQ ID NO: 7 (HCDR3).

In some examples, $X_{14}$ is E. Thus, the variable region of the heavy chain can include amino acids 97-109 of SEQ ID NO: 7 (HCDR3), wherein $X_{14}$ is E. The heavy chain of the isolated human monoclonal antibody can include one or more of amino acids 26-33 of SEQ ID NO: 7 (HCDR1) and/or amino acids 51-58 of SEQ ID NO: 7 (HCDR2) and/or amino acids 97-109 of SEQ ID NO: 7 (HCDR3) wherein $X_{14}$ is E, or all of these sequences. Thus, the heavy chain can include amino acids 26-33 of SEQ ID NO: 7 (HCDR1) and amino acids 51-58 of SEQ ID NO: 7 (HCDR2) and amino acids 97-109 of SEQ ID NO: 7 (HCDR3) wherein $X_{14}$ is E.

In other examples, $X_{14}$ is N. The heavy chain of the isolated human monoclonal antibody can include one or more of amino acids 26-33 of SEQ ID NO: 7 (HCDR1) and/or amino acids 51-58 of SEQ ID NO: 7 (HCDR2) and/or amino acids 97-109 of SEQ ID NO: 7 (HCDR3) wherein $X_{14}$ is N, or all of these sequences. Thus, the heavy chain can include amino acids 26-33 of SEQ ID NO: 7 (HCDR1) and amino acids 51-58 of SEQ ID NO: 7 (HCDR2) and amino acids 97-109 of SEQ ID NO: 7 (HCDR3) wherein $X_{14}$ is N.

In further examples, $X_5$ is G. The heavy chain of the isolated human monoclonal antibody can include one or more of amino acids 26-33 of SEQ ID NO: 7 (HCDR1) and/or amino acids 51-58 of SEQ ID NO: 7 (HCDR2) and/or amino acids 97-109 of SEQ ID NO: 7 (HCDR3) wherein $X_5$ is G, or all of these sequences. Thus, the heavy chain can include amino acids 26-33 of SEQ ID NO: 7 (HCDR1) and amino acids 51-58 of SEQ ID NO: 7 (HCDR2) and amino acids 97-109 of SEQ ID NO: 7 (HCDR3) wherein $X_5$ is G.

In other examples, $X_5$ is S. The heavy chain of the isolated human monoclonal antibody can include one or more of amino acids 26-33 of SEQ ID NO: 7 (HCDR1) and/or amino acids 51-58 of SEQ ID NO: 7 (HCDR2) and/or amino acids 97-109 of SEQ ID NO: 7 (HCDR3) wherein $X_5$ is S, or all of these sequences. Thus, the heavy chain can include amino acids 26-33 of SEQ ID NO: 7 (HCDR1), amino acids 51-58 of SEQ ID NO: 7 (HCDR2) and amino acids 97-109 of SEQ ID NO: 7 (HCDR3) wherein $X_5$ is S.

In yet additional examples, such as m708.5, $X_5$ is G and $X_{14}$ is N. The heavy chain of the isolated human monoclonal antibody can include one or more of amino acids 26-33 of SEQ ID NO: 7 (HCDR1) and/or amino acids 51-58 of SEQ ID NO: 7 (HCDR2) and/or amino acids 97-109 of SEQ ID NO: 7 (HCDR3) wherein $X_5$ is G and $X_{14}$ is N, or all of these sequences. Thus, the heavy chain can include amino acids 26-33 of SEQ ID NO: 7 (HCDR1) and amino acids 51-58 of SEQ ID NO: 7 (HCDR2) and amino acids 97-109 of SEQ ID NO: 7 (HCDR3) wherein $X_5$ is G and $X_{14}$ is N. In further examples, such as m708.7, $X_5$ is G and $X_{14}$ is E. The heavy chain of the isolated human monoclonal antibody can include one or more of amino acids 26-33 of SEQ ID NO: 7 (HCDR1) and/or amino acids 51-58 of SEQ ID NO: 7 (HCDR2) and/or amino acids 97-109 of SEQ ID NO: 7 (HCDR3) wherein $X_5$ is G and $X_{14}$ is E, or all of these sequences. Thus, the heavy chain can include amino acids 26-33 of SEQ ID NO: 7 (HCDR1) and amino acids 51-58 of SEQ ID NO: 7 (HCDR2) and amino acids 97-109 of SEQ ID NO: 7 (HCDR3) wherein $X_5$ is G and $X_{14}$ is E. In other examples, such as m708.6, $X_5$ is S and $X_{14}$ is E. The heavy chain of the isolated human monoclonal antibody can include one or more of amino acids 26-33 of SEQ ID NO: 7 (HCDR1) and/or amino acids 51-58 of SEQ ID NO: 7 (HCDR2) and/or amino acids 97-109 of SEQ ID NO: 7 (HCDR3) wherein $X_5$ is S and $X_{14}$ is E, or all of these sequences. Thus, the heavy chain can include amino acids 26-33 of SEQ ID NO: 7 (HCDR1) and amino acids 51-58 of SEQ ID NO: 7 (HCDR2) and amino acids 97-109 of SEQ ID NO: 7 (HCDR3) wherein $X_5$ is S and $X_{14}$ is E.

The light chain of the variable region of the human monoclonal antibody can include amino acids 27-32 of SEQ ID NO: 8 (LCDR1). The variable region of the light chain of the human monoclonal antibody can include amino acids 27-32 of SEQ ID NO: 8 (LCDR1), amino acids 50-52 of SEQ ID NO: 8 (LCDR2) and/or amino acids 89-97 of SEQ ID NO: 8 (LCDR3), or all of these sequences.

In yet additional examples, such as m708.5, $X_5$ is G and $X_{14}$ is N. The heavy chain of the isolated human monoclonal antibody includes amino acids 26-33 of SEQ ID NO: 7 (HCDR1) and amino acids 51-58 of SEQ ID NO: 7 (HCDR2) and amino acids 97-109 of SEQ ID NO: 7 (HCDR3) wherein $X_5$ is G and $X_{14}$ is N. The light chain of the isolated human monoclonal antibody includes amino acids 27-32 of SEQ ID NO: 8 (LCDR1), amino acids 50-52 of SEQ ID NO: 8 (LCDR2) and amino acids 89-97 of SEQ ID NO: 8 (LCDR3).

In further examples, such as m708.7, $X_5$ is G and $X_{14}$ is E. The heavy chain includes amino acids 26-33 of SEQ ID NO: 7 (HCDR1) and amino acids 51-58 of SEQ ID NO: 7 (HCDR2) and amino acids 97-109 of SEQ ID NO: 7 (HCDR3) wherein $X_5$ is G and $X_{14}$ is E. The light chain of the isolated human monoclonal antibody includes amino acids 27-32 of SEQ ID NO: 8 (LCDR1), amino acids 50-52 of SEQ ID NO: 8 (LCDR2) and amino acids 89-97 of SEQ ID NO: 8 (LCDR3).

In other examples, such as m708.6, $X_5$ is S and $X_{14}$ is E. The heavy chain includes amino acids 26-33 of SEQ ID NO: 7 (HCDR1) and amino acids 51-58 of SEQ ID NO: 7 (HCDR2) and amino acids 97-109 of SEQ ID NO: 7 (HCDR3) wherein $X_5$ is S and $X_{14}$ is E. The light chain of the isolated human monoclonal antibody includes amino acids 27-32 of SEQ ID NO: 8 (LCDR1), amino acids 50-52 of SEQ ID NO: 8 (LCDR2) and amino acids 89-97 of SEQ ID NO: 8 (LCDR3).

In several examples, the human monoclonal antibody includes at least one of the light chain CDRs and/or at least one of the heavy chain CDRs from the variable heavy and light chain sequences shown below:

```
>m708.5
Heavy chain variable domain
                                          (SEQ ID NO: 7)
QVQLQQLGAEVKMPGSSVKVSCKASGGTFSSYAISWVRQAPGQGLEW
MGGIIPTLGIVKYAQKFQGRVTITADKSTSTAYMELSSLGSEDTAVY
YCAGGPRGYSYNFDNWGQGTLVTVSS,
``` wherein $X_1$ is L; $X_2$ is V; $X_3$ is K; $X_4$ is V; $X_5$ is G; $X_6$ is A; $X_7$ is Q; $X_8$ is K; $X_9$ is T; $X_{10}$ is S; $X_{11}$ is A; $X_{12}$ is S; $X_{13}$ is G; $X_{14}$ is N; $X_{15}$ is G; and $X_{16}$ is L)
wherein H-CDR1 is amino acids 26-33 of SEQ ID NO: 7, H-CDR2 is amino acids 51-58 of SEQ ID NO: 7, and H-CDR3 is amino acids 97-109 of SEQ ID NO: 7. The locations of the CDRs are highlighted and underlined in the sequence shown above.

```
Light chain variable domain
                                          (SEQ ID NO: 8)
DIQMTQSPSSLSASVGDRVTIVCRASQTISRYVNWYQQKPGKAPKLLIY
AASSLQSGVSSRFSGSGSGTEFALTISSLQPEDFATYFCQQTYSPPITF
GQGTRLEIKQ,
``` wherein $X_{17}$ is M; $X_{18}$ is V; $X_{19}$ is V; $X_{20}$ is S; $X_{21}$ is V; $X_{22}$ is A; and $X_{23}$ is Q)
wherein L-CDR1 is amino acids 27-32 of SEQ ID NO: 8, L-CDR2 is amino acids 50-52 of SEQ ID NO: 8, and L-CDR3 is amino acids 89-97 of SEQ ID NO: 8. The locations of the CDRs are highlighted and underlined in the sequence shown above.

In one example, the heavy chain of the monoclonal antibody includes the amino acid sequence set forth as SEQ ID NO: 7, wherein $X_1$ is L; $X_2$ is V; $X_3$ is K; $X_4$ is V; $X_5$ is G; $X_6$ is A; $X_7$ is Q; $X_8$ is K; $X_9$ is T; $X_{10}$ is S; $X_{11}$ is A; $X_{12}$ is S; $X_{13}$ is G; $X_{14}$ is N; $X_{15}$ is G; and $X_{16}$ is L. In another example, the light chain of the monoclonal antibody includes the amino acid sequence set forth as SEQ ID NO: 8, wherein $X_{17}$ is M; $X_{18}$ is V; $X_{19}$ is V; $X_{20}$ is S; $X_{21}$ is V; $X_{22}$ is A; and $X_{23}$ is Q. In a further example, the heavy chain of the monoclonal antibody includes the amino acid sequence set forth as SEQ ID NO: 7, wherein $X_1$ is L; $X_2$ is V; $X_3$ is K; $X_4$ is V; $X_5$ is G; $X_6$ is A; $X_7$ is Q; $X_8$ is K; $X_9$ is T; $X_{10}$ is S; $X_{11}$ is A; $X_{12}$ is S; $X_{13}$ is G; $X_{14}$ is N; $X_{15}$ is G; and $X_{16}$ is L and the light chain of the monoclonal antibody includes the amino acid sequence set forth as SEQ ID NO: 8, wherein $X_{17}$ is M; $X_{18}$ is V; $X_{19}$ is V; $X_{20}$ is S; $X_{21}$ is V; $X_{22}$ is A; and $X_{23}$ is Q.

However, in other examples, the heavy chain of the monoclonal antibody includes the amino acid sequence set forth as SEQ ID NO: 7, wherein $X_1$ is P; $X_2$ is V; $X_3$ is K; $X_4$ is M; $X_5$ is S; $X_6$ is A; $X_7$ is P; $X_8$ is K; $X_9$ is T; $X_{10}$ is G; $X_{11}$ is A; $X_{12}$ is N; $X_{13}$ is R; $X_{14}$ is E; $X_{15}$ is S; and $X_{16}$ is M. In another example, the light chain of the monoclonal antibody includes the amino acid sequence set forth as SEQ ID NO: 8, wherein $X_{17}$ is I; $X_{18}$ is A; $X_{19}$ is L; $X_{20}$ is S; $X_{21}$ is V; $X_{22}$ is T; and $X_{23}$ is R. In a further example, the heavy chain of the monoclonal antibody includes the amino acid sequence set forth as SEQ ID NO: 7, wherein $X_1$ is P; $X_2$ is V; $X_3$ is K; $X_4$ is M; $X_5$ is S; $X_6$ is A; $X_7$ is P; $X_8$ is K; $X_9$ is T; $X_{10}$ is G; $X_{11}$ is A; $X_{12}$ is N; $X_{13}$ is R; $X_{14}$ is E; $X_{15}$ is S; and $X_{16}$ is M and the light chain of the monoclonal antibody includes the amino acid sequence set forth as SEQ ID NO: 8, wherein $X_{17}$ is I; $X_{18}$ is A; $X_{19}$ is L; $X_{20}$ is S; $X_{21}$ is V; $X_{22}$ is T; and $X_{23}$ is R.

In yet other examples, the heavy chain of the monoclonal antibody includes the amino acid sequence set forth as SEQ ID NO: 7, wherein $X_1$ is P; $X_2$ is I; $X_3$ is R; $X_4$ is V; $X_5$ is G; $X_6$ is S; $X_7$ is Q; $X_8$ is E; $X_9$ is K; $X_{10}$ is S; $X_{11}$ is V; $X_{12}$ is S; $X_{13}$ is R; $X_{14}$ is E; $X_{15}$ is S; and $X_{16}$ is L. In another example, the light chain of the monoclonal antibody includes the amino acid sequence set forth as SEQ ID NO: 8, wherein $X_{17}$ is M; $X_{18}$ is A; $X_{19}$ is L; $X_{20}$ is N; $X_{21}$ is I; $X_{22}$ is T; and $X_{23}$ is R. In further examples, the heavy chain of the monoclonal antibody includes the amino acid sequence set forth as SEQ ID NO: 7, wherein $X_1$ is P; $X_2$ is I; $X_3$ is R; $X_4$ is V; $X_5$ is G; $X_6$ is S; $X_7$ is Q; $X_8$ is E; $X_9$ is K; $X_{10}$ is S; $X_{11}$ is V; $X_{12}$ is S; $X_{13}$ is R; $X_{14}$ is E; $X_{15}$ is S; and $X_{16}$ is L and the light chain of the monoclonal antibody includes the amino acid sequence set forth as SEQ ID NO: 8, wherein $X_{17}$ is M; $X_{18}$ is A; $X_{19}$ is L; $X_{20}$ is N; $X_{21}$ is I; $X_{22}$ is T; and $X_{23}$ is R.

The amino acid sequence of the heavy chain variable domain of the present disclosed antibodies differs from the heavy chain variable domain of m708.2. In some embodiments, the amino acid sequence of the light chain variable domain of the presently disclosed antibodies differs from the light chain variable domain of m7082.

```
Heavy chain variable domain
                                          (SEQ ID NO: 9)
QVQLQQPGAEVKKPGSSVKVSCKASGGTFSSYAISWVRQAPGQGLEWM
GGIIPILGIANYAQKFQGRVTITADESTSTAYMELSSLRSEDTAVYYC
ARGPRGYSYNFDYWGQGTLVTVSS
``` wherein H-CDR1 is amino acids 26-33 of SEQ ID NO: 9, H-CDR2 is amino acids 51-58 of SEQ ID NO: 9, and H-CDR3 is amino acids 97-109 of SEQ ID NO: 9. The locations of the CDRs are highlighted and underlined in the sequence shown above.

Light chain variable domain
(SEQ ID NO: 10)
DIQMTQSPSSLSASVGDRVTIACRAS<u>QTISRY</u>LNWYQQKPGKAPKLLIY
AA<u>SS</u>LQSGVSSRFSGSGSGTEFTLTISSLQPEDFATYFC<u>QQTYSPPITF</u>
GQGTRLEIKR wherein L-CDR1 is amino acids 27-32 of SEQ ID NO: 10, L-CDR2 is amino acids 50-52 of SEQ ID NO: 10, and L-CDR3 is amino acids 89-97 of SEQ ID NO: 10. The locations of the CDRs are highlighted and underlined in the sequence shown above.

In some embodiments, the amino acid sequence of H-CDR2 of the antibodies is at least two amino acids different than amino acids 51-58 SEQ ID NO: 9. In additional embodiments, the H-CDR3 of the antibody is at least two amino acids different than amino acids 97-109 of SEQ ID NO: 9. In some embodiments, the amino acid sequence of H-CDR2 of the antibodies differs by two amino acids from amino acids 51-58 SEQ ID NO: 9 and the H-CDR3 differs by two amino acids from amino acids 97-109 of SEQ ID NO: 9. In further embodiments, the antibody does not include the amino acid sequence set forth as SEQ ID NO: 9. In additional embodiments, the antibody does not include amino acids 51-58 of SEQ ID NO: 9 and/or amino acids 97-109 of SEQ ID NO: 9. In additional embodiments, the antibody does not include the amino acid sequence set forth as SEQ ID NO: 9. In yet other embodiments, the antibody does not include the amino acid sequence set forth as SEQ ID NO: 10.

The monoclonal antibody can be of any isotype. The monoclonal antibody can be, for example, an IgM or an IgG antibody, such as IgG1, IgG2, IgG3 or IgG4. The class of an antibody that specifically binds IGF-II can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds IGF-I and IGF-II that was originally IgM may be class switched to an IgG. Class switching can be used to convert one IgG subclass to another, such as from $IgG_1$ to $IgG_2$ or to $IgG_4$.

Fully human monoclonal antibodies include a human framework region. This human framework region can be the framework regions disclosed in one or more of SEQ ID NOS: 7-8 (these sequences include CDR sequences as well as framework sequences). Exemplary heavy chain framework regions are amino acids 1-25, 34-50, 59-96, and 110-120 or SEQ ID NO: 7. Thus, exemplary heavy chain framework regions are amino acids 1-25, 34-50, 59-96, and 110-120 of SEQ ID NO: 7, wherein $X_1$ is L; $X_2$ is V; $X_3$ is K; $X_4$ is V; $X_6$ is A; $X_7$ is Q; $X_8$ is K; $X_9$ is T; $X_{10}$ is S; $X_{11}$ is A; $X_{12}$ is S; $X_{13}$ is G; $X_{15}$ is G; and $X_{16}$ is L. Exemplary heavy chain framework regions are amino acids 1-25, 34-50, 59-96, and 110-120 of SEQ ID NO: 7, wherein $X_1$ is P; $X_2$ is V; $X_3$ is K; $X_4$ is M; $X_6$ is A; $X_7$ is P; $X_8$ is K; $X_9$ is T; $X_{10}$ is G; $X_{11}$ is A; $X_{12}$ is N; $X_{13}$ is R; $X_{15}$ is S; and $X_{16}$ is M. Additional exemplary heavy chain framework regions are amino acids 1-25, 34-50, 59-96, and 110-120 of SEQ ID NO: 7, wherein $X_1$ is P; $X_2$ is I; $X_3$ is R; $X_4$ is V; $X_6$ is S; $X_7$ is Q; $X_8$ is E; $X_9$ is K; $X_{10}$ is S; $X_{11}$ is V; $X_{12}$ is S; $X_{13}$ is R; $X_{15}$ is S; and $X_{16}$ is L. Exemplary light chain framework regions are amino acids 1-26, 33-49, 53-88 and 98-108 of SEQ ID NO: 8. wherein $X_{17}$ is M; $X_{18}$ is V; $X_{19}$ is V; $X_{20}$ is S; $X_{21}$ is V; $X_{22}$ is A; and $X_{23}$ is Q. Exemplary light chain framework regions are amino acids 1-26, 33-49, 53-88 and 98-108 of SEQ ID NO: 8. wherein $X_{17}$ is I; $X_{18}$ is A; $X_{19}$ is L; $X_{20}$ is S; $X_{21}$ is V; $X_{22}$ is T; and $X_{23}$ is R. Additional exemplary light chain framework regions are amino acids 1-26, 33-49, 53-88 and 98-108 of SEQ ID NO: 8. wherein $X_{17}$ is M; $X_{18}$ is A; $X_{19}$ is L; $X_{20}$ is N; $X_{21}$ is I; $X_{22}$ is T; and $X_{23}$ is R. Exemplary framework regions are shown in FIG. 10, and include the framework regions from m708.5, m708.6 and m708.7.

However, the framework regions can be from another source. Exemplary framework regions are disclosed, for example, in U.S. Pat. No. 7,824,681, which is incorporated herein by reference.

In some embodiments, the light chain of the antibody includes amino acids 1-25, amino acids 34-50, amino acids 59-96 and/or amino acids 110-120 of SEQ ID NO: 7. In additional embodiments, the light chain of the antibody includes amino acids 1-25, amino acids 34-50, amino acids 59-96 and/or amino acids 110-120 of SEQ ID NO: 9. In other embodiments, the antibody includes amino acids 1-26, amino acids 33-49, amino acids 53-88 and/or amino acids 98-108 of SEQ ID NO: 8. In further embodiments, the antibody includes amino acids 1-26, amino acids 33-49, amino acids 53-88 and/or amino acids 98-108 of SEQ ID NO: 10.

The antibodies disclosed herein can include a light chain framework region and a heavy chain framework region. Thus, the antibody can include all of the light chain framework regions (amino acids of the amino acid sequence set forth as SEQ ID NO: 8 or the amino acid sequence set forth as SEQ ID NO: 10. The antibody can include all of the heavy chain framework regions of the amino acid sequence set forth as SEQ ID NO: 7 or the amino acid sequence set forth as SEQ ID NO: 9.

In some embodiments, the antibody includes a light chain framework region, but do not include the light chain framework regions of the amino acid sequence set forth as SEQ ID NO: 8. In additional embodiments, the antibody includes a heavy chain framework region, but do not include the heavy chain framework region regions of the amino acid sequence set forth as SEQ ID NO: 10. In further embodiments, the antibody includes the heavy chain framework regions of the amino acid sequence set forth as SEQ ID NO: 7 with at most 1, 2, 3 or 4 conservative substitutions and the light chain framework region of the amino acid sequence set forth as SEQ ID NO: 8 with at most 1, 2, 3, or 4 conservative substitutions. The antibody.

Antibody fragments that specifically bind IGF-I and IGF-II are encompassed by the present disclosure, such as Fab, F(ab')$_2$, and Fv which include a heavy chain and light chain variable region and are capable of binding the epitopic determinant on IGF-I and IGF-II. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')₂, the fragment of the antibody that can be obtained by treating whole antibody with the enzyme pepsin without subsequent reduction; F(ab')₂ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV₂), defined as a dimer of an scFV. This has also been termed a "miniantibody."

Methods of making these fragments are known in the art (see for example, Harlow and Lane, *Antibodies: A Laboratory Manual*, Cold Spring Harbor Laboratory, New York, 1988). In several examples, the variable region included in the antibody is the variable region of m708.5. In one group of embodiments, the antibodies have $V_H$ CDRs of m708.5, or a combination of these CDRs, as discussed above. In one group of embodiments, the antibodies have $V_L$ CDRs of m708.5, or a combination of these CDRs, as discussed above.

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds. In several embodiments, the antibodies disclosed herein are active in an scFV format.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV₂), are also contemplated. In several embodiments, the antibodies disclosed herein are active in an scFV format.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')₂. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced, that retain the ability to bind to IGF-I and IGF-II with picomolar affinity. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Thus, one of skill in the art can readily review the sequences of the antibodies disclosed herein, such and the framework regions, and identify a conservative substitution, and produce the conservative variant using well-known molecular techniques.

Effector molecules, such as therapeutic, diagnostic, or detection moieties can be linked to an antibody of interest, such as a human antibody that specifically binds IGF-I and IGF-II with picomolar affinity, using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH₂) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers.

Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or any of they antibody fragments disclosed herein that specifically bind IGF-I and IGF-II with picomolar affinity can be derivatized or linked to another molecule (such as another peptide or protein). In general, the antibodies or portion thereof is derivatized such that the binding to IGF-I and IGF-II is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill. Bispecific antibodies can also be produced using linkers of $G_4S$ (SEQ ID NO: 25) triplicates.

Thus, bispecific antibodies are provided, wherein the bispecific antibody includes any of the antibodies that specifically bind IGF-I and IGF-II with picomolar affinity. In several embodiments, the bispecific antibody includes the CDRs of the heavy chain variable region of an antibody that specifically binds IGF-II only, and the CDRs of the light chain variable region of an antibody that specifically binds IGF-II only. Antibodies that bind IGF-II are disclosed, for example, in U.S. Provisional Application No. 61/548,164, filed Oct. 17, 2011, which is incorporated herein by reference. Additional antibodies that specifically bind IGF-II, such as, but not limited to, m606, m610, m616 are disclosed, for example, in PCT Publication No. WO 2007/022172, which is also incorporated herein by reference. These antibodies can inhibit the phosphorylation of the IGF-IR and IR, and inhibit the growth and migration of human cancer cells in vitro and in vivo.

In some embodiments, the bispecific antibody includes a heavy chain variable region that includes the amino acid sequence set forth as amino acids 26-33 of SEQ ID NO: 7, amino acids 51-58 of SEQ ID NO: 7 and amino acids 97-109 of SEQ ID NO: 7 and a light chain variable region that includes the amino acid sequence set forth as amino acids 27-32 of SEQ ID NO: 8, amino acids 50-52 of SEQ ID NO: 8 and amino acids 89-97 of SEQ ID NO: 8.

In some embodiments, the bispecific antibodies includes the heavy chain variable region and/or the CDRs of the m610.27 heavy chain variable region amino acid sequence:

Variable region
(SEQ ID NO: 23)
<u>QVQLVQSGAEVKKPGASVKVSCKASGYTFTSYYMHWVRQAPGQGLEWMGII</u>
<u>NPSGGSTSYAQKFQGRVTMTRDTSTSTVYMELSRLRSDDTAVYYCARDVQW</u>
<u>LAYGMDVWGQGTTVTVSS</u>

Thus, in some embodiments, the heavy chain variable region of the antibody that specifically binds IGF-II includes one or more of amino acids 26-33 of SEQ ID NO: 23, amino acids 51-58 of SEQ ID NO: 23, and amino acids 97-109 of SEQ ID NO: 23, and specifically binds IGF-II. In additional embodiments, the heavy chain variable region of the antibody that specifically binds IGF-II includes amino acids 26-33 of SEQ ID NO: 23, amino acids 51-58 of SEQ ID NO: 23, and amino acids 97-109 of SEQ ID NO: 23, and specifically binds IGF-II. In further embodiments, the heavy chain variable region includes the amino acid sequence set forth as SEQ ID NO: 23.

In additional embodiments, the bispecific antibody includes the light chain variable region and/or the CDRs of m610.27 light chain variable region amino acid sequence:

Variable region
(SEQ ID NO: 24)
<u>DIQMTQSPSSLSASVGDRVTITCRASQSISSYLNWYQQKPGRAPDLLI</u>
<u>NAASSLQSGVPSRFSGSGSGTDFTLTISSLQPEDFATYFCQQSYSLPF</u>
<u>TFGGGTKVEIK</u>

Thus, in some embodiments, the light chain variable region of the antibody that specifically binds IGF-II includes at least one of amino acids 27-32 of SEQ ID NO: 24, amino acids 50-52 of SEQ ID NO: 24, and amino acids 89-98 of SEQ ID NO: 24, and specifically binds IGF-II. In additional embodiments, the light chain variable region of the antibody that specifically binds IGF-II includes amino acids 27-32 of SEQ ID NO: 24, amino acids 50-52 of SEQ ID NO: 24, and amino acids 89-98 of SEQ ID NO: 24, and specifically binds IGF-II. In further embodiments, the light chain variable region of the bispecific antibody includes the amino acid sequence set forth as SEQ ID NO: 24.

In some embodiments, the bispecific antibody that specifically binds IGF-II includes a heavy chain variable region comprising amino acids 26-33 of SEQ ID NO: 23, amino acids 51-58 of SEQ ID NO: 23, and amino acids 97-109 of SEQ ID NO: 23, and the light chain variable region comprising amino acids 27-32 of SEQ ID NO: 24, amino acids 50-52 of SEQ ID NO: 24, and amino acids 89-98 of SEQ ID NO: 24. In additional embodiments, the bispecific antibody that specifically binds IGF-II includes a heavy chain variable region comprising the amino acid sequence set forth as SEQ ID NO: 23, and a light chain variable region comprising the amino acid sequence set forth as SEQ ID NO: 24.

Thus, in specific non-liming examples, the bispecific antibody includes a heavy chain variable region that includes the amino acid sequence set forth as amino acids 26-33 of SEQ ID NO: 7, amino acids 51-58 of SEQ ID NO: 7 and amino acids 97-109 of SEQ ID NO: 7 a light chain variable region that includes the amino acid sequence set forth as amino acids 27-32 of SEQ ID NO: 8, amino acids 50-52 of SEQ ID NO: 8 and amino acids 89-97 of SEQ ID NO: 8. The antibody also includes a heavy chain variable region comprising amino acids 26-33 of SEQ ID NO: 23, amino acids 51-58 of SEQ ID NO: 23, and amino acids 97-109 of SEQ ID NO: 23, and a light chain variable region comprising amino acids 27-32 of SEQ ID NO: 24, amino acids 50-52 of SEQ ID NO: 24, and amino acids 89-98 of SEQ ID NO: 24.

In additional embodiments, the bispecific antibody includes an antigen binding fragment of the antibody that specifically binds IGF-II only and/or an antigen binding fragment of the monoclonal antibody that specifically bind both IGF-I and IGF-II with picomolar affinity. The antigen binding fragment can be an scFv, Fab, F(ab')$_2$, or an Fv.

A human antibody (or bispecific form thereof) that specifically binds IGF-I and IGF-II with high affinity (for example, picomolar affinity), can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect IGF-I and/or IGF-II by x-ray, emission spectra, or other diagnostic techniques. Examples of labels for polypeptides include, but are not limited to, the following radioisotopes or radionuclides: $^3$H, $^{14}$C, $^{15}$N, $^{35}$S, $^{90}$Y, $^{99}$Tc, $^{111}$In, $^{125}$I, $^{131}$I.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

In one embodiment, the antibody that specifically binds IGF-I and IGF-II inhibits phosphorylation of the insulin-like growth factor type I receptor (IGF-IR). IGF-II binds the IGF-I receptor, and causes tyrosine phosphorylation. Tyrosine phosphorylation of IGF-IR is one of the early responses to potent mitogenic stimuli, such as the binding of IGF-I or IFG-II. The IGF-I receptor binds IGF-I and IGF-II with high affinity to activate cellular proliferation in both normal growth and development and malignant transformation and has tyrosine kinase activity. IGF-IR is highly over expressed in most malignant tissues where it functions as an anti-apoptotic agent by enhancing cell survival. Tyrosine phosphorylation status of proteins can be determined using anti-phosphotyrosine antibodies. In addition, because of the binding specificity of the SH2 domain to phosphorylated tyrosine residues, a specific pattern of tyrosine phosphorylation can be elucidated to determine phosphorylation status.

Immunoassays for determining IGF-IR tyrosine phosphorylation or for measuring total IGF-IR levels are an ELISA or Western blot. If only the cell surface level of IGF-IR is to be measured, the cells are not lysed, and the cell surface levels of IGF-IR are measured using one of the assays described herein. In one example, the immunoassay for determining cell surface levels of IGF-IR includes the steps of labeling the cell surface proteins with a detectable label, such as $^{32}$P, immunoprecipitating the IGF-IR with an anti-IGF-IR antibody and then detecting the phosphorylated IGF-IR.

Nucleic acids encoding the amino acid sequences of the antibodies that bind IGF-II are also provided herein. The nucleic acid molecules can encode a heavy chain variable domain and/or a light chain variable domain. Exemplary nucleic acid sequences are as follows:

```
Heavy chain variable domain (m708.5)
                                         (SEQ ID NO: 11)
CAGGTACAGCTGCAGCAACTAGGGGCTGAAGTGAAGATGCCTGGGTCCT

CGGTGAAGGTCTCCTGCAAGGCTTCTGGAGGCACCTTCAGTAGTTATGCT

ATCAGCTGGGTGCGACAGGCCCCTGGACAAGGGCTTGAGTGGATGGGAG

GGATCATCCCTACCCTTGGTATAGTAAAGTACGCGCAGAAGTTCCAGGG

CAGAGTCACGATTACCGCGGACAAATCCACGAGCACAGCCTACATGGAG

CTGAGCAGCCTGGGATCTGAGGACACGGCCGTGTATTACTGTGCGGGAG

GCCCTAGGGGATACAGCTATAACTTTGACAACTGGGGTCAGGGCACCCT

GGTCACCGTCTCCTCA

Light chain variable domain (m708.5)
                                         (SEQ ID NO: 12)
GACATCCAAATGACCCAGTCTCCATCCTCCCTGTCTGCATCTGTAGGAGA

CAGAGTCACCATCGTTTGCCGGGCAAGTCAGACCATTAGTAGGTATGTA

AATTGGTATCAGCAGAAACCAGGGAAAGCCCCTAAGCTCCTGATCTATG

CTGCATCCAGTTTGCAAAGTGGGGTCTCATCAAGGTTCAGTGGTAGTGGA

TCAGGGACAGAGTTCGCTCTCACCATCAGCAGTCTGCAGCCTGAAGATTT

TGCAACTTATTTCTGTCAACAGACTTACAGTCCCCCGATCACCTTCGGCC

AAGGGACACGACTGGAGATTAAACAA
```

Exemplary nucleic acid sequences are also as follows:

```
m708.6
Heavy chain variable domain
                                         (SEQ ID NO: 19)
CAGGTACAGTTGCAACAACCAGGGGCTGAAGTGAAGATGCCTGGGTCCT

CGGTGAAGGTCTCCTGCAAGGCTTCTGGAGGCACCTTCAGCAGCTATGCT
```

-continued
```
ATCAGCTGGATGCGACAGGCCCCTGGACAAGGGCTTGAGTGGATGGGTG

GGATCATCCCTACCCTTAGTATAGTAAAGTACGCACCGAAGTTCCAGGG

CAGAGTCACGATTACCGCAGACAAATCCACGGGCACAGCCTACATGGAG

CTGAGCAACCTGAGATCTGAGGACACGGCCGTGTATTACTGTGCGGGAG

GCCCTAGGGGATACAGCTATAACTTTGACGAATGGAGTCAGGGCACCAT

GGTCACCGTCTCCTCA
```

Light chain variable domain
(SEQ ID NO: 20)
```
GACATCCAGATGACCCAGTCTCCATCCTCCCTGTCTGCATCTGTAGGAGA

CAGAGTCACCATCGCTTGCCGGGCAAGTCAGACCATTAGTAGGTATTTA

AATTGGTATCAGCAGAAACCAGGGAAAGCCCCTAAGCTCCTGATCTATG

CTGCAACCAGTTTGCAAAGTGGGGTCTCATCAAGGTTCAGTGGCAGTGG

ATCTGAGACAGAGTTCACTCTCACCATCAGCAGTCTGCAGCCTGAAGATT

TTGCAACTTATTTCTGTCAACAGACTTACAGTCCCCCGATCACCTTCGGC

CAAGGGACACGATTGGAGATTAAACGA
``` m708.7
Heavy chain variable domain
(SEQ ID NO: 21)
```
CAGGTACAGTTGCAGCAACCAGGGGCTGAAGTGAAGATGCCTGGGTCCT

CGGTGAAGATCTCCTGTAGGGCTTCTGGAGGCACCTTCAGCAGCTATGCT

ATCAGCTGGGTGCGTCAGGCCCCTGGACAAGGGCTTGAGTGGATGGGAG

GGATCATCCCTACCCTTGGTATAGTAAAGTACTCACAGAAGTTCCAGGG

CAGAGTCACGATTACCGCGGACGAATCCAAGAGCACAGTCTACATGGAA

CTGAGCAGCCTGAGATCTGAGGACACGGCCGTGTATTATTGTGCGGGAG

GCCCTAGGGGATACAGCTATAACTTTGACGAATGGAGTCAGGGCACCCT

GGTCACCGTCTCCTCA
```

Light chain variable domain
(SEQ ID NO: 22)
```
GACATCCAGATGACCCAGTCTCCATCCTCCCTGTCTGCATCTGTAGGAGA

CAGAGTCACCATCGCTTGCCGGGCAAGTCAGACCATTAGTAGGTATTTA

AATTGGTATCAGCAGAAACCAGGGAAAGCCCCTAAGCTCCTGATCTATG

CTGCATCCAATTTGCAAAGTGGGATATCATCAAGGTTCAGTGGCAGTGG

ATCTGGGACAGAGTTCACTCTCACCATCAGCAGTCTGCAGCCTGAAGATT

TTGCAACTTATTTCTGTCAACAGACTTATAGTCCCCCGATCACCTTCGGT

CAAGGGACACGACTGGAGATTAAACGA.
```

In some embodiment the nucleic acid molecules do not include one or both of SEQ ID NO: 13 and SEQ ID NO: 14, as set forth below:

Heavy chain variable domain (m708.2)
(SEQ ID NO: 13)
```
CAGGTACAGCTGCAGCAGCCAGGGGCTGAGGTGAAGAAGCCTGGGTCCT

CGGTGAAGGTCTCCTGCAAGGCTTCTGGAGGCACCTTCAGCAGCTATGC

TATCAGCTGGGTGCGACAGGCCCCTGGACAAGGGCTTGAGTGGATGGGA

GGGATCATCCCTATCCTTGGTATAGCAAACTACGCACAGAAGTTCCAGG

GCAGAGTCACGATTACCGCGGACGAATCCACGAGCACAGCCTACATGGA

GCTGAGCAGCCTGAGATCTGAGGACACGGCCGTGTATTACTGTGCGAGA

GGCCCTAGGGGATACAGCTATAACTTTGACTACTGGGGCCAGGGCACCC

TGGTCACCGTCTCCTCA
```

Light chain variable domain (m708.2)
(SEQ ID NO: 14)
```
GACATCCAGATGACCCAGTCTCCATCCTCCCTGTCTGCATCTGTAGGAGA

CAGAGTCACCATCGCTTGCCGGGCAAGTCAGACCATTAGTAGGTATTTA

AATTGGTATCAGCAGAAACCAGGGAAAGCCCCTAAGCTCCTGATCTATG

CTGCATCCAGTTTGCAAAGTGGGGTCTCATCAAGGTTCAGTGGCAGTGG

ATCTGGGACAGAGTTCACTCTCACCATCAGCAGTCTGCAGCCTGAAGATT

TTGCAACTTATTTCTGTCAACAGACTTACAGTCCCCCGATCACCTTCGGC

CAAGGGACACGACTGGAGATTAAACGA
```

In some embodiments, nucleic acid molecules are provided that encode a bispecific antibody, such as a bispecific antibody including a light chain and a heavy chain that specifically bind IGF-I and IGF-II, and a light chain and a heavy chain that specifically bind IGF-II only. Exemplary nucleic acid sequences are as follows:

Heavy chain nucleotide sequence (m610.27)
(SEQ ID NO: 25):
```
CAAGTGCAGCTGGTGCAGTCTGGGGCTGAGGTGAAGAAGCCTGGGGCCT

CAGTGAAGGTTTCCTGCAAGGCATCTGGATACACCTTCACCAGCTACTAT

ATGCACTGGGTGCGACAGGCCCCTGGACAAGGGCTTGAGTGGATGGGAA

TAATCAACCCTAGTGGTGGTAGCACAAGCTACGCACAGAAGTTCCAGGG

CAGAGTCACCATGACCAGGGACACGTCCACGAGCACAGTCTACATGGAG

CTGAGCAGGCTGAGATCTGACGACACGGCCGTGTATTACTGTGCGAGAG

ATGTGCAGTGGCTGGCATACGGTATGGACGTCTGGGGCCAAGGGACCAC

GGTCACCGTGAGCTCAGCCTCCACCAAGGGCCCATCGGTCTTCCCCCTGG

CACCCTCCTCCAAGAGCACCTCTGGGGGCACAGCGGCCCTGGGCTGCCT

GGTCAAGGACTACTTCCCCGAACCGGTGACGGTGTCGTGGAACTCAGGC

GCCCTGACCAGCGGCGTGCACACCTTCCCGGCTGTCCTACAGTCCTCAGG

ACTCTACTCCCTCAGCAGCGTGGTGACCGTGCCCTCCAGCAGCTTGGGCA

CCCAGACCTACATCTGCAACGTGAATCACAAGCCCAGCAACACCAAGGT

GGACAAGAAAGTTGAGCCCAAATCTTGTGACAAAACTCACACATGCCCA

CCGTGCCCAGCACCTGAACTCCTGGGGGGACCGTCAGTCTTCCTCTTCCC

CCCAAAACCCAAGGACACCCTCATGATCTCCCGGACCCCTGAGGTCACA

TGCGTGGTGGTGGACGTGAGCCACGAAGACCCTGAGGTCAAGTTCAACT

GGTACGTGGACGGCGTGGAGGTGCATAATGCCAAGACAAAGCCGCGGG

AGGAGCAGTACAACAGCACGTACCGTGTGGTCAGCGTCCTCACCGTCCT

GCACCAGGACTGGCTGAATGGCAAGGAGTACAAGTGCAAGGTCTCCAAC

AAAGCCCTCCCAGCCCCCATCGAGAAAACCATCTCCAAAGCCAAAGGGC

AGCCCCGAGAACCACAGGTGTACACCCTGCCCCCATCCCGGGATGAGCT

GACCAAGAACCAGGTCAGCCTGACCTGCCTGGTCAAAGGCTTCTATCCC
```

```
AGCGACATCGCCGTGGAGTGGGAGAGCAATGGGCAGCCGGAGAACAAC

TACAAGACCACGCCTCCCGTGCTGGACTCCGACGGCTCCTTCTTCCTCTA

CAGCAAGCTCACCGTGGACAAGAGCAGGTGGCAGCAGGGGAACGTCTTC

TCATGCTCCGTGATGCATGAGGCTCTGCACAACCACTACACGCAGAAGA

GCCTCTCCCTGTCTCCGGGTAAA

Light chain nucleotide sequence (m610.27)
(SEQ ID NO: 26):
GACATCCAGATGACCCAGTCTCCATCCTCCCTGTCTGCATCTGTAGGAGA

CAGAGTCACCATCACTTGCCGGGCAAGTCAGAGCATTAGTAGCTATTTA

AATTGGTATCAGCAGAAGCCAGGGAGAGCCCCTGACCTCCTGATCAATG

CTGCATCCAGTTTGCAAAGTGGGGTCCCATCAAGGTTCAGTGGCAGTGG

ATCTGGGACCGACTTCACTCTCACCATCAGCAGTCTCCAACCTGAAGATT

TTGCAACTTACTTCTGTCAACAGAGTTACAGTCTTCCGTTCACTTTCGGC

GGAGGGACCAAGGTGGAGATCAAAGGAACTGTGGCTGCACCATCTGTCT

TCATCTTCCCGCCATCTGATGAGCAGTTGAAATCTGGAACTGCCTCTGTT

GTGTGCCTGCTGAATAACTTCTATCCCAGAGAGGCCAAAGTACAGTGGA

AGGTGGATAACGCCCTCCAATCGGGTAACTCCCAGGAGAGTGTCACAGA

GCAGGACAGCAAGGACAGCACCTACAGCCTCAGCAGCACCCTGACGCTG

AGCAAAGCAGACTACGAGAAACACAAAGTCTACGCCTGCGAAGTCACCC

ATCAGGGCCTGAGCTCGCCCGTCACAAAGAGCTTCAACAGGGGAGAGTG
```

Nucleotide molecules encoding the antibodies can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same effector molecule ("EM") or antibody sequence. Thus, nucleic acids encoding antibodies, conjugates and fusion proteins are provided herein.

Nucleic acid sequences encoding the human antibodies that specifically bind IGF-I and IGF-II, antigen binding fragments thereof, and bispecific forms thereof, can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding sequences encoding a human antibody that specifically binds IGF-I and IGF-II with high affinity (such as picomolar affinity), antigen binding fragments thereof, and bispecific forms thereof, can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an antibody of use is prepared by inserting the cDNA which encodes a variable region from an antibody into a vector which comprises the cDNA encoding an effector molecule (EM), such as an enzyme or label. The insertion is made so that the variable region and the EM are read in frame so that one continuous polypeptide is produced. Thus, the encoded polypeptide contains a functional Fv region and a functional EM region. In one embodiment, cDNA encoding an enzyme is ligated to a scFv so that the enzyme is located at the carboxyl terminus of the scFv. In several examples, cDNA encoding a horseradish peroxidase or alkaline phosphatase, or a polypeptide marker of interest is ligated to a scFv so that the enzyme (or polypeptide marker) is located at the amino terminus of the scFv. In another example, the label is located at the amino terminus of the scFv. In a further example, cDNA encoding the protein or polypeptide marker is ligated to a heavy chain variable region of an antibody, so that the enzyme or polypeptide marker is located at the carboxyl terminus of the heavy chain variable region. The heavy chain-variable region can subsequently be ligated to a light chain variable region of the antibody using disulfide bonds. In a yet another example, cDNA encoding an enzyme or a polypeptide marker is ligated to a light chain variable region of an antibody, so that the enzyme or polypeptide marker is located at the carboxyl terminus of the light chain variable region. The light chain-variable region can subsequently be ligated to a heavy chain variable region of the antibody using disulfide bonds.

Once the nucleic acids encoding the antibody, labeled antibody, bispecific form, or fragment thereof are isolated and cloned, the protein can be expressed in a recombinantly engineered cell such as bacteria, plant, yeast, insect and mammalian cells using a suitable expression vector. One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

Polynucleotide sequences encoding the antibody, labeled antibody, bispecific form, or antigen binding fragment thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody, labeled antibody, bispecific form, or antigen binding fragment thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the antibody, labeled antibody or functional fragment thereof can be purified according to standard procedures of the art, including ammonium sulfate precipitation, affinity columns, column chromatography, and the like (see, generally, R. Scopes, *Protein Purification*, Springer-Verlag, N. Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies, bispecific forms, and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., *J. Am. Chem. Soc.* 85:2149-2156, 1963, and Stewart et al., *Solid Phase Peptide Synthesis,* 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

Recombinant human antibodies that specifically bind IGF-I and IGF-II with high affinity, in addition to the anti-IGF-I and IGF-II antibodies disclosed herein can be isolated by screening of a recombinant combinatorial antibody library, preferably a scFv phage display library, prepared using cDNAs of the variable regions of heavy and light chains prepared from mRNA derived from human lymphocytes. Methodologies for preparing and screening such libraries are known in the art. There are commercially available kits for generating phage display libraries (for example, the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; Fuchs et al., Bio/Technology 9:1370-1372, 1991; Hay et al., Hum. Antibod. Hybridomas 3:81-85, 1992; Huse et al., Science 246: 1275-1281, 1989; McCafferty et al., Nature 348:552-554, 1990; Griffiths et al. EMBO J 12:725-734, 1993)

In one embodiment, to isolate additional human antibodies that specifically bind IGF-I and IGF-II, such as a human antibody that specifically binds IGF-I and IGF-II with high affinity (such as at least picomolar affinity), as described herein, is first used to select human heavy and light chain sequences having similar binding activity toward IGF-I and IGF-II, such as using the epitope imprinting methods disclosed in PCT Publication No. WO 93/06213. The antibody libraries used in this method are scFv libraries prepared and screened, using methods such as those as described in PCT Publication No. WO 92/01047, McCafferty et al., Nature 348:552-554, 1990; and/or Griffiths et al., EMBO J 12:725-734, 1993 using human IGF-II as the antigen.

Once initial human variable light chain ($V_L$) and variable heavy chain ($V_H$) segments are selected, "mix and match" experiments, in which different pairs of the initially selected $V_L$ and $V_H$ segments are screened for binding to IGF-I and IGF-II. These assays are performed to select $V_L/V_H$ pair combinations of interest. Additionally, to increase binding affinity of the antibody, the $V_L$ and $V_H$ segments can be randomly mutated, such as within H-CDR3 region or the L-CDR3 region, in a process analogous to the in vivo somatic mutation process responsible for affinity maturation of antibodies during a natural immune response. This in vitro affinity maturation can be accomplished by amplifying $V_H$ and $V_L$ regions using PCR primers complimentary to the H-CDR3 or L-CDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for IGF-I and IGF-II.

Following screening and isolation of an antibody that binds IGF-I and IGF-II with high affinity, such as at least picomolar affinity, from a recombinant immunoglobulin display library, nucleic acid encoding the selected antibody can be recovered from the display package (for example, from the phage genome) and subcloned into other expression vectors by standard recombinant DNA techniques, as described above. If desired, the nucleic acid can be further manipulated to create other antibody fragments, also as described below. To express a recombinant human antibody isolated by screening of a combinatorial library, the DNA encoding the antibody is cloned into a recombinant expression vector and introduced into a mammalian host cells, as described above.

Compositions and Therapeutic Methods

Compositions are provided that include one or more of the antibodies that specifically bind IGF-I and IGF-II with high affinity, such as at least picomolar affinity, antigen binding fragments and bispecific forms that are disclosed herein, and nucleic acids encoding these antibodies, antigen binding fragments and bispecific forms, and a carrier. The compositions can be prepared in unit dosage forms for administration to a subject. The amount and timing of administration are at the discretion of the treating physician to achieve the desired purposes. The antibody can be formulated for systemic or local (such as intra-tumor) administration. In one example, the antibody that specifically binds IGF-I and IGF-II with at least picomolar affinity, antigen binding fragment or bispecific form is formulated for parenteral administration, such as intravenous administration.

The compositions for administration can include a solution of the antibody that specifically binds IGF-I and IGF-II with at least picomolar affinity, antigen binding fragment or bispecific form, or nucleic acids encoding these molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19*th ed.*, Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

In another embodiment, the invention provides a method for inhibiting IGF-IR activity by administering an antibody that binds IGF-I and IGF-II with high affinity, such as at least picomolar affinity, antigen binding fragment or bispecific form thereof, or a nucleic acid encoding one or more of these molecules, to a subject in need thereof. Thus, the antibodies, antigen binding fragments, bispecific forms, and nucleic acids disclosed herein can be used therapeutically. In one example, the subject is human. The antibody may be administered to a non-human mammal expressing an IGF-I and/or IGF-II with which the antibody cross-reacts (such as a primate, or a cynomolgus or rhesus monkey). It should be noted that animal models, such as primate models, can be useful for evaluating the therapeutic efficacy of antibodies disclosed herein.

The antibody, antigen binding fragment, bispecific form or nucleic acid molecule can be administered to a subject having a disease or disorders in which the presence of high levels of IGF-I receptor activity has been shown to be or is suspected of being either responsible for the pathophysiology of the disease or disorder or is a factor that contributes to a worsening of the disease or disorder. Accordingly, inhibition of IGF-I receptor (IGF-IR) activity is expected to alleviate the symptoms and/or progression of the disorder. Such disorders may be evidenced, for example, by an increase in the levels of IGF-IR on the cell surface or by increased tyrosine autophosphorylation of IGF-IR in the affected cells or tissues of a subject suffering from the disorder.

The antibodies disclosed herein that specifically binds IGF-I and IGF-II with high affinity, such as at least picomolar affinity, antigen binding fragments. bispecific forms, or nucleic acids can be administered to slow or inhibit the growth of cells, such as tumor cells. In these applications, a therapeutically effective amount is administered to a subject in an amount sufficient to inhibit growth of a tumor, or to inhibit a sign or a symptom of the tumor. Suitable subjects may include those with a tumor that expresses the IGF-I receptor, such as those suffering from a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer. In one embodiment, a method is provided for the treatment of cancer such as brain, squamous cell, bladder, gastric, pancreatic, breast, head, neck, esophageal, prostate, colorectal, lung, renal, kidney, ovarian, gynecological or thyroid cancer.

A method is also provided herein for the treatment of subjects having multiple myeloma, liquid tumor, liver cancer, thymus disorder, T-cell mediated auto-immune disease, endocronological disorder, ischemia, neurodegenerative disorder, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (such as uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (such as cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (such as renal cell carcinoma, carcinoma of the renal pelvis), or neoplasms of the central nervous system (such as primary CNS lymphoma, spinal axis tumors, brain stem gliomas or pituitary adenomas). In several examples, the human antibody that binds IGF-I and IGF-II with picomolar affinity, antigen binding fragment, or bispecific form, (or a nucleic acid encoding one or more of these molecules) is administered to a patient with prostate cancer, glioma or fibrosarcoma. In additional examples, a human antibody that binds IGF-I and IGF-II with high affinity, such as at least picomolar affinity, antigen binding fragment, or bispecific form (or a nucleic acid encoding one or more of these molecules) is administered to a subject with lung, breast, prostate or colon cancer. In other examples, the method causes the tumor not to increase in weight or volume or to decrease in weight or volume.

Amounts effective for this use will depend upon the severity of the disease and the general state of the patient's health. A therapeutically effective amount of the antibody is that which provides either subjective relief of a symptom(s) or an objectively identifiable improvement as noted by the clinician or other qualified observer. In one example, the amount of the antibody, antigen binding fragment, bispecific form, or nucleic acid is sufficient to inhibit phosphorylation of the IGF-I receptor. These compositions can be administered in conjunction with another chemotherapeutic agent, either simultaneously or sequentially.

Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the invention. Examples of useful COX-II inhibitors include CELEBREX™ (alecoxib), valdecoxib, and rofecoxib. Examples of useful matrix metalloproteinase inhibitors are described in PCT Publication No. WO 96/33172 (published Oct. 24, 1996), PCT Publication No. WO 96/27583 (published Mar. 7, 1996), European Patent Application No. 97304971.1 (filed Jul. 8, 1997), European Patent Application No. 99308617.2 (filed Oct. 29, 1999), PCT Publication No. WO 98/07697 (published Feb. 26, 1998), PCT Publication No WO 98/03516 (published Jan. 29, 1998), PCT Publication No WO 98/34918 (published Aug. 13, 1998), PCT Publication No WO 98/34915 (published Aug. 13, 1998), PCT Publication No WO 98/33768 (published Aug. 6, 1998), PCT Publication No WO 98/30566 (published Jul. 16, 1998), European Patent Publication 606,046 (published Jul. 13, 1994), European Patent Publication 931,788 (published Jul. 28, 1999), PCT Publication No WO 90/05719 (published May 31, 1990), PCT Publication No WO 99/52910 (published Oct. 21, 1999), PCT Publication No WO 99/52889 (published Oct. 21, 1999), PCT Publication No WO 99/29667 (published Jun. 17, 1999), PCT International Application No. PCT/IB98/01113 (filed Jul. 21, 1998), European Patent Application No. 99302232.1 (filed Mar. 25, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997). In one example, the MMP inhibitors do not induce arthralgia upon administration. In another example, the MMP inhibitor selectively inhibits MMP-2 and/or MMP-9 relative to the other matrix-metalloproteinases (such as MMP-1, MMP-3, MMP-4, MMP-5, MMP-6, MMP-7, MMP-8, MMP-10, MMP-11, MMP-12, and MMP-13). Some specific examples of MMP inhibitors of use are AG-3340, RO 32-3555, RS 13-0830, 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide;

(2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxaicyclo[3.2.1]octane-3-carboxylic acid hydroxyamide; 3-endo-3-[4-(4-fluoro-phenoxy)-benzenesulfonylamino]-8-oxa-icyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

The antibodies that specifically bind IGF-I and IGF-II with high affinity, such as at least picomolar affinity, antigen binding fragment thereof, bispecific form thereof, can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in PCT Publication Nos. WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents also include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), C1-1033 (Warner Lambert Parke Davis), C1-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)).

VEGF inhibitors, for example SU-5416 and SU-6668 (Sugen Inc.), SH-268 (Schering), and NX-1838 (NeXstar) can also be used in conjunction with an antibody that specifically binds IGF-II. VEGF inhibitors are described in, for example in PCT Publication No. WO 99/24440 (published May 20, 1999), PCT International Application PCT/IB99/00797 (filed May 3, 1999), PCT Publication No. WO 95/21613 (published Aug. 17, 1995), PCT Publication No. WO 99/61422 (published Dec. 2, 1999), U.S. Pat. No. 5,834,504 (issued Nov. 10, 1998), PCT Publication No. WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), PCT Publication No. WO 99/10349 (published Mar. 4, 1999), PCT Publication No. WO 97/32856 (published Sep. 12, 1997), PCT Publication No. WO 97/22596 (published Jun. 26, 1997), PCT Publication No. WO 98/54093 (published Dec. 3, 1998), PCT Publication No. WO 98/02438 (published Jan. 22, 1998), WO 99/16755 (published Apr. 8, 1999), and PCT Publication No. WO 98/02437 (published Jan. 22, 1998). Other examples of some specific VEGF inhibitors are IM862 (Cytran Inc.); anti-VEGF monoclonal antibody of Genentech, Inc.; and angiozyme, a synthetic ribozyme from Ribozyme and Chiron. These and other VEGF inhibitors can be used in conjunction with an antibody that specifically binds IGF-II.

ErbB2 receptor inhibitors, such as GW-282974 (Glaxo Wellcome pic), and the monoclonal antibodies AR-209 (Aronex Pharmaceuticals Inc.) and 2B-1 (Chiron), can furthermore be combined with the compound of the invention, for example those indicated in PCT Publication No. WO 98/02434 (published Jan. 22, 1998), PCT Publication No. WO 99/35146 (published Jul. 15, 1999), PCT Publication No. WO 99/35132 (published Jul. 15, 1999), PCT Publication No. WO 98/02437 (published Jan. 22, 1998), PCT Publication No. WO 97/13760 (published Apr. 17, 1997), PCT Publication No. WO 95/19970 (published Jul. 27, 1995), U.S. Pat. No. 5,587,458 (issued Dec. 24, 1996), and U.S. Pat. No. 5,877,305 (issued Mar. 2, 1999). ErbB2 receptor inhibitors of use are also described in U.S. Provisional Application No. 60/117,341, filed Jan. 27, 1999, and in U.S. Provisional Application No. 60/117,346, filed Jan. 27, 1999.

Single or multiple administrations of the compositions are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient. In one example, the dose is sufficient to decrease the phosphorylation of the IGF-I receptor.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992) both of which are incorporated herein by reference.

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

Diagnostic Methods and Kits

A method is provided herein for the detection of the expression of IGF-I and/or IGF-II in vitro or in vivo. In one example, expression of IGF-I and/or IGF-II is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a rat, mouse, cow, dog, guinea pig, rabbit, or primate. In one embodiment, the primate is macaque, chimpanzee, or a human.

In several embodiments, a method is provided for detecting a malignancy such as, but not limited to, a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer.

In additional embodiments, a method is provided for detecting multiple myeloma, liquid tumor, liver cancer, thymus disorder, T-cell mediated auto-immune disease, endocronological disorder, ischemia, neurodegenerative disorder, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (such as uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (such as cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (such as renal cell carcinoma, carcinoma of the renal pelvis), or neoplasms of the central nervous system (such as primary CNS lymphoma, spinal axis tumors, brain stem gliomas or pituitary adenomas). A method is also provided for determining the prognosis of a subject with any of the malignancies listed above.

Methods are provided for detecting IGF-I and/or IGF-II in a biological sample, wherein the method includes contacting a biological sample with a human antibody that binds IGF-I and IGF-II with picomolar affinity, antigen binding fragment thereof, or bispecific form thereof, under conditions conductive to the formation of an immune complex, and detecting the immune complex, to detect the IGF-I and/or IGF-II in the biological sample. In one example, the detection of IGF-I and/or IGF-II in the sample indicates that the subject has a malignancy. In another example, the detection of IGF-I and/or IGF-II in the sample indicates that the subject is prone to metastasis.

In one embodiment, the human antibody that specifically binds IGF-I and IGF-II with high affinity, such as at least picomolar affinity, antigen binding fragment or bispecific form is directly labeled with a detectable label. In another embodiment, the human antibody that specifically binds IGF-I and IGF-II with high affinity, such a picomolar affinity (the first antibody, antigen binding fragment thereof, or bispecific form thereof, is unlabeled and a second antibody or other molecule that can bind the human antibody that specifically binds IGF-I and IGF-II (or the antigen binding fragment or bispecific form) is labeled. As is well known to one of skill in the art, a second antibody is chosen that is able to specifically bind the specific species and class of the first antibody. For example, if the first antibody is a human IgG, then the secondary antibody may be an anti-human-1gG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, IGF-I and/or IGF-II can be assayed in a biological sample by a competition immunoassay utilizing IGF-I and/or IGF-II standards labeled with a detectable substance and an unlabeled human antibody that specifically binds IGF-I and IGF-II with high affinity, such as picomolar affinity, an antigen binding fragment thereof or a bispecific form thereof. In this assay, the biological sample, the labeled IGF-I and/or IGF-II standards and the human antibody that specifically bind IGFI and IGF-II (or the antigen binding fragment or bispecific form) are combined and the amount of labeled IGF-I and/or IGF-II standard bound to the unlabeled antibody is determined. The amount of IGF-I and/or IGF-II in the biological sample is inversely proportional to the amount of labeled IGF-I and/or IGF-II standard bound to the antibody that specifically binds IGF-I and IGF-II (or bound to the antigen binding fragment or bispecific form).

The immunoassays and method disclosed herein can be used for a number of purposes. In one embodiment, the human antibody that specifically binds IGF-I and IGF-II, antigen binding fragment, or bispecific form, can be used to detect the production of IGF-I and/or IGF-II in cells in cell culture. In another embodiment, the antibody can be used to detect the amount of IGF-I and/or IGF-II in a biological sample.

Increased expression of IGF is associated with several types of cancer, including a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer. Thus, the level of IGFs can be used to diagnose, or determine the prognosis of, a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer, in a subject.

In one embodiment, a kit is provided for detecting IGF-I and IGF-II in a biological sample, such as a blood sample. Kits for detecting a polypeptide will typically comprise a human antibody that specifically binds IGF-I and IGF-II, such as any of the antibodies disclosed herein, including the antigen binding fragments and bispecific forms. In some embodiments, an antibody fragment, such as an Fv fragment is included in the kit. For in vivo uses, the antibody can be a scFv fragment. In a further embodiment, the antibody is labeled (for example, with a fluorescent, radioactive, or an enzymatic label).

In one embodiment, a kit includes instructional materials disclosing means of use of an antibody that specifically binds IGF-I and IGF-II (or the antigen binding fragment or bispecific form thereof). The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting IGF-I and/or IGF-II in a biological sample generally includes the steps of contacting the biological sample with an antibody, antigen binding fragment or bispecific antibody which specifically reacts, under immunologically reactive conditions, to IGF-I and IGF-II polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies, antigen binding fragments, and bispecific forms can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbant assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the human antibodies that specifically bind IGF-II, antigen binding fragments and bispecific forms, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The disclosure is illustrated by the following non-limiting Examples.

EXAMPLES

The isolation, maturation and characterization of a phage-derived human monoclonal antibody (m708.5) which bound with very high affinity to IGF-I ($K_D$=200 pM) and IGF-II ($K_D$=60 pM) is disclosed herein. This antibody potently inhibited signal transduction mediated by the IGF-IR interaction with both IGF-I and IGF-II, resulting in the inhibition of phosphorylation of IGF-IR and cancer cell growth.

Example 1

Materials and Methods

Phage Display Fab library panning: Recombinant human IGF-I was used to screen a human naive Fab phage library containing $10^{10}$ unique clones using protocols and reagents similar to those that were used previously (Zhu and Dimitrov, Methods Mol Biol, 2009. 525: p. 129-42). Recombinant human IGF-I was conjugated onto magnetic beads (Invitrogen) as target for the library panning. The 10 µg of the antigen was used in the first round of panning. The $10^{12}$ amplified phages were used for the panning After 10 washes, bound phages on the beads were directly used to infect exponentially growing TG1 cells and rescued by M13KO7 helper phage. Panning was repeated two rounds by using 2 µg of antigen each round. Two hundred individual colonies after the third round were picked and inoculated into 2YT medium in 96-well plate for phage ELISA screening.

Generation and Selection of the Light Chain-shuffled Phage Display Library: The original human Fab phage display library was used as the source of the $V_L$ repertoire in the shuffled library. The phagemid preparation from the original library was first digested with restriction enzymes NcoI and SpeI and followed by electrophoresis on an agarose gel to delete the entire $V_H$ repertoire. The gene encoding the $V_H$ domain of clone m708 was amplified by error-prone PCR kit from Stratagene to introduce random mutations and then fused with $CH_1$ gene fragment by SOE PCR. The fused fragment was digested with NcoI and Spe I, purified from agarose gel and then ligated into the purified backbone vector to create the $V_L$-shuffled Fab repertoire. *E. coli* TG1 cells were transformed with the ligation mixtures by electroporation. The transformed TG1 cells were plated on 2YT agar plates containing 100 µg/ml ampicillin and 2% glucose. After incubation overnight at 37° C., all of the colonies grown on the plates were scraped into 5 ml of 2YT medium containing 2% glucose and 100 µg/ml ampicillin, mixed with 1.2 ml of 50% glycerol (final concentration 10%), aliquoted, and stored at −70° C. as the mutant library stock.

The library stock was grown to log phase in 20 ml of 2YT medium, rescued with M13KO7 helper phage, and amplified overnight in 2YT medium containing 100 µg/ml of ampicillin and 50 µg/ml of kanamycin at 30° C. The phage preparation was precipitated in 4% PEG8000 with 0.5 M NaCl and dissolved in 1 ml of PBS as phage library stock. Two rounds of biopanning were performed on human IGF-I conjugated magnetic beads as described in the original library panning.

Mutagenesis by Error-Prone PCR: Error-prone PCR of the entire scFv gene was performed using STRATAGENE GENEMORPH® II Random Mutagenesis Kit according to the instructions of the manufacturer. Briefly, PCR was done in a 50-µL reaction containing 1× Mutazyme II reaction buffer, 0.5 µM each of primers RDlinker1F (5' GATATATCCATGGCCCAGGCGGCC 3' (SEQ ID NO: 15) and ERRORR (5' ACCACTAGTTGGGCCGGCCTG 3' (SEQ ID NO: 16)), 0.2 mM (each) dNTPs, 1 ng of DNA template, 2 µM 8-oxo-deoxyguanosine triphosphate, 2 µM 2'-deoxy-p-nucleoside-5'-triphosphate, and 2.5 U of Mutazyme II DNA polymerase. The reaction mixtures were denatured at 95° C. for 2 min, cycled 35 times at 95° C. for 1 min, 60° C. for 1 min, and 72° C. for 1 min, and finally extended at 72° C. for 10 min. The PCR products were purified by 1% agarose gel electrophoresis and each amplified in four 100-µL PCR reactions containing 1× Accuprime PCR reaction mix (Invitrogen), 1 µM of primers YDRDF (5' CTTCGCTGTTTTTCAATATTTTCTGTTATTGCTTCA-GTTTTG GCCCAGGCGGCC 3' (SEQ ID NO: 17)) and YDRDR (5' GAGCCGCCACCCTCAGAACCGCCAC-CCTCAGAGCCACCACTAGTTGGGC CGGCCTG 3' (SEQ ID NO: 18)), 120 ng of error-prone PCR product, and 2.5 U of Accuprime pfx DNA polymerase (Invitrogen). The reactions were thermally cycled at the same conditions except that 30 cycles were used. Reaction products were purified by 1% agarose gel electrophoresis and concentrated with ultrafilter in water.

Construction of Yeast Displayed Mutant Library: The plasmid used for library construction, pYD7, was modified from pCTCON2 (Hackel et al., J Mol Biol, 2008. 381(5): p. 1238-52; Chao, G et al. Nat Protoc, 1(2): 755-768). Two SfiI restriction sites of pYD7 before and after the scFv matched the cloning sites of the pComb3X vector. This allowed fragments to be shuttled between the yeast vector and pComb3x. To avoid interference of agglutinin protein aga2p, it was also converted to 3' end of antibody fragment.

The vector was digested with SfiI. Multiple aliquots of 24 µg of mutagenized scFv gene and 8 µg of plasmid vector were combined with 20-30 µL of water. The pYD7-scFv libraries were then transformed into EBY100 using electroporation transformation method (Benatuil et al., Protein Eng Des Sel, 2010. 23(4): p. 155-9). Homologous recombination of the linearized vector and degenerated insert DNA yielded intact plasmid (Hackel, supra). Briefly, the 10 ml of EBY100 yeast cells in YPD media (10 g/l yeast nitrogen base, 20 g/l peptone and 20 g/l glucose) were grown overnight. The culture was inoculated into fresh 100 ml of YPD media to reach $OD_{600}$ of 1.6 before collecting by centrifugation. The cell pellet was washed twice with 50 ml of cold water, and once with 50 ml cold electroporation buffer (1 M sorbitol/1 mM $CaCl_2$). Cells were conditioned in 20 ml of 0.1 M LiAc/10 mM DTT by incubation in culture at 30° C. for 30 minutes, washed one more time with 50 ml of electroporation buffer, then resuspended in the same buffer to reach 1 ml volume. Each electroporation mixture included 400 µl of yeast cell suspension, 4 µg linearized vector, and 12 µg insert DNA. Cells were electroporated at 2.5 kV and 25 mF in BioRad GenePulser cuvettes (0.2 cm electrode gap). After electroporation, cells were resuspended in 20 ml of 1:1 (y:y) mix of 1 M sorbitol. YPD media and incubated at 30° C. for 1 h. Finally, the cells were collected and cultured in SDCAA media (20 g/l glucose, 6.7 g/l yeast nitrogen base without amino acids, 5.4 g/l $Na_2HPO_4$, 8.6 g/l $NaH_2PO_4.H_2O$ and 5 g/l casamino acids) at 30° C. with 250 rpm shaking for 1-2 days.

Selection of Binders from the Yeast Libraries: The yeast libraries were grown as previously described (Chao et al., Nat Protoc, 2006. 1(2): p. 755-68). Typically yeast were grown in SDCAA media for 18 h at 30° C. and then transferred to SG/RCAA media (20 g/l galactose, 20 g/l Raffinose, 1 g/l glucose, 6.7 g/l yeast nitrogen base without amino acids, 5.4 g/l $Na_2HPO_4$, 8.6 g/l $NaH_2PO_4.H_2O$ and 5 g/l casamino acids) for 16-18 h at 20° C. in culture volumes appropriate for the size of the library.

The methodology for generating and isolating higher affinity mutants was as described (Chao et al., supra; Boder et al., Proc Natl Acad Sci USA, 2000. 97(20): p. 10701-5; Boder et al., Methods Enzymol, 2000. 328: p. 430-44). Antigen concentrations are chosen based on the expected dissociation constant ($K_D$) of the parental. The antigen incubation volume must be large enough to allow at least antigen excess of tenfold over amounts of scFv displayed on yeast. Antigen incubation times were based to come to equilibrium calculated as the reference (Garcia-Rodriguez, et al., Nat Biotechnol, 2007. 25(1): p. 107-16). Before FACS selection, yeast cells ($1 \times 10^9$) were incubated with 10 µg-IGF-I conjugated magnetic beads for 1 h at room temperature in PBSA buffer (0.1% BSA in PBS), followed by separation with magnetic stand. The isolated beads were washed 3 times with PBSA buffer, put into 10 ml of SDCAA media and grown overnight in a 30° C. shaker with 250 rpm. The yeast cells recovered from magnetic beads were induced in SG/RCAA media for 18 h at 20° C. with 250 rpm shaking. For $1^{st}$ round (3 FACS selection), the first selection, approximately $1 \times 10^8$ yeast cells were pelleted, washed twice with PBSA buffer and resuspended in 1 ml PBSA buffer with 3 nM biotinylated IGF-I and a 1:100 dilution of mouse anti-c-myc antibody (Invitrogen). After incubation, yeast cells were washed 3 times and then resuspended in 1 ml PBSA buffer. Both 1:50 dilution of R-phycoerythrin conjugated Streptavidin (Invitrogen) and Alexa488 conjugated goat anti-mouse IgG antibody (Invitrogen) was added to yeast cells, incubated at 4° C. for 30 min, and washed 3 times with PBSA buffer again, and then resuspended in PBSA buffer for flow cytometric sorting. Sort gates were determined to select only population with higher antigen binding signals. Collected cells were grown overnight in SDCAA media at 30° C. and induced in SG/RCAA for the next round of sorting. For the next two selections, approximately $1-2 \times 10^7$ yeast cells were used for staining with 1 nM and 0.3 nM biotinylated IGF-I, respectively.

Two and three selections were performed in the $2^{nd}$ and $3^{rd}$ round. Yeast cells were pelleted, washed in PBSA buffer, resuspended in PBSA buffer with biotinylated IGF-I (ranging from 3 nM to 0.1 nM) and mouse anti-cmyc antibody, and incubated on ice. Cells were then washed with PBSA twice and resuspended in 1 ml PBSA with R-phycoerythrin conjugated Streptavidin and Alexa488 conjugated goat anti-mouse antibody.

After the $1^{st}$ and $2^{nd}$ round, yeast plasmids were isolated using ZYMOPREP™ Yeast Plasmid Miniprep II kit (Zymo Research) according to the manufacturer's instructions and used for templates of library construction. Cells from round 3 spread on SDCAA plates. Plasmids from the $3^{rd}$ round were prepared, sequenced and characterized.

Conversion to IgG1: Fab and scFv were cloned into pDR12, which allows simultaneous expression of the heavy chain and light chains. Briefly, the heavy chain variable region was first cloned into pDR12 via XbaI and SacI sites. The light chain sequence (VL+CL) was then cloned into pDR12 via HindIII and EcoRI sites.

Expression of Fab, scFv and IgG1: Fab and scFv were expressed and purified as previously described (Zhu et al., Proc Natl Acad Sci USA, 2007. 104(29): p. 12123-8; Zhao et al., Protein Expr Purif, 2009. 68(2): p. 190-5). HB2151 cells were transformed with pComb3x plasmid containing Fab or scFv sequences. Single fresh colonies were inoculated into 2YT medium containing 100 μg/mL ampicillin and 0.2% glucose. The culture was grown at 37° C. with 250 rpm until A600 reached 0.5. Isopropyl-L-thio-h-D-galactopyranoside (final concentration 0.5 mM) was added to induce expression. After overnight growth at 30° C., the bacteria were centrifuged at 5,000×g for 15 minutes. Bacteria were centrifuged at 5,000×g for 15 minutes. The pellet was resuspended in PBS with polymyxin B (10,000 units/mL). Soluble Fab was released from periplasm by incubating at 30° C. for 30 minutes. The extract was clarified at 15,000×g for 30 minutes. The clear supernatant was recovered for purification on Ni-NTA column Recombinant Fabs have FLAG™ and His tags.

IgGs were expressed in 293 FREESTYLE™ cells. CELLFECTIN® was used to transfect 293 FREESTYLE™ cells according to the instructions of the manufacturer (Invitrogen). Four days posttransfection, the culture supernatant was harvested. IgGs were purified on protein G column.

ELISA Binding Assay: Antigens (50 ng) per well were coated on 96-well ELISA plates overnight at 4° C. For phage ELISA, ~$1 \times 10^{10}$ phages were incubated with antigen for 1 h. Bound phage was detected with anti-M13-HRP polyclonal antibody (Pharmacia, Piscataway, N.J.). For Fab and IgG ELISA, Fabs and IgGs with different dilutions were incubated with antigens for 1 hour. Bound Fabs were detected with anti-FLAG-HRP mAb (1:3,000; Sigma). Bound IgGs were detected with anti-human Fc-HRP mAb (1:2,000; Invitrogen). The 2,2'-azino-bis-(3-ethylbenzthiazoline-6-sulfonic acid) substrate was added and the reaction was read at 450 nm.

Affinity Measurement of Yeast-Displayed scFv: The equilibrium dissociation constant for a clone was determined essentially as described (Chao et al, Nat Protoc, 2006. 1(2): p. 755-68). Briefly, the deserved yeast clone was grown and induced as for FACS analysis. The $1 \times 10^5$ yeast cells were incubated with biotinylated IGF-I at different concentrations and a 1:100 dilution of mouse anti-c-myc antibody for 3 h at room temperature in PBSA buffer. Six to eight different concentrations of biotinylated antigens were chosen around the equilibrium dissociation constant. Incubation volumes and number of yeast stained were chosen to keep the number of antigen molecules in tenfold excess above the number of scFv. Cells were then washed once in PBSA buffer. The cells were stained with a 1:50 dilution of R-phycoerythrin conjugated Streptavidin and Alexa488 conjugated goat anti-mouse antibody on ice in the dark, then washed again and resuspended in 0.5 ml wash buffer. Analysis was performed using a BD Bioscience FACS.

Affinity Determination by Surface Plasmon Resonance: Interactions between various isolated antibodies and IGF-I and IGF-II were analyzed by surface plasmon resonance technology using a Biacore X100 instrument (GE healthcare). IGF-I or IGF-II was covalently immobilized onto a sensor chip (CM5) using carbodiimide coupling chemistry. A control reference surface was prepared for nonspecific binding and refractive index changes. For analysis of the kinetics of interactions, varying concentrations of antibodies were injected at flow rate of 30 μl/min using running buffer containing 150 mM NaCl, 3 mM EDTA, and 0.005% P-20 (pH 7.4). The association and dissociation phase data were fitted simultaneously to a 1:1 Langumir global model by using the nonlinear data analysis program BIAevaluation 3.2. All the experiments were done at 25° C.

Competition Assay: IgG m708.5 was incubated with 5 nM biotinylated IGF-I and biotinylated 1 nM IGF-II at room temperature for 20 min, respectively. Then, the mixtures were added to $5 \times 10^5$ MCF-7 cells in 50 μl PBSA buffer and incubated for 30 min on ice. After one washing, cells were incubated with a 1:50 dilution of R-phycoerythrin conjugated Streptavidin for 30 min on ice, then washed again and resuspended in 0.5 ml PBSA buffer. Analysis was performed using a BD Bioscience FACS. Irrelevant anti-gp41 MPER scFv-3A2a and anti-Nipah/Hendra viruses IgG-m102.4 (Zhu et al., J Infect Dis, 2008. 197(6): p. 846-53) were chosen as negative controls.

Phosphorylation Assay: MCF-7 cells were seeded in a six-well plate at $1 \times 10^6$ cells per well in the complete growth medium (DMEM with 10% FBS, 100 U/ml penicillin, 100 μg/ml streptomycin). After overnight culture, cells were rinsed with serum-free DMEM and then cultured in serum-free DMEM for 5 hours. The treatment medium was made by adding 1 nM IGF-I or 5 nM IGF-II and various concentrations of IgG in serum-free DMEM. After pre-incubation for 30 min at RT, the treatment medium was added to cells. Twenty minutes after addition of ligands and antibodies, cells were chilled on ice, rinsed in cold PBS, and lysed in 1 mL of lysis buffer [50 mmol/L HEPES (pH 7.4), 150 mmol/L NaCl, 10% glycerol, 1% Triton X-100, 1.5 mmol/L MgCl2, 2 mmol/L sodium vanadate, and protease inhibitors]. Lysates were kept on ice for 30 minutes, followed by centrifugation at 17,000×g for 30 minutes. The supernatant was used for immunoprecipitation: 20 μL of protein G Sepharose 4B and 3 μg of rabbit anti-IGFIR β IgG (C-20, Santa Cruz) at 4° C. overnight. After extensive wash, the immunoprecipitates were run on 4% to 12% NUPAGE, transferred to polyvinylidene difluoride membrane, and blotted with anti-phosphotyrosine mAb PY20 (Sigma). The membrane was stripped and reprobed with C-20 polyclonal antibody to detect total IGFIR in the immunoprecipitates. A similar procedure was used to detect the phosphorylation of insulin receptor but immunoprecipitation and Western blots were done with rabbit anti-IR β pAb (C-19, Santa Cruz) which is specific to insulin receptor.

Cell Growth Assay: MCF-7 cells were seeded in a 96-well plate at $1 \times 10^4$ cells per well in complete growth medium. After overnight culture, cells were rinsed with serum-free DMEM. Various concentrations of IgGs were mixed with IGF-I (2.5 nM) and IGF-II (2.5 nM) and incubated for 20 min at room temperature. Then, 100 µl of the mixture was added each well immediately. Cells were allowed to grow for 3 days, and 20 µl of MTS substrate (Promega) was added to detect viable cells. Plates were incubated at 37° C. for 1 h and monitored at $A_{450}$ nm. Cells in serum-free medium with IGF ligands were as positive control. Cells in serum-free medium without IGF ligands were as blank control.

Example 2

Identification of m708.2 Cross-Reactive IGF-I and IGF-II

To develop human mAbs that specifically bind IGF-I, a large (size ~$10^{10}$) naive human Fab phage-displayed library was utilized. Recombinant human IGF-I was conjugated to magnetic beads and used as an antigen for panning After three rounds of panning, more than 200 random individual phage clones were screened by phage ELISA against IGF-I. Clones that exhibited significant binding to IGF-I were sequenced. Finally, three clones with unique sequences were found. They were expressed in bacteria as soluble Fabs, purified, and tested for binding activity in ELISA. Two Fabs, designated m705 and m706 showed binding specifically to IGF I only, while one Fab, m708, exhibited significant levels of binding to both IGF-I and IGF-II in ELISA (FIG. 1). Thus, m708 was selected for affinity maturation by light chain shuffling.

Two rounds of panning of the light chain shuffled library (containing 2×$10^8$ independent clones) against IGF-I conjugated magnetic bead were performed and 200 clones from the second round of panning were screened by phage ELISA. Of these 200 clones, only m708.2 showed markedly higher binding to both IGF-I and IGF-II than parental m708 version.

Example 3

Construction of Libraries of m708.2 Mutants Displayed on Yeast

The binding affinity of m708.2 was further improved by utilizing yeast display technique. The scFv gene constructed from m708.2 was randomly mutagenized by employing error-prone PCR strategy. The mutant library was incorporated into a yeast display system by homologous recombination with a vector containing C-terminal Aga2 protein and c-myc tag. Usually, library transformation yielded 5×$10^7$ clones per microgram vector DNA. High mutation frequencies (~1%) can also be achieved by using 1 ng of target DNA with 35 PCR cycles. In order to obtain large amounts of DNA insert and avoid improperly incorporation at the site of homologous recombination, a small purified DNA of the first PCR reaction was re-amplified in a second PCR reaction. Thus, 30-40% of the transformed cells displayed scFvs verified by flow cytometry analysis.

Example 4

Selection of an Affinity Matured scFv (m708.5)

Figure 2:
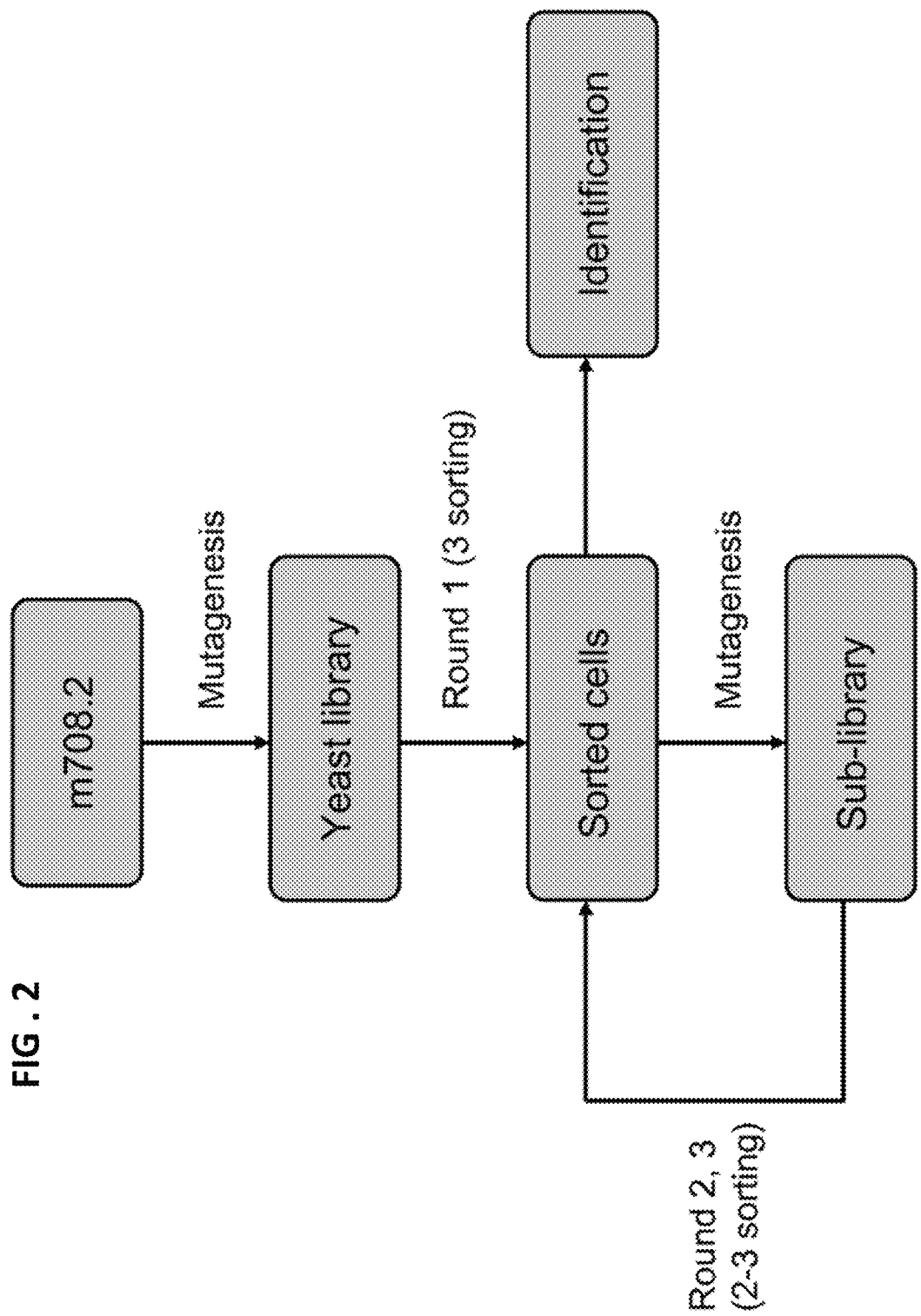
FIG. 2 is a schematic diagram of an affinity maturation scheme. The mutagenesis yeast library was constructed from parental m708.2. The library was subjected to screen on IGF-I conjugated magnetic beads once and sorted three times by FACS for binding to IGF-I. The sorted population was mutated by error-prone PCR of the entire gene to yield a new sub-library. The process of sorting and mutagenesis was then cyclically repeated. The rounds of affinity maturation are named for the number of mutagenesis cycles, thus sorting of the parental library is round 1, followed by round 2 and 3. The highest affinity clone present in the final round of maturation was identified and sequence analysis.
Figure 3A:
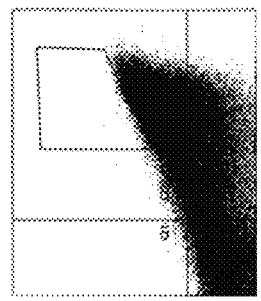
FIGS. 3A-3H are a set of plots showing FACS selection for affinity maturation. Yeast libraries were labeled with mouse anti-c-myc antibody followed by goat anti-mouse dye as well as biotinylated IGF-I followed by streptavidin-dye (a, b, c). During three FACS selections of round 1, yeast cells were stained with concentrations of IGF-I at 3 nM, 1 nM and 0.3 nM, respectively (d, e). During two FACS selections of round 2, yeast cells were stained with concentrations of IGF-I at 3 nM, and 0.3 nM, repectively (f, g, h). During three FACS selections of round 3, yeast cells were stained with concentrations of IGF-I at 1 nM. 0.5 nM and 0.1 nM. The 0.1-0.3% cells were selected from sort gates.
Figure 3B:
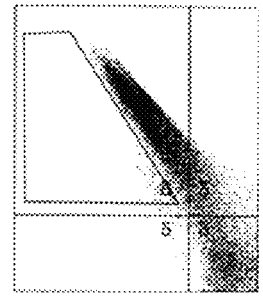
Figure 3C:
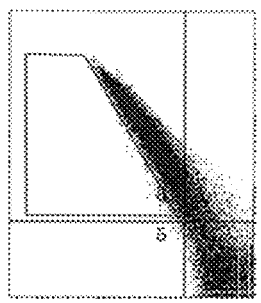
Figure 3D:
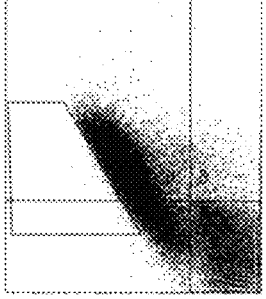
Figure 3E:
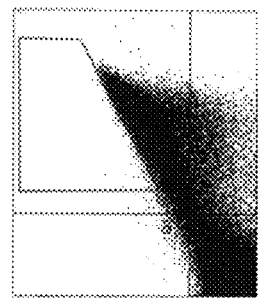
Figure 3F:
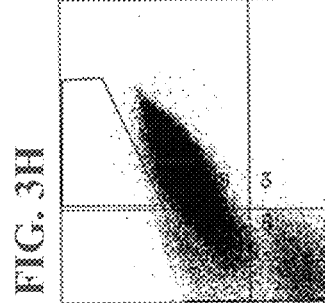
Figure 3G:
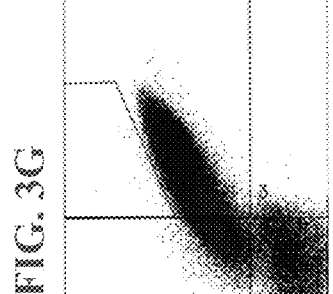
Figure 3H:
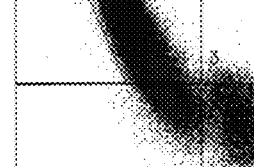

Yeast libraries of relatively large (up to $10^9$) size were generated and therefore $10^9$-$10^{10}$ cells should be sorted (Blaise et al., Gene, 2004. 342(2): p. 211-8). Magnetic separation methods are capable of processing large numbers of cells. Before FACS sorting, the mutagenesis yeast libraries were subjected to one round of selection by using IGF-I conjugated magnetic beads (Yeung et al., Biotechnol Prog, 2002. 18(2): p. 212-20). This allowed elimination of non-expression and weak binding yeast cells from the libraries. The affinity maturation scheme is shown in FIG. 2. Briefly, a yeast library of m708.2 mutants was constructed. The library was screened on IGF-I conjugated magnetic beads once and sorted several times by FACS for binding to IGF-I. The sorted population was mutated by error-prone PCR of the entire gene to yield a new sub-library. The process of sorting and mutagenesis was then cyclically repeated. The highest affinity clones from the final round of maturation were identified and their sequences analyzed.

One dominant clone, m708.5, was identified by sequence analysis. When compared with m708.2, m708.5 had two amino acid substitutions in CRD-H2, two amino acid substitutions in CDR-H3 and nine amino acid substitutions in the framework region (Table 1).

TABLE 1

Sequences of cross-reactive antibodies to IGF-I and IGF-II

| Clone | H1 | H2 | H3 |
|---|---|---|---|
| m708.2 | GGTFSSYA | IIPILGIA | ARGPRGYSYNFDY |
| m708.5 | -------- | ---T---V | -G---------N |

Antigen-binding loops H1, H2 and H3 (VH) indicate the loop residues with CDRs that were subjected to mutation. For the H-CDR sequences of m708.5, see amino acids 26-33 of SEQ ID NO: 7 (H1), amino acids 51-58 of SEQ ID NO: 7 (H2), and amino acids 97-109 of SEQ ID NO: 7 (H3). For the H-CDR sequences of m708.2, see amino acids 26-33 of SEQ ID NO: 9 (H1), amino acids 51-58 of SEQ ID NO: 9 (H2), amino acids 97-109 of SEQ I DNO: 9 (H3).

These substitutions resulted in a remarkable improvement of affinity, while the antibody surprisingly still retained cross-reactivity. The affinities of m708.2 and m708.5 were calculated by incubating each yeast-displayed scFv with varying concentrations of biotinylated IGF-I or IGF-II. The affinity of yeast-displayed m708.5 scFv for IGF-I improved 39-fold compared to m708.2 ($1 \times 10^{-10}$ M versus $3.9 \times 10^{-9}$ M, respectively), whereas its affinity for IGF-II increased 27-fold, from $1.1 \times 10^{-9}$ M to $4.1 \times 10^{-11}$ M (Table 2). Similar values were obtained for isolated soluble scFvs as measured by Biacore: $2 \times 10^{-10}$ M for IGF-I and $6.1 \times 10^{-11}$ M for IGF-II, compared to m708.2 scFv ($2.2 \times 10^{-9}$ M for IGF-I and $1.8 \times 10^{-9}$ M for IGF-II) (Table 2).

TABLE 2

Affinity and binding kinetics of cross-reactive antibodies to IGF-I and IGF-II

| Antibody | Antigen | FACS $K_D$ ($M^{-1}$) | Biacore $k_{on}$ ($M^{-1}s^{-1}$) | Biacore $k_{off}$ ($s^{-1}$) | Biacore $K_D$ ($M^{-1}$) |
|---|---|---|---|---|---|
| m708.2 scFv | IGF-I | $3.9 \times 10^{-9}$ | $1.1 \times 10^6$ | $2.4 \times 10^{-3}$ | $2.2 \times 10^{-9}$ |
| | IGF-II | $1.1 \times 10^{-9}$ | $2.3 \times 10^5$ | $4.0 \times 10^{-4}$ | $1.8 \times 10^{-9}$ |
| m708.5 scFv | IGF-I | $1.0 \times 10^{-10}$ | $1.4 \times 10^6$ | $2.8 \times 10^{-4}$ | $2.0 \times 10^{-10}$ |
| | IGF-II | $4.1 \times 10^{-11}$ | $4.1 \times 10^6$ | $2.5 \times 10^{-6}$ | $6.1 \times 10^{-11}$ |

Therefore, the cross-reactive antibody m708.2 was successfully matured to picomolar affinities for both IGF-I and IGF-II.

Example 5

Avidity of IgG1 m708.5

Figure 4A:
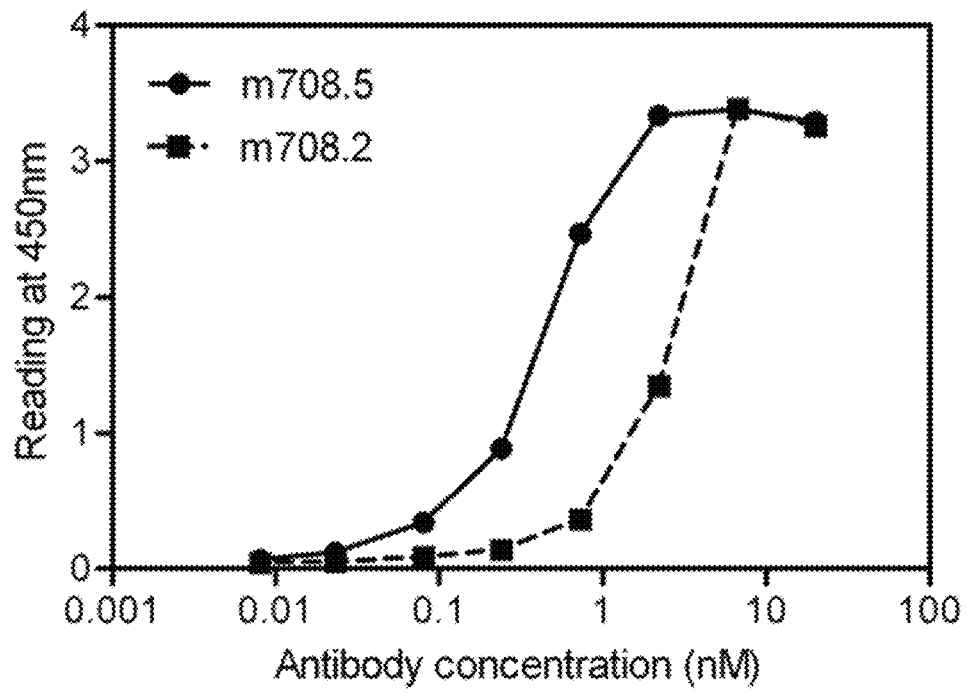
FIGS. 4A and 4B is a set of graphs showing a binding comparison of IgGs of m708.2 and m708.5. IgGs of m708.2 and m708.5 with serial dilutions were added to wells coated with IGF-I (a) and IGF-II (b). Bound IgGs were detected with a HRP conjugated anti-human Fc antibody and measured as optical densities at 450 nm.
Figure 4B:
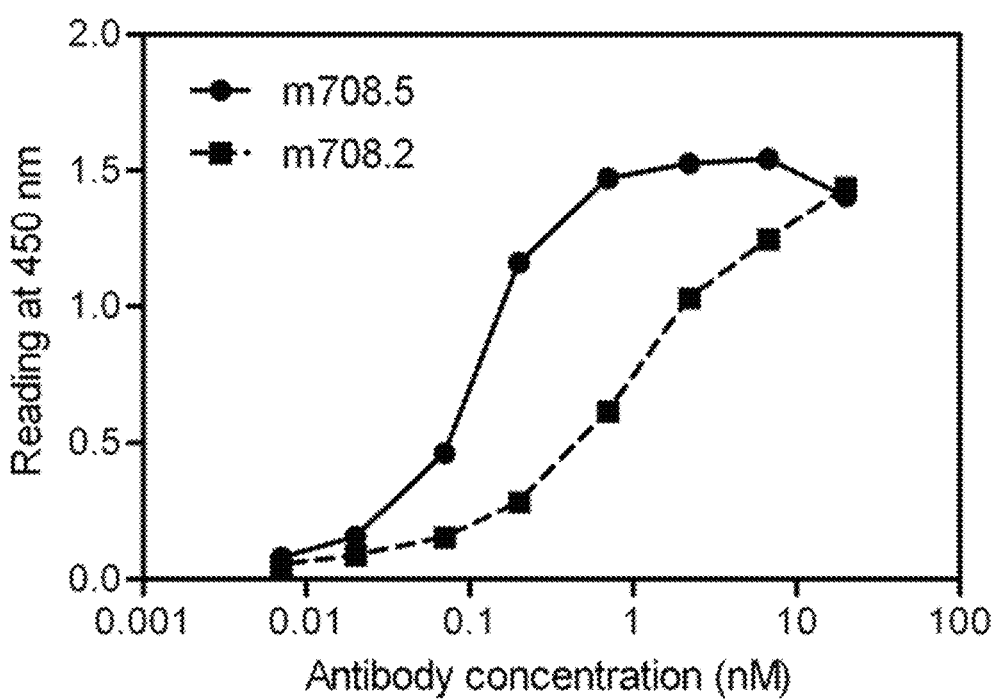
Figure 5B:
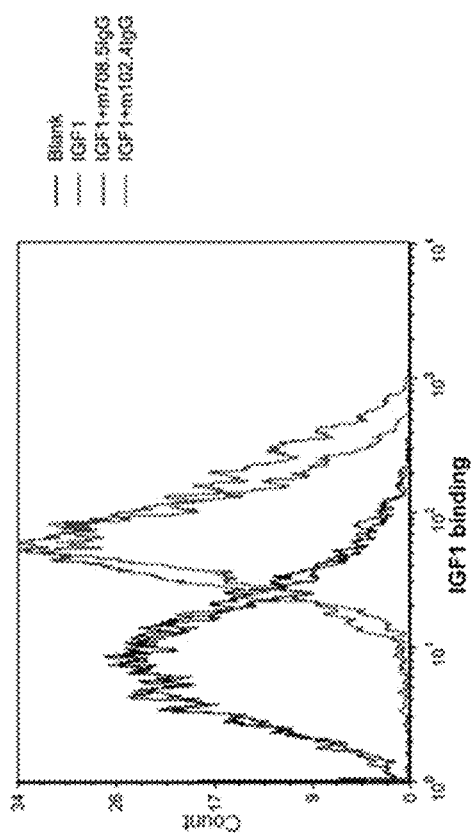
FIG. 5A to 5D is a set of graphs showing inhibition of IGF-I and IGF-II binding to MCF-7 cells by m708.5 (a-b). M708.5 scFv and control 3A2a scFv were pre-incubated with biotinylated IGF-I and biotinylated IGF-II for 20 min at room temperature. Then mixtures were incubated with MCF-7 cells for 30 min on ice (c-d). M708.5 IgG and control m102.4 IgG were pre-incubated with biotinylated IGF-I and biotinylated IGF-II for 20 min at room temperature. The mixtures then were incubated with MCF-7 cells for 30 min on ice. After the staining of R-phycoerythrin conjugated Streptavidin for 30 min on ice, cells were detected by flow cytometry.
Figure 5D:
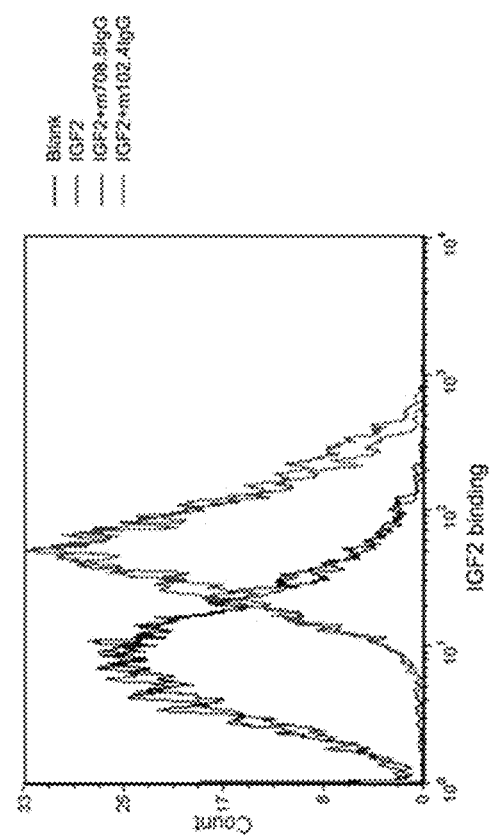
Figure 5A:
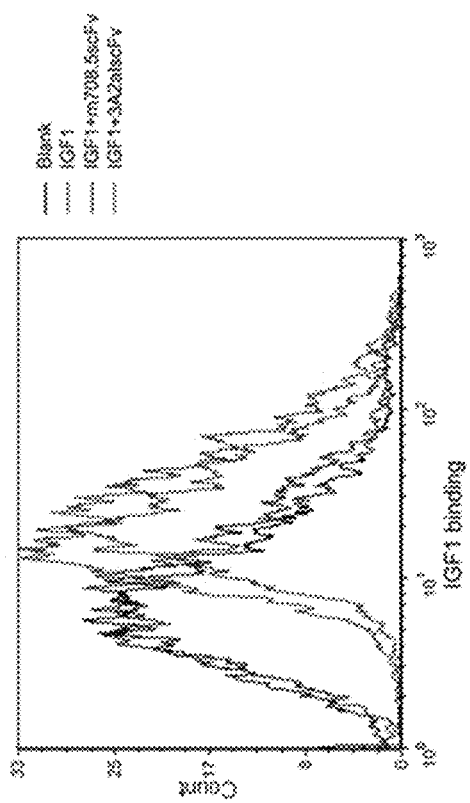
Figure 5C:
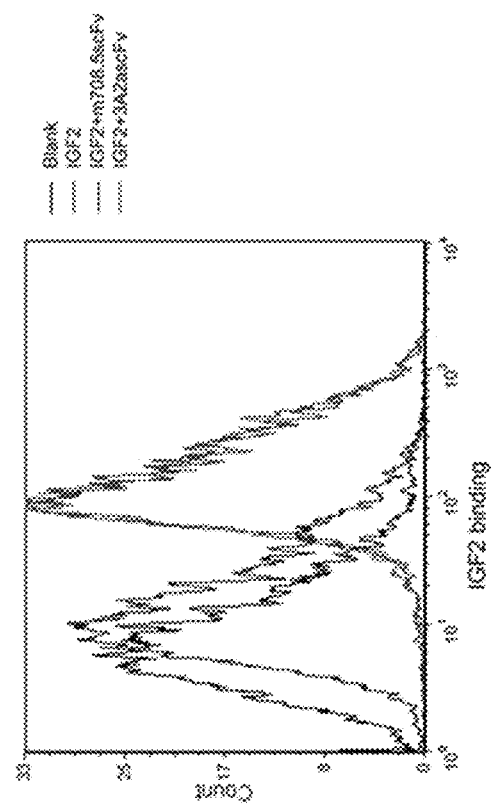

To determine whether changes in affinity for scFv were observed in IgG format, the scFv was converted to IgG. As with scFv, m708.5 IgG showed increased affinity for IGF-I and IGF-II. The effective $K_D$ of m708.5 for IGF-I and IGF-II was 1000-fold and 60-fold higher than the $K_D$ for the scFv, respectively. The measured $K_D$ ($<10^{-12}$ M) is beyond the sensitive limitation of Biacore instrument ($10^6$ $M^{-1}S^{-1}$ for $k_{on}$ and $10^{-6}$ $S^{-1}$ for $k_{off}$). IgG1 m708.5 was also much more effective in binding to both IGF-I and IGF-II than m708.2 as measured by ELISA (FIG. 4). Thus, m708.5 retains its high binding affinity in IgG1 format and in the scFv format.

Example 6

Blocking of IGF-I and IGF-II Bound to MCF-7 Cells

MCF-7 express both IGF-IR and IR. A competitive assay was performed to determine whether m708.5 blocked the binding of IGF-I and IGF-II to IGF-IR and IR on MCF-7 breast cancer cells by flow cytometry. M708.5 was pre-incubated with IGF-I and IGF-II, respectively. The antibodies were allowed to bind to MCF-7 cells. Irrelevant 3A2a scFv and m102.4 IgG as negative control were also mixed with IGF ligands at the same condition. M708.5 in scFv and IgG1 formats completely blocked IGF-I and IGF-II binding to their receptors on MCF-7 cells (FIG. 5). Control scFv and IgG that do not recognize IGFs had no effect. Thus, m708.5 could block IGF-I/II-mediated signals inducing the activation and phosphorylation of IGF-IR and IR on cancer cells.

Example 7

Inhibition of IGF-I and IGF-II Induced IGF-IR Phosphorylation

Figure 6A:
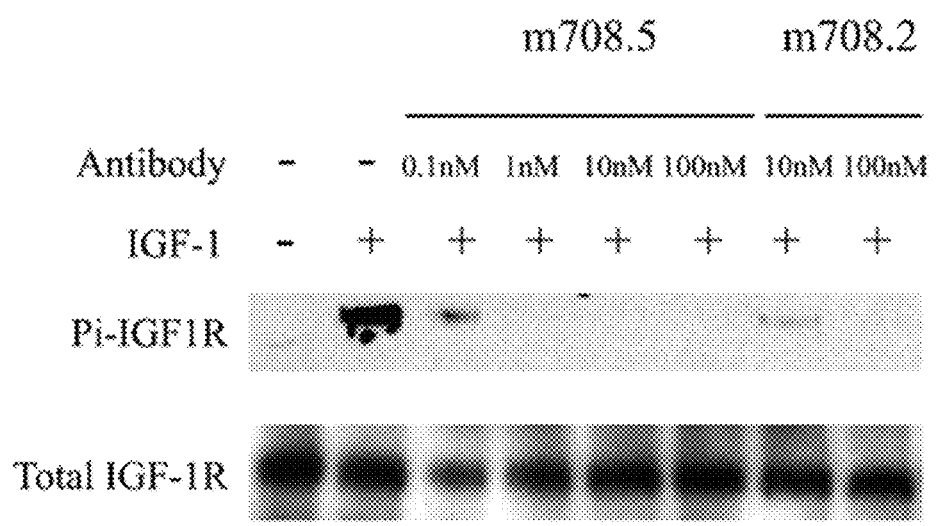
FIGS. 6A and 6B is a set of digital images showing phosphorylation inhibition of IGF-IR by m708.2 and m708.5 in MCF-7 cells. MCF-7 cells were starved in serum free medium for 5 h first, followed by addition of treatment medium with 1 nM IGF-I (a) or 5 nM IGF-II (b) with the indicated concentrations of IgG708.2. Thirty minutes later cells were chilled and lysed. IGF-IR was immunoprecipitated, the phosphorylated IGF-IR was detected with an phospho-tyrosine specific antibody. The total amount of IGF-IR was detected by the same polyclonal antibody used for the immunoprecipitation.
Figure 6B:
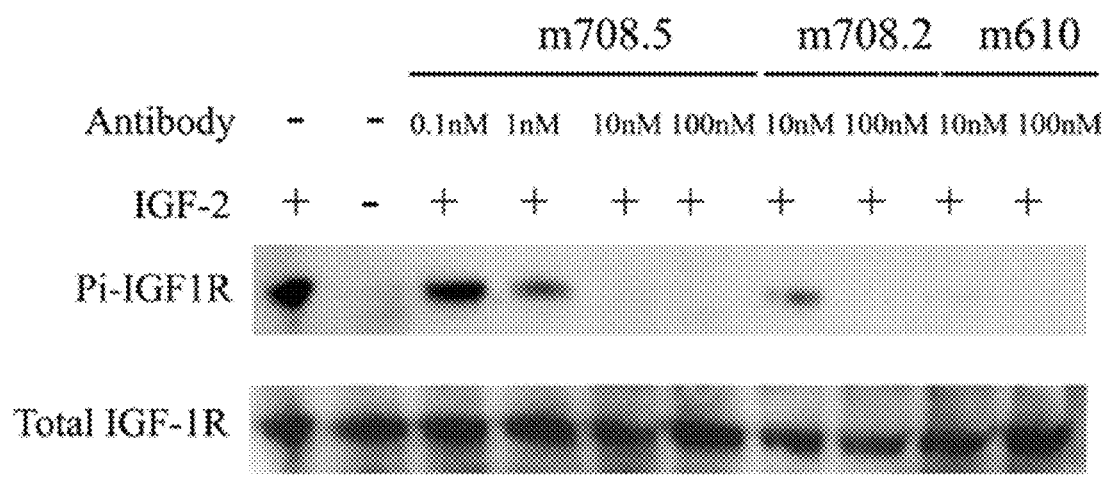
Figure 7A:
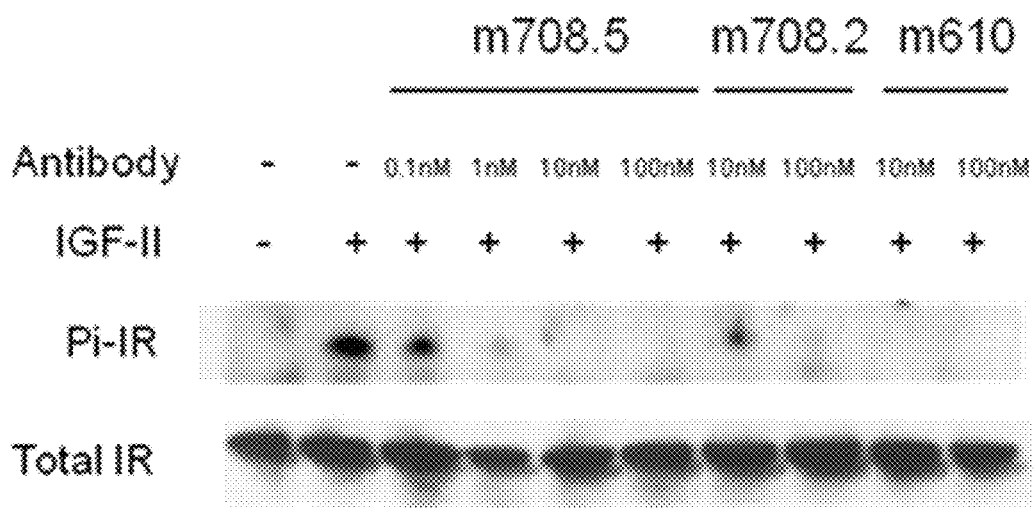
FIGS. 7A and 7B are a sets of digital images. (a) Phosphorylation inhibition of IR by m708.2, m708.5 and m610 in MCF-7 cells. MCF-7 cells were starved and treated with 5 nM IGF-II with indicated concentrations of IgGs. The phosphorylated IR was detected with a phospho-tyrosine specific antibody. The total amount of IR was detected. (b) ELISA of m708.5 to human insulin. IgGs of m708.5 (10 nM) were added to wells coated with IGF-I, IGF-II, human insulin and irrelevant antigens. Bound IgGs were detected with a HRP conjugated anti-human Fc antibody and measured as optical densities at 450 nm.
Figure 7B:
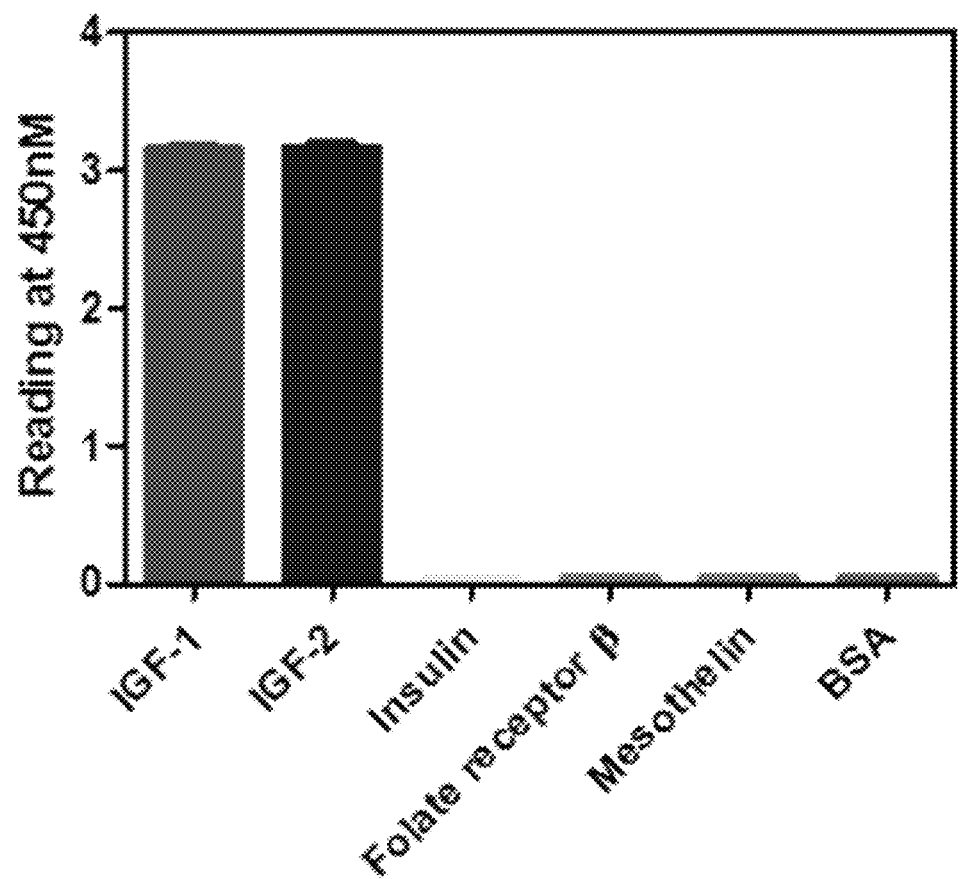
Figure 8:
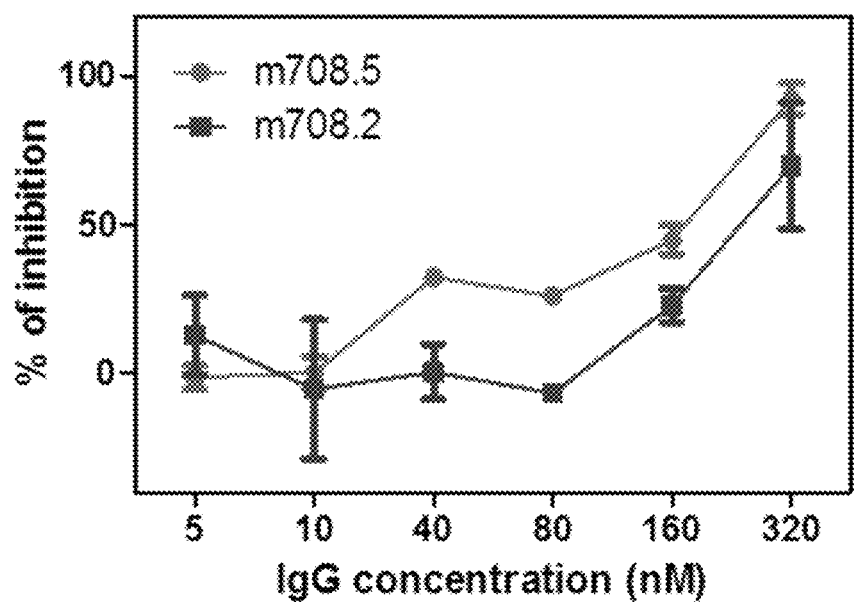
FIG. 8 is a graph of growth inhibition of MCF-7 cells by m708.2 and m708.5. MCF-7 cells were incubated in complete medium overnight. Different concentrations of IgG m708.2 and m708.5 were pre-incubated with added IGF-I (2.5 nM) and IGF-II (2.5 nM) for 15 min. The media of MCF-7 cells were replaced by the mixture of IgG and ligands immediately. Cells were allowed to grow for 3 days, and MTS substrate was added to detect viable cells. The reaction was monitored by absorbance at 450 nM. Positive control was cells in serum free medium with IGF ligands. Blank control was cells in serum free medium without any IGF ligands.

The antibody also inhibited IGF-I-induced (1 nM) or IGF-II-induced (5 nM) phosphorylation Immunoblottings (FIG. 6a) showed that from 1 nM to 100 nM, m708.5 completely inhibited the IGF-I-induced phosphorylation of IGFIR. Similar inhibitory activity was also observed with m708.2, which however only partly blocked IGF-I induced phosphorylation at 10 nM. In addition to IGF-II, both m708.2, m708.5 and m610 were capable of inhibiting IGF-II-induced phosphorylation of IGFIR (FIG. 6b). However, m708.5 was superior to m708.2 and competed with m610. The antibodies also inhibited IGF-II-mediated phosphorylation of the IR induced by 5 nM of IGF-II (FIG. 7a). The inhibition was independent on human insulin that m708.5 did not bind (FIG. 7b). Therefore, m708.5 could effectively inhibit ligand-induced phosphorylation of the two receptors without inhibiting insulin-IR interaction.

Example 8

Inhibition of MCF-7 Cell Growth

In order to investigate whether the blocking of IGF binding by m708.5 is potent enough to inhibit the proliferation of cells, the activity of m708.5 was tested in a cell growth assay using MCF-7 cells. MCF-7 cells produce significant amounts of IGF-II-concentrations up to 35 nM were observed after 3 days (Feng et al., Mol Cancer Ther, 2006. 5(1): p. 114-20). After 3 days, cancer cells were inhibited by near 100% at 320 nM of m708.5 (FIG. 7). Above 40 nM m708.5, the treatment still resulted in obvious cell growth inhibition. In contrast, m708.2 could only inhibit cancer cells beyond 80 nM. These data show that inhibition ability of m708.5 is remarkable, and that this antibody can effectively block tumor cell proliferation in vitro.

The IGF signaling system plays an important role in tumorigenesis LeRoith and Roberts, Cancer Lett, 2003. 195(2): p. 127-37). Human IGF-I and IGF-II share a 62% sequence homology and have overlapping functions: both IGF-I and IGF-II can activate the IGF-IR driving tumor cell proliferation. To further explore novel human antibodies against IGF system, three human antibodies specific for IGF-I utilizing phage display technologies were identified. One of these antibodies, m708, exhibited significant binding to both IGF I and IGF II and was further affinity matured by light-chain shuffling and mutagenesis to finally select a very high affinity antibody, m708.5. This antibody potently inhibited both IGF-I- and IGF-II-induced phosphorylation of IGF-IR, and the growth of cancer cells expressing IGF-IR.

The inhibitory activity of the antibodies was cell type dependent with a likely major determinant the surface concentration of the IGF-IR and the insulin receptor. Many IGF-IR-specific antibodies have been under preclinical study, and several are being evaluated in clinical trials (Pollack et al., Nat Rev Cancer, 2008. 8(12): p. 915-28). For example, a fully human monoclonal antibody (m610) with high affinity to IGF-II was resported that potently blocked the growth/migration of human cancer lines in vitro (Feng et al., Mol Cancer Ther, 2006. 5(1): p. 114-20), and significantly suppressed the growth of prostate cancer cells in a human bone environment (Kimura et al., Clin Cancer Res, 2010. 16(1): p. 121-9). A murine mAb cross-reactive to human IGF-I and IGF-II inhibited the development of new bone tumors, and the progression of established tumors (Goya et al., Cancer Res, 2004. 64(17): p. 6252-8). Recently, a new mAb against IGF-I and IGF-II was reported.

The antibody m708.5 should also exhibit inhibitory activity in vivo. The finding that IgG m708.5 has significantly higher affinity than scFv is important because it would allow to use the IgG antibody format, which is most stable and has longest half-life in vivo; the IgG format may also confer certain effector functions in vivo.

Human monoclonal antibody m708.5 is cross-reactive to both IGF-I and IGF-II with picomolar affinity and potently inhibits the IGF-IR signal transduction function. Thus, m708.5, and the antibodies disclosed herein, offer a new and promising therapeutic strategies for treating tumor and a therapeutic alternatives to agents that target the IGF-IR itself.

Example 9

Bispecific Antibodies

Figure 11:
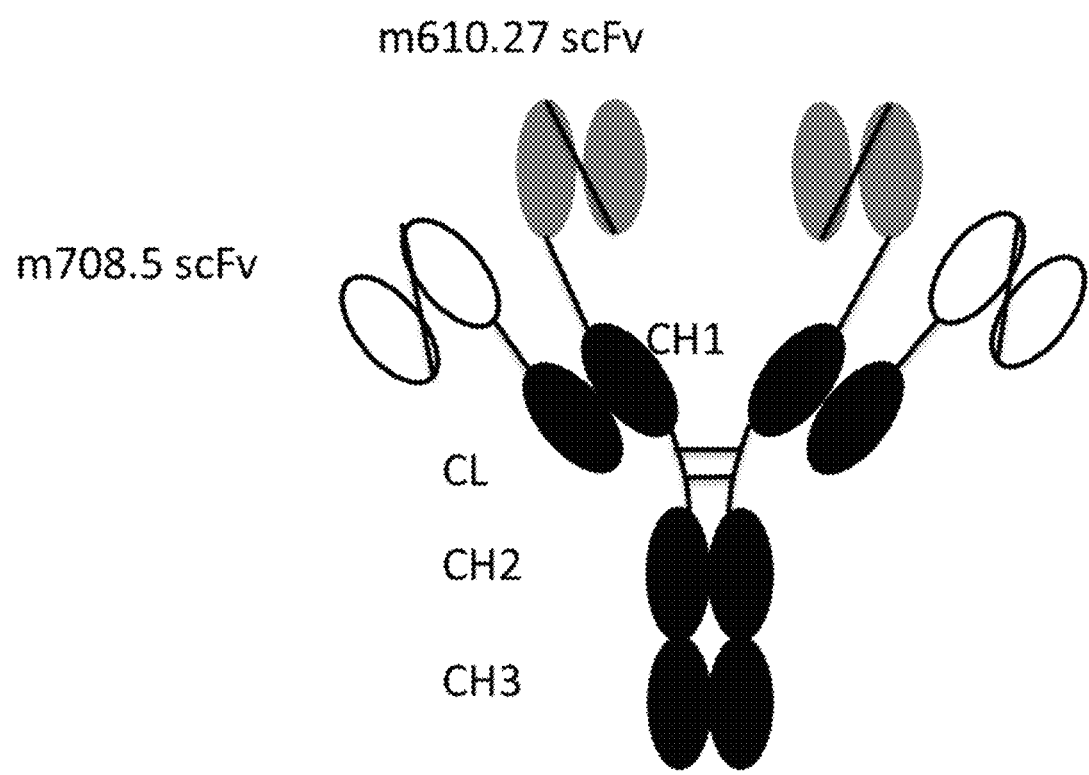
FIG. 11 is a schematic representation of the bispecific antibody, m67. This bispecific antibody was generated by fusing scFv m610.27 and scFv m708.5 to the N terminus of the heavy and light chain constant regions of a human IgG1, respectively, using linkers of $G_4S$ (SEQ ID NO: 25) triplicates.

A schematic representation of an exemplary of a bispecific antibody is shown in FIG. 11. To create m67, scFv m610.27 and scFv m708.5 were fused to the N terminus of the heavy and light chain constant regions of a human IgG1, respectively, using linkers of $G_4S$ triplicates.

Figure 12A:
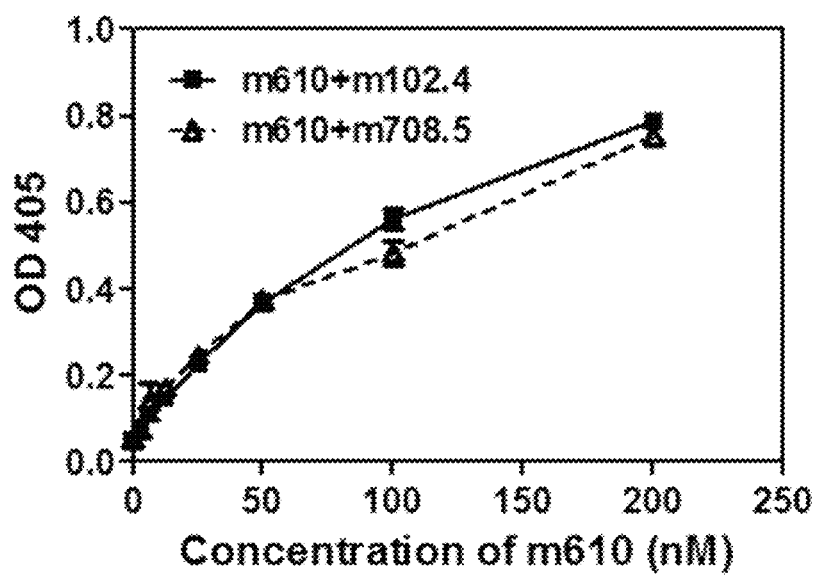
FIGS. 12A and 12B are line graphs showing competition of m610 with m708.5 in binding to IGF-II.
Figure 12B:
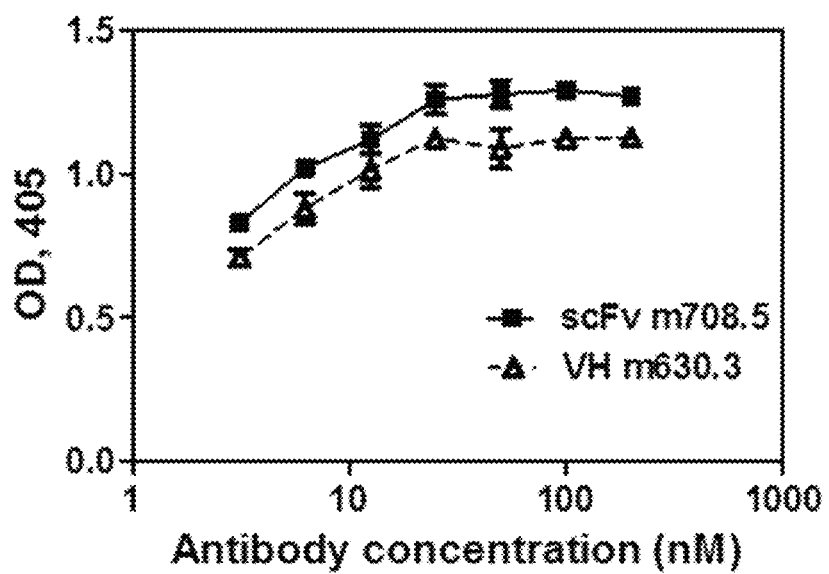

The antibodies were then tested to determine the epitope of IGF-II bound by the antibody. For the results shown in FIG. 12A, IGF-II was directly coated on the ELISA plate. Bound scFv m610 was detected by anti-Flag antibody-HRP in the presence of competing antibody (IgG1 m708.5 or IgG1 m102.4.). M102.4 is an isotype control IgG1 that does not recognize IGF-II. The result indicates that adding m708.5 to the antibody solution does not diminish the m610 binding, indicating that m610 and m708.5 have different epitopes on IGF-II. For the results shown in FIG. 12B, IgG1 m610.27 was coated on the ELISA plate and IGF-II was captured by coated m610.27. Bound scFv m708.5 or V_H m630.3 was detected by HRP-conjugated anti-Flag tag antibody. V_H m630.3 is an anti-IGF-II antibody that is known to have different epitopes from m610. FIG. 12B indicates that m708.5 binds to IGF-II on a different epitope from m610.27.

Figure 13A:
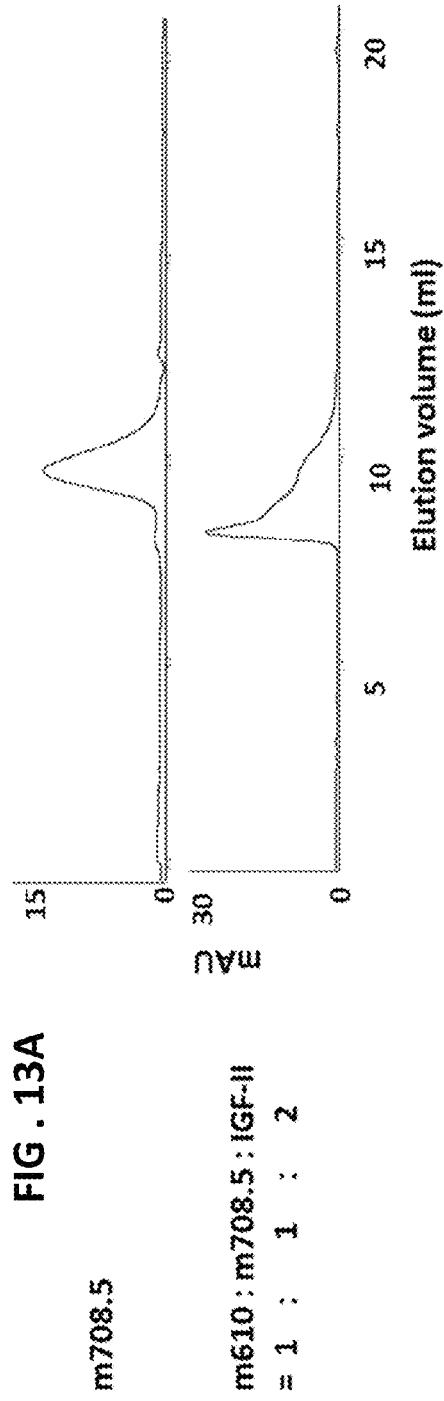
FIGS. 13A and 13B are graphs of results of size-exclusion chromatography analysis of antibodies in the presence of IGFs.
Figure 13B:
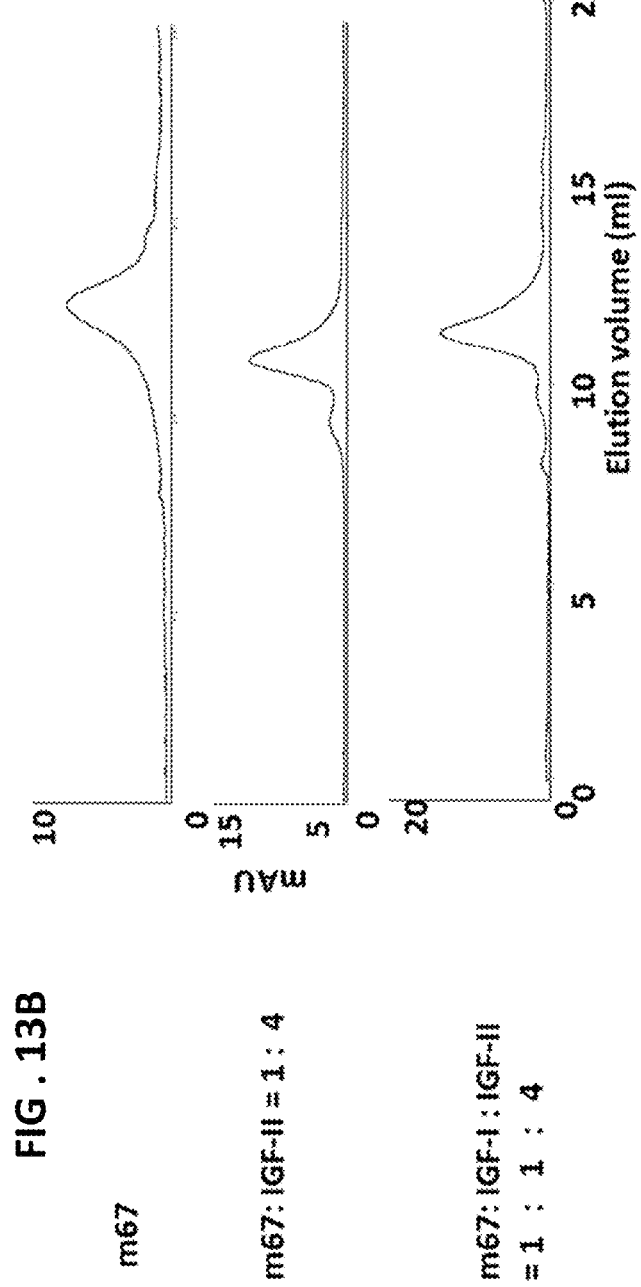

The nature of the complex of m67 and IGF-II was then investigated. For the results shown in FIG. 13A, IgG1 m708.5 or the mixture of IgG1 m610 and IgG1 m708.5 plus IGF-II was analyzed by Superdex G75 column Because m610 and m708.5 have different epitopes on IGF-II and each antibody is bivalent, together they form multimer complex, which are eluted from the Supedex75 column much early than the m708.5 alone. As shown in FIG. 13B, m67, the mixture of m67 and or the mixture of m67/IGF-II plus IGF-I was analyzed by Superdex G200 column. The bispecific antibody, m67, and IGF-II form similar large complex.

The stability of m67 and m708.5 in human sera was also evaluated. As shown in FIG. 14, m67 (FIG. 14A) an dm708.5 (FIG. 14B) were incubated with equal volume of human sera at 37° C. for 9 days and then tested to bind to IGF-I and IGF-II by ELISA. The result indicated that both antibodies retains their binding ability after incubation with serum for 9 days.

m67 inhibited the binding of IGF-I (FIG. 15A) and IGF-II (FIG. 15B) to MCF7 cells better than m610.27 and m708.5 alone. For these studies, MCF-7 cells were incubated with 5 nM biotinylated IGF-I or 1 nM biotinylated IGF-II in the absence or presence of antibodies. Bound biotinylated IGF-I or IGF-II was detected by streptavidin-PE. Control cells incubated with streptavidin-PE only were indicated with black fills. m610.27 did not inhibit the binding of IGF-II to cells at the concentration used in the assay due to its relatively low affinity. m708.5 inhibited the binding of IGF-I better than that of IGF-II. However, the bi-specific antibody m67 was able to inhibit both IGF-I and IGF-II from binding to cells. The result indicates that the two binding moieties of m67 have a synergistic effect.

Figure 16:
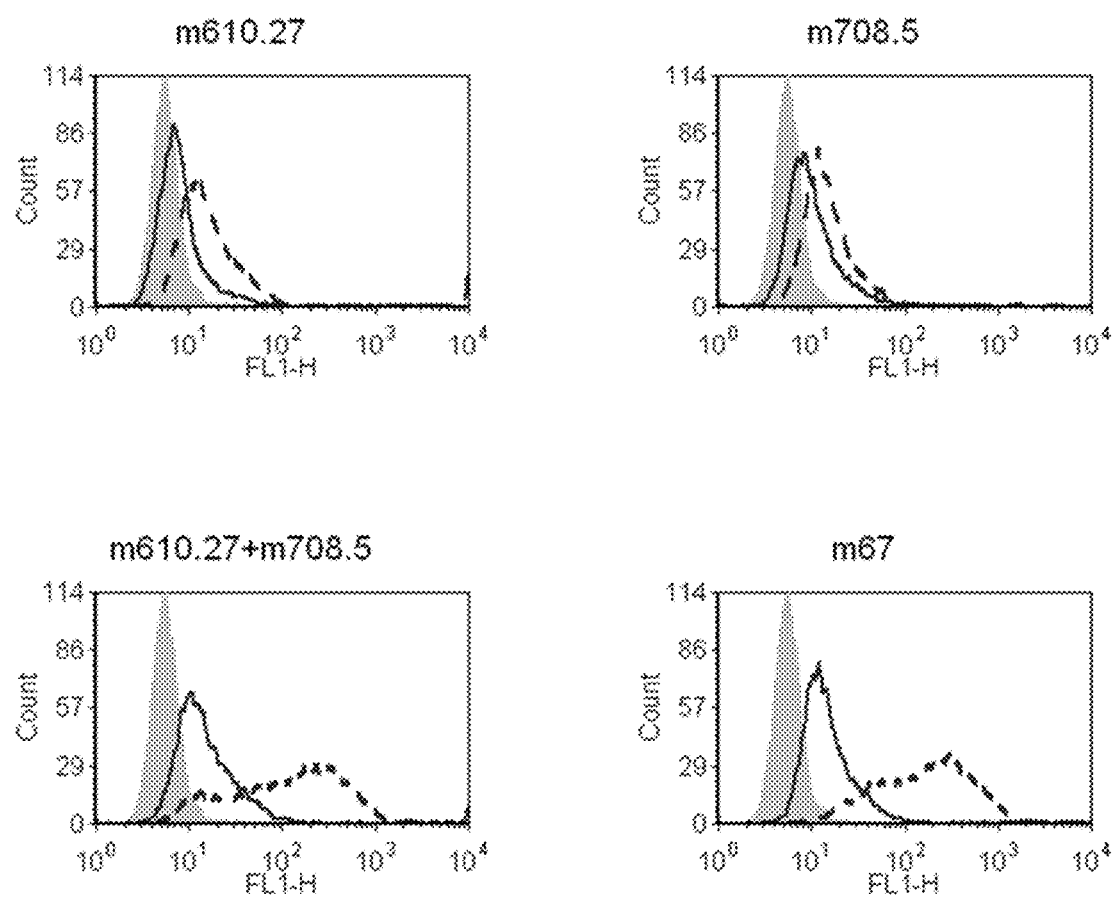
FIG. 16 is a set of graphs showing binding of antibodies to BJAB Cells in the presence of IGF-II. Bound biotinylated IGF-I or IGF-II was detected by Streptavidin-PE. Blank cells incubated with Streptavidin-PE conjugate are in grey. Cells incubated with IGF-II only are indicated by a solid line. Those for IGF-II with antibodies are shown by a dashed line.

The ligand/antibody complexes formed between IGF-II/ m67 or IGF-II/m610.27+m708.5 are able to bind to Fc gamma receptor II on BJAB cells (see FIG. 16). For these studies, bound biotinylated IGF-I or IGF-II was detected by Streptavidin-PE. BJAB cells are known to have low affinity Fc gamma receptor II, which only binds to a cluster of IgG molecules but not to a single IgG. The mono-specific antibody, m610.27 and m708.5 each recognized a single epitope on IGF-II, therefore, they did not form multi-IgG complex with IGF-II. They also did not bind to the BJAB cells. The bi-specific m67 forms multi-IgG complex with IGF-II. With multiple copies of IgG on the complex, the avidity effect rendered binding ability to BJAB cells. The mixture of m610.27 and m708.5 functions similarly to m67.

Figure 17:
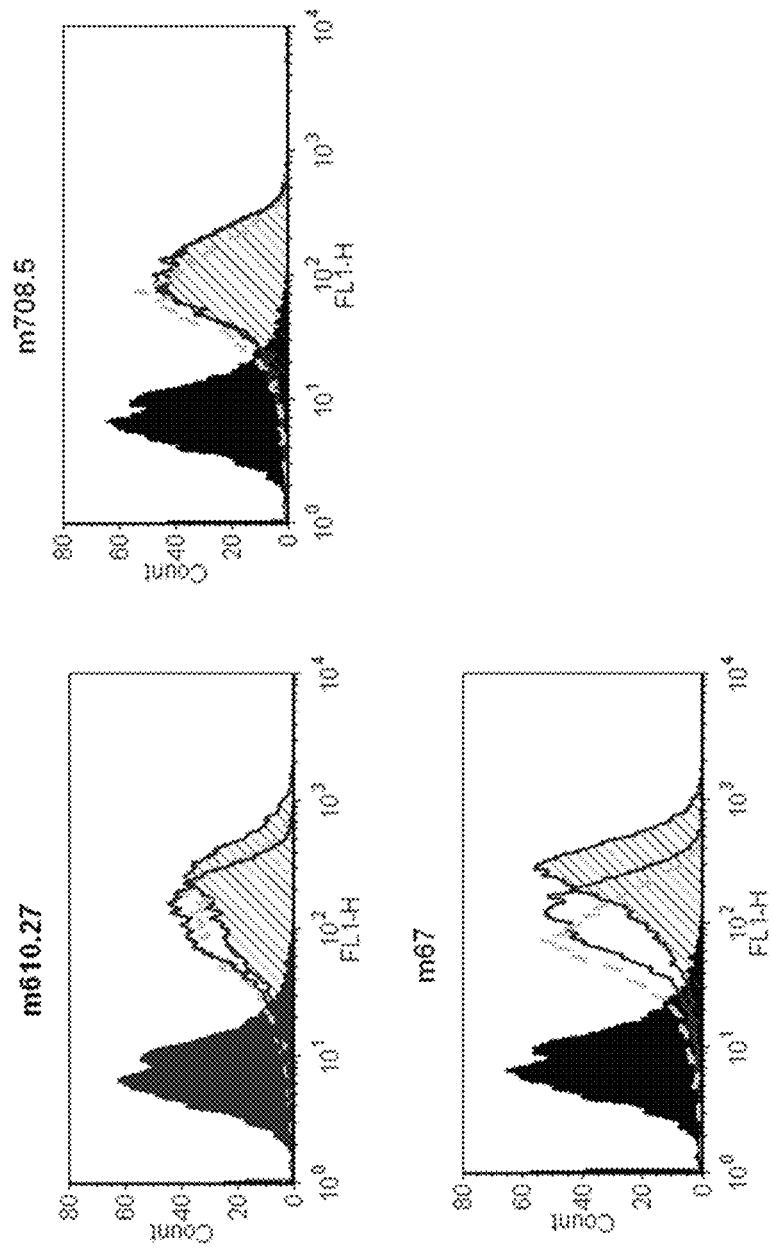
FIG. 17 is a set of graphs showing biding of antibodies to U937 Cells in the presence of IGF-II. Bound antibodies were detected by FITC-conjugated goat F(ab')2 anti-human Fc IgG antibody. The black (filled in) histograms are the blank cells incubated with the secondary antibody only. The histograms for cells incubated with antibody alone (hatched area), the mixture of antibody and IGF-II (dashed line), and the mixture of the antibody, IGF-II and Cytochalasin D (solid line) are shown.

IGF-II/m67 complexes are endocytosed by macrophage-like U937 cells, whereas IGF-II/m610.27 or IGF-II/m708.5 complexes are not taken in by U937 cells (see FIG. 17). U937 cells have high affinity receptor for IgG. Both mono-specific and bi-specific antibodies are able to bind to U937 cells. However, only the m67/IGF-II complex is efficiently taken in due to the multiple copies of IgG on the complex. The two mono-specific antibodies, m610.27 and m708.5, do not form multimers with IGF-II and are not endocytosed by U937 cells. The endocytosis of m67/IGF-II complex is inhibited by cytochalasin D, an inhibitor of actin polymerization. The endocytosis process is dependent on the actin filaments.

m67 had stronger inhibition on IGF1R and IR phosphorylation than the parental mono-specific antibodies (see FIG. 18). Specifically, m67 inhibited IGF-I induced phosphorylation of IGF-1R at 1 nM, similar to m708.5. It inhibited IGF-II induced phosphorylation of IGF-1R at 0.2 nM, better than both m610.27 and m708.5. Because m610.27 only recognizes IGF-II but not IGF-I, the ability of m67 to inhibit IGF-I binding derives from m708.5 alone. However, because m610.27 and m708.5 bind to two non-overlapping epitopes on IGF-II, m67 inhibited IGF-II binding better than the single antibody, again providing evidence of a synergistic effect.

It will be apparent that the precise details of the methods or compositions described may be varied or modified without departing from the spirit of the described invention. We claim all such modifications and variations that fall within the scope and spirit of the claims below.

The invention claimed is:

1. An isolated nucleic acid molecule encoding a single chain Fv protein (scFv),
   wherein the scFv comprises a heavy chain variable region and a light chain variable region,
   wherein the heavy chain variable region comprises the amino acid sequence set forth as amino acids 26-33 of SEQ ID NO: 7, amino acids 51-58 of SEQ ID NO: 7, and amino acids 97-109 of SEQ ID NO: 7, wherein residue 56 is G and residue 109 is N; and
   wherein the light chain variable region comprises the amino acid sequence set forth as amino acids 27-32 of SEQ ID NO: 8, amino acids 50-52 of SEQ ID NO: 8 and amino acids 89-97 of SEQ ID NO: 8, and wherein the scFv specifically binds insulin-like growth factor II (IGF-II) with an equilibrium dissociation constant ($K_d$) of 200 pM or less and specifically binds IGF-I with an equilibrium dissociation constant ($K_d$) of 200 pM or less.

2. The isolated nucleic acid molecule of claim 1, operably linked to a promoter.

3. An expression vector comprising the isolated nucleic acid molecule of claim 1.

4. The expression vector of claim 3, wherein the heavy chain variable region is encoded by the nucleic acid sequence set forth as SEQ ID NO: 11 and wherein the light chain variable region is encoded by the nucleic acid sequence set forth as SEQ ID NO: 12.

5. An isolated host cell transformed with the nucleic acid molecule of claim 2.

6. A method of producing a single chain Fv protein (scFv) comprising:
   a) transforming a host cell in vitro with the vector of claim 3, wherein the scFv is expressed by the host cell; and
   b) purifying the scFv from the host cell, thereby producing the scFv.

7. The isolated nucleic acid molecule of claim 1, wherein the heavy chain variable domain comprises the amino acid sequence set forth as SEQ ID NO: 7, wherein residue 7 is L; residue 20 is V; residue 23 is K; residue 37 is V; residue 56 is G; residue 61 is A; residue 62 is Q; residue 74 is K; residue 76 is T; residue 77 is S; residue 79 is A; residue 85 is S; residue 87 is G; residue 109 is N; residue 111 is G; and residue 115 is L.

8. The isolated nucleic acid molecule of claim 1, further encoding a polypeptide label.

9. The isolated nucleic acid molecule of claim 8, wherein the polypeptide label is a fluorescent protein or an enzyme.

10. A composition comprising the isolated nucleic acid molecule of claim 1, and a pharmaceutically acceptable carrier.

11. The isolated nucleic acid molecule of claim 1 wherein the heavy chain variable region is encoded by the nucleic acid sequence set forth as SEQ ID NO: 19.

12. The isolated nucleic acid molecule of claim 1, wherein the light chain variable domain comprises the amino acid sequence set forth as SEQ ID NO: 8.

13. The isolated nucleic acid molecule of claim 1, wherein the heavy chain variable region is encoded by the nucleic acid sequence set forth as SEQ ID NO: 21 and the wherein the light chain variable regions is encoded by the nucleic acid sequence set forth SEQ ID NO: 22.

14. An isolated nucleic acid molecule encoding a heavy chain variable region comprising the amino acid sequence set forth as amino acids 26-33 of SEQ ID NO: 7, amino acids 51-58 of SEQ ID NO: 7, and amino acids 97-109 of SEQ ID NO: 7, wherein residue 56 is G and residue 109 is N; and
   wherein the heavy chain variable region, in conjunction with a light chain variable region, forms a human monoclonal antibody or antigen binding fragment that specifically binds insulin-like growth factor II (IGF-II) with an equilibrium dissociation constant ($K_d$) of 200 pM or less and specifically binds IGF-I with an equilibrium dissociation constant ($K_d$) of 200 pM or less.

15. The isolated nucleic acid molecule of claim 14, wherein the heavy chain variable domain comprises the amino acid sequence set forth as SEQ ID NO: 7, wherein residue 7 is L; residue 20 is V; residue 23 is K; residue 37 is V; residue 56 is G; residue 61 is A; residue 62 is Q; residue 74 is K; residue 76 is T; residue 77 is S; residue 79 is A; residue 85 is S; residue 87 is G; residue 109 is N; residue 111 is G; and residue 115 is L.

16. The isolated nucleic acid molecule of claim 14, wherein the heavy chain variable domain comprises the amino acid sequence set forth as SEQ ID NO: 7.

17. The isolated nucleic acid molecule of claim 14, comprising the nucleic acid sequence set forth as SEQ ID NO: 11, SEQ ID NO: 19, or SEQ ID NO: 21.

18. The isolated nucleic acid molecule of claim 14, operably linked to a promoter.

19. A vector comprising the isolated nucleic acid molecule of claim 18.

20. An isolated host cell transformed with the vector of claim 19.

21. A composition comprising the isolated nucleic acid molecule of claim 18 and a pharmaceutically acceptable carrier.

22. An isolated nucleic acid molecule encoding a light chain variable region comprising the amino acid sequence set forth as amino acids 27-32 of SEQ ID NO: 8, amino acids 50-52 of SEQ ID NO: 8 and amino acids 89-97 of SEQ ID NO: 8,
   wherein the light chain variable region, in conjunction with a heavy chain variable forms a human monoclonal antibody or antigen binding fragment that specifically binds insulin-like growth factor II (IGF-II) with an equilibrium dissociation constant ($K_d$) of 200 pM or less and specifically binds IGF-I with an equilibrium dissociation constant ($K_d$) of 200 pM or less.

23. The isolated nucleic acid molecule of claim 22, wherein the light chain variable domain comprises the amino acid sequence set forth as SEQ ID NO: 8.

24. The isolated nucleic acid molecule of claim 22, comprising the nucleic acid sequence set forth as SEQ ID NO: 12 or SEQ ID NO: 22.

25. The isolated nucleic acid molecule of claim 22, operably linked to a promoter.

26. A composition comprising the isolated nucleic acid molecule of claim 25, and a pharmaceutically acceptable carrier.

27. A vector comprising the isolated nucleic acid molecule of claim 25.

28. An isolated host cell transformed with the vector of claim 27.

* * * * *